United States Patent
Ohsawa et al.

(10) Patent No.: US 9,233,919 B2
(45) Date of Patent: Jan. 12, 2016

(54) SULFONIUM SALT-CONTAINING POLYMER, RESIST COMPOSITION, PATTERNING PROCESS, AND SULFONIUM SALT MONOMER AND MAKING METHOD

(71) Applicant: SHIN-ETSU CHEMICAL CO., LTD., Chiyoda-ku, Tokyo (JP)

(72) Inventors: Youichi Ohsawa, Joetsu (JP); Masaki Ohashi, Joetsu (JP); Seiichiro Tachibana, Joetsu (JP); Jun Hatakeyama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 17 days.

(21) Appl. No.: 14/306,523

(22) Filed: Jun. 17, 2014

(65) Prior Publication Data

US 2014/0296561 A1 Oct. 2, 2014

Related U.S. Application Data

(62) Division of application No. 13/292,127, filed on Nov. 9, 2011.

(30) Foreign Application Priority Data

Nov. 19, 2010 (JP) ................................. 2010-258496

(51) Int. Cl.
| | |
|---|---|
| G03F 7/004 | (2006.01) |
| G03F 7/38 | (2006.01) |
| C07C 303/32 | (2006.01) |
| C07C 309/20 | (2006.01) |
| C07C 381/12 | (2006.01) |
| C07C 69/54 | (2006.01) |
| C08F 220/24 | (2006.01) |
| C08F 220/38 | (2006.01) |
| C08F 228/02 | (2006.01) |
| C07C 309/12 | (2006.01) |
| C08F 20/38 | (2006.01) |
| C08F 220/18 | (2006.01) |
| G03F 7/039 | (2006.01) |
| G03F 7/20 | (2006.01) |

(52) U.S. Cl.
CPC ............... *C07C 309/20* (2013.01); *C07C 69/54* (2013.01); *C07C 303/32* (2013.01); *C07C 309/12* (2013.01); *C07C 381/12* (2013.01); *C08F 20/38* (2013.01); *C08F 220/18* (2013.01); *C08F 220/24* (2013.01); *C08F 220/38* (2013.01); *C08F 228/02* (2013.01); *G03F 7/0045* (2013.01); *G03F 7/0046* (2013.01); *G03F 7/0392* (2013.01); *G03F 7/0397* (2013.01); *G03F 7/2041* (2013.01); *G03F 7/38* (2013.01); *Y10S 430/106* (2013.01); *Y10S 430/111* (2013.01); *Y10S 430/122* (2013.01)

(58) Field of Classification Search
CPC .. C07C 303/32; C07C 309/20; C07C 381/12; C07C 69/54; C08F 220/24; C08F 220/38; C08F 228/02; G03F 7/0397; G03F 7/38; G03F 7/0045
USPC .............. 430/270.1, 326, 905, 907, 910, 921; 526/243, 245, 280; 562/109, 113; 560/205, 222, 223
See application file for complete search history.

(56) References Cited

U.S. PATENT DOCUMENTS

| | | | |
|---|---|---|---|
| 5,650,483 A | 7/1997 | Malik et al. | |
| 5,705,702 A | 1/1998 | Osawa et al. | |
| 6,312,867 B1 | 11/2001 | Kinsho et al. | |
| 7,569,326 B2 | 8/2009 | Ohsawa et al. | |
| 7,771,913 B2 | 8/2010 | Kaneko et al. | |
| 7,871,752 B2 | 1/2011 | Hasegawa et al. | |
| 8,048,610 B2 | 11/2011 | Ohsawa et al. | |
| 8,158,327 B2 | 4/2012 | Joo et al. | |
| 8,785,105 B2* | 7/2014 | Ohsawa et al. | 430/270.1 |
| 2004/0053158 A1* | 3/2004 | Yamato et al. | 430/270.1 |
| 2008/0102407 A1 | 5/2008 | Ohsawa et al. | |
| 2009/0269696 A1 | 10/2009 | Ohsawa et al. | |
| 2010/0040977 A1 | 2/2010 | Nagai et al. | |
| 2010/0075256 A1 | 3/2010 | Joo et al. | |
| 2010/0221664 A1 | 9/2010 | Nishimura et al. | |
| 2010/0227274 A1 | 9/2010 | Hatakeyama et al. | |
| 2011/0143279 A1* | 6/2011 | Shimokawa et al. | 430/270.1 |
| 2011/0177453 A1 | 7/2011 | Masabuchi et al. | |

FOREIGN PATENT DOCUMENTS

| | | |
|---|---|---|
| EP | 2 112 554 A2 | 10/2009 |
| EP | 2 112 554 A3 | 12/2010 |
| JP | 3063615 B2 | 7/2000 |
| JP | 2000-336121 A | 12/2000 |
| JP | 2007-297590 A | 11/2007 |

(Continued)

OTHER PUBLICATIONS

Extended European Search Report issued Mar. 16, 2012, in European Patent Application No. 11187377.4.

*Primary Examiner* — John S Chu
(74) *Attorney, Agent, or Firm* — Birch, Stewart, Kolasch & Birch, LLP

(57) ABSTRACT

A sulfonium salt having a 4-fluorophenyl group is introduced as recurring units into a polymer comprising hydroxyphenyl (meth)acrylate units and acid labile group-containing (meth)acrylate units to form a polymer which is useful as a base resin in a resist composition. The resist composition has a high sensitivity, high resolution and minimized LER.

2 Claims, 6 Drawing Sheets

(56) References Cited

FOREIGN PATENT DOCUMENTS

| JP | 2008-31298 A | 2/2008 |
|---|---|---|
| JP | 2008-133448 A | 6/2008 |
| JP | 4175115 B2 | 11/2008 |
| JP | 4207623 B2 | 1/2009 |
| JP | 2009-263487 A | 11/2009 |
| JP | 2010-044372 A1 | 4/2010 |
| JP | 2010-77377 A | 4/2010 |
| WO | WO 02/092559 A1 | 11/2002 |

\* cited by examiner

SULFONIUM SALT-CONTAINING POLYMER, RESIST COMPOSITION, PATTERNING PROCESS, AND SULFONIUM SALT MONOMER AND MAKING METHOD

CROSS-REFERENCE TO RELATED APPLICATION

The present application is a 37 C.F.R. §1.53(b) divisional of, and claims priority to, U.S. application Ser. No. 13/292, 127, filed Nov. 9, 2011. Priority is also claimed to Japanese Application No. 2010-258496 filed on Nov. 19, 2010. The entire contents of each of these applications is hereby incorporated by reference.

TECHNICAL FIELD

This invention relates to (1) a polymerizable sulfonium salt comprising a fluorinated sulfonium cation and an anion having a polymerizable unit, (2) a polymer comprising units of the sulfonium salt, (3) a resist composition comprising the polymer, and (4) a process for patterning the resist composition using high-energy radiation.

BACKGROUND ART

While a number of recent efforts are being made to achieve a finer pattern rule in the drive for higher integration densities and operating speeds in LSI devices, DUV and EUV lithography is thought to hold particular promise as the next generation in microfabrication technology. In particular, photolithography using an ArF excimer laser as the light source is thought requisite to the micropatterning technique capable of achieving a feature size of 0.13 μm or less.

The lithography techniques which are considered promising next to the ArF lithography include electron beam (EB) lithography, $F_2$ lithography, extreme ultraviolet (EUV) lithography, and x-ray lithography. In these techniques, exposure must be done in vacuum or reduced pressure, which allows the sulfonic acid generated during exposure to volatilize, failing to form a satisfactory pattern profile. The sulfonic acid volatilized can damage the exposure system. In the EB and EUV lithography, it is desired to make a resist material more sensitive in order to reduce the burden on the exposure system.

Under the circumstances, development efforts were made to introduce photoacid generator units into a resin for the purposes of improving resolution, reducing PED size change, and suppressing dissolution of acid generator additive in immersion liquid (typically water) during the ArF immersion lithography. Patent Document 1 (JP-A 2008-133448) describes a polymer comprising units of triphenylsulfonium 1-(difluorosulfomethyl)-2,2,2-trifluoroethyl methacrylate (or triphenylsulfonium 1,1,3,3,3-pentafluoro-2-methacryloyloxy-propane-1-sulfonate). Patent Document 2 (JP-A 2009-263487) describes that a polymer comprising the above-mentioned units and polymerization units having a phenolic hydroxyl group has a higher sensitivity. Patent Document 3 (JP-A 2010-077377) discloses 4-fluorophenyldiphenylsulfonium 1,1-difluoro-1-sulfoethyl methacrylate, a polymer comprising the same as polymerization units, and a resist material.

According to the inventors' research work, the sulfonium salt having a triphenylsulfonium cation has a fully high sensitivity to ArF and KrF exposures, but an insufficient sensitivity to EUV exposure. Even when the salt is combined with a specific polymerization unit as in Patent Document 2, an improvement in sensitivity is still desired. The problem has not been overcome by Patent Document 3 because the sulfonium salt itself is low soluble in polymerization solvents and the resulting polymer is less soluble in resist solvents.

Like the prior art KrF and ArF resists, the EUV resist also suffers from a problem of line edge roughness (LER), which is desired to be overcome.

CITATION LIST

Patent Document 1: JP-A 2008-133448 (U.S. Pat. No. 7,569,326)
Patent Document 2: JP-A 2009-263487
Patent Document 3: JP-A 2010-077377

DISCLOSURE OF INVENTION

An object of the invention is to provide a sulfonium salt having a polymerizable anion useful as a monomer, a polymer obtained therefrom and effective as a base resin for resist use, and a resist composition comprising the polymer, the resist composition being improved in sensitivity, resolution and LER when processed by photolithography using high-energy radiation such as ArF excimer laser lithography and EUV lithography, especially EUV lithography. Another object is to provide a pattern forming process using the composition.

The inventors have found that when a sulfonium salt having a 4-fluorophenyl group represented by formula (1) is introduced as recurring units into a polymer comprising hydroxyphenyl(meth)acrylate units represented by formula (2) and acid labile group-containing (meth)acrylate units represented by formula (3), the resulting polymer is useful as a base resin in a resist composition, and that the resist composition has improved properties including high sensitivity, high resolution and minimized LER. The resist composition comprising the polymer is fully effective for high accuracy micropatterning.

In a first aspect, the invention provides a polymer comprising recurring units having the general formulae (1a), (2), and (3):

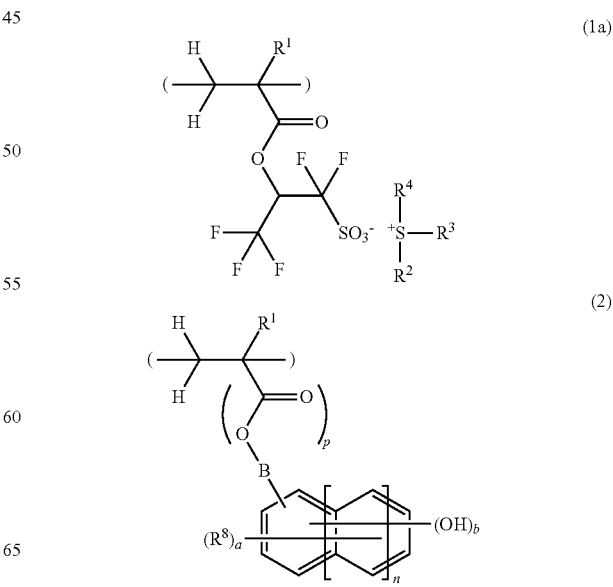

(3)

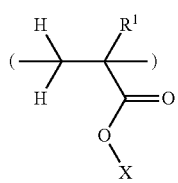

wherein $R^1$ is hydrogen, fluorine, methyl or trifluoromethyl, $R^2$, $R^3$, and $R^4$ are each independently a substituted or unsubstituted, straight or branched $C_1$-$C_{10}$ alkyl, alkenyl or oxoalkyl group, a substituted or unsubstituted $C_6$-$C_{18}$ aryl, aralkyl or aryloxoalkyl group, or 4-fluorophenyl group, any two of $R^2$, $R^3$, and $R^4$ may bond together to form a ring with the sulfur atom, with the proviso that at least one of $R^2$, $R^3$, and $R^4$ is a 4-fluorophenyl group, n is an integer of 0 to 2, $R^8$ is hydrogen or a $C_1$-$C_{10}$ alkyl group, p is 0 or 1, B is a single bond or a $C_1$-$C_{10}$ divalent organic group which may be substituted with an oxygen atom, a is an integer of 0 to 3, b is an integer of 1 to 3, and X is an acid labile group.

The polymer may further comprise recurring units of at least one type selected from the general formulae (4), (5), and (6):

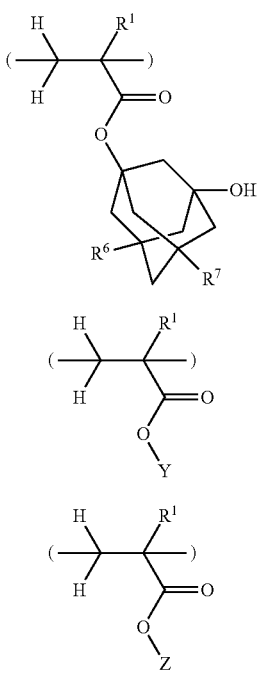

(4)

(5)

(6)

wherein $R^1$ is hydrogen, fluorine, methyl or trifluoromethyl, $R^6$ and $R^7$ are each independently hydrogen or hydroxyl, Y is a substituent group having lactone structure, Z is hydrogen, a $C_1$-$C_{15}$ fluoroalkyl group or $C_1$-$C_{15}$ fluoroalcohol-containing substituent group.

The polymer may further comprise recurring units of at least one type selected from the general formulae (7), (8), and (9):

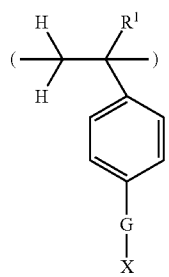

(7)

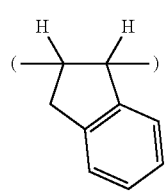

(8)

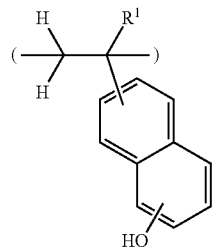

(9)

wherein $R^1$ is hydrogen, fluorine, methyl or trifluoromethyl, X is an acid labile group, and G is an oxygen atom or carbonyloxy (—C(=O)O—) group.

In a second aspect, the invention provides a positive resist composition comprising the polymer defined above as a base resin, and specifically, a positive resist composition comprising the polymer defined above and a polymer other than the polymer comprising recurring units having formulae (1a), (2) and (3) as a base resin.

The positive resist composition may further comprise a surfactant which is insoluble in water and soluble in an alkaline developer.

In a third aspect, the invention provides a process for forming a pattern, comprising the steps of coating the positive resist composition defined above onto a substrate and heat treating to form a resist film, exposing the resist film to high-energy radiation through a photomask, optionally heat treating, and developing the exposed resist film with a developer;

a process for forming a pattern, comprising the steps of coating the positive resist composition defined above onto a substrate and heat treating to form a resist film, coating onto the resist film a protective film which is insoluble in water and soluble in alkaline developer, exposing the resist film to high-energy radiation through a photomask with water held between the substrate and a projection lens, optionally heat treating, and developing the exposed resist film with a developer;

a process for forming a pattern, comprising the steps of coating the positive resist composition defined above onto a substrate and heat treating to form a resist film, imagewise writing with an electron beam, optionally heat treating, and developing the resist film with a developer; or a process for forming a pattern, comprising the steps of coating the positive resist composition defined above onto a substrate and heat treating to form a resist film, exposing the resist film to soft x-ray with a wavelength of 3 to 15 nm, optionally heat treating, and developing the resist film with a developer.

In a fourth aspect, the invention provides a sulfonium salt having the general formula (1):

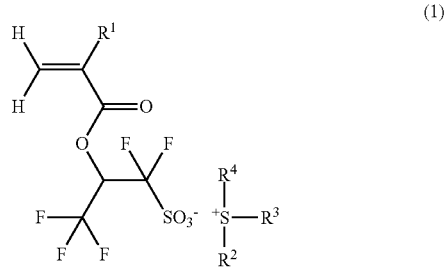

(1)

wherein $R^1$, $R^2$, $R^3$, and $R^4$ are as defined above.

In a fifth aspect, the invention provides a method for preparing the sulfonium salt of formula (1) by effecting ion exchange between an ammonium salt having the general formula (1b) and a 4-fluorophenylsulfonium salt having the general formula (1c):

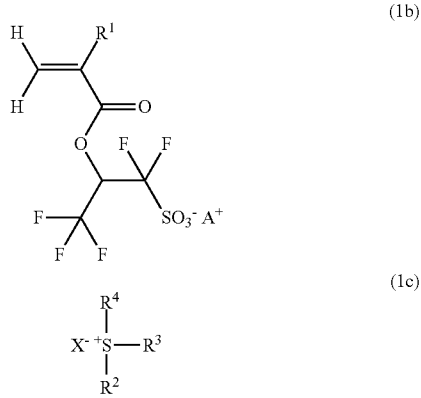

(1b)

(1c)

wherein $R^1$, $R^2$, $R^3$, and $R^4$ are as defined above, $A^+$ is an ammonium cation or a $C_1$-$C_{16}$ primary, secondary, tertiary or quaternary ammonium cation, and $X^-$ is a fluoride ion, chloride ion, bromide ion, iodide ion or methyl sulfate.

It is noted that the resist composition of the invention can also be applied to the immersion lithography. The immersion lithography involves exposing a prebaked resist film to light from a projection lens with a liquid medium interposed between the resist film and the projection lens. The ArF immersion lithography generally uses pure water as the immersion medium. This technology, combined with a projection lens having a NA of at least 1.0, is important for the ArF lithography to survive to the 65 nm node and forth, with a further development thereof being accelerated.

The resist composition of the invention allows the feature size of the pattern after development to be reduced by various shrinkage techniques. For example, the hole size can be shrunk by such known techniques as thermal flow, RELACS, SAFIRE, and WASOOM. More effective shrinkage of hole size by thermal flow is possible particularly when a hydrogenated cycloolefin ring-opening metathesis polymerization (ROMP) polymer having a low Tg is blended in the composition.

Advantageous Effects of Invention

The inventive sulfonium salt is well soluble in polymerization solvents and the polymer thereof is fully soluble in resist solvents. The synthesis method is successful in the synthesis of a 4-fluorophenylsulfonium salt through hydrolysis and acyl exchange, which route was impossible in the prior art.

When the polymer is used as a base resin in a radiation-sensitive resist composition, the composition offers a high sensitivity, high resolution, and minimized LER. The resist composition comprising the polymer is fully effective for high accuracy micropatterning. In the practice of ArF immersion lithography, the polymer prevents leach-out in water and also minimizes the influence of water left on the wafer. In the practice of EUV lithography, the polymer is effective for suppressing outgassing, improving LER, and restraining defect formation. In the disposal of resist-containing waste liquid after the device fabrication, (meth)acrylic ester moieties are hydrolyzable under basic conditions so that the polymers can be converted into less accumulative compounds of lower molecular weight. In the case of disposal by combustion, the polymers are more combustible because of a low degree of fluorine substitution.

DESCRIPTION OF EMBODIMENTS

Figure 1:
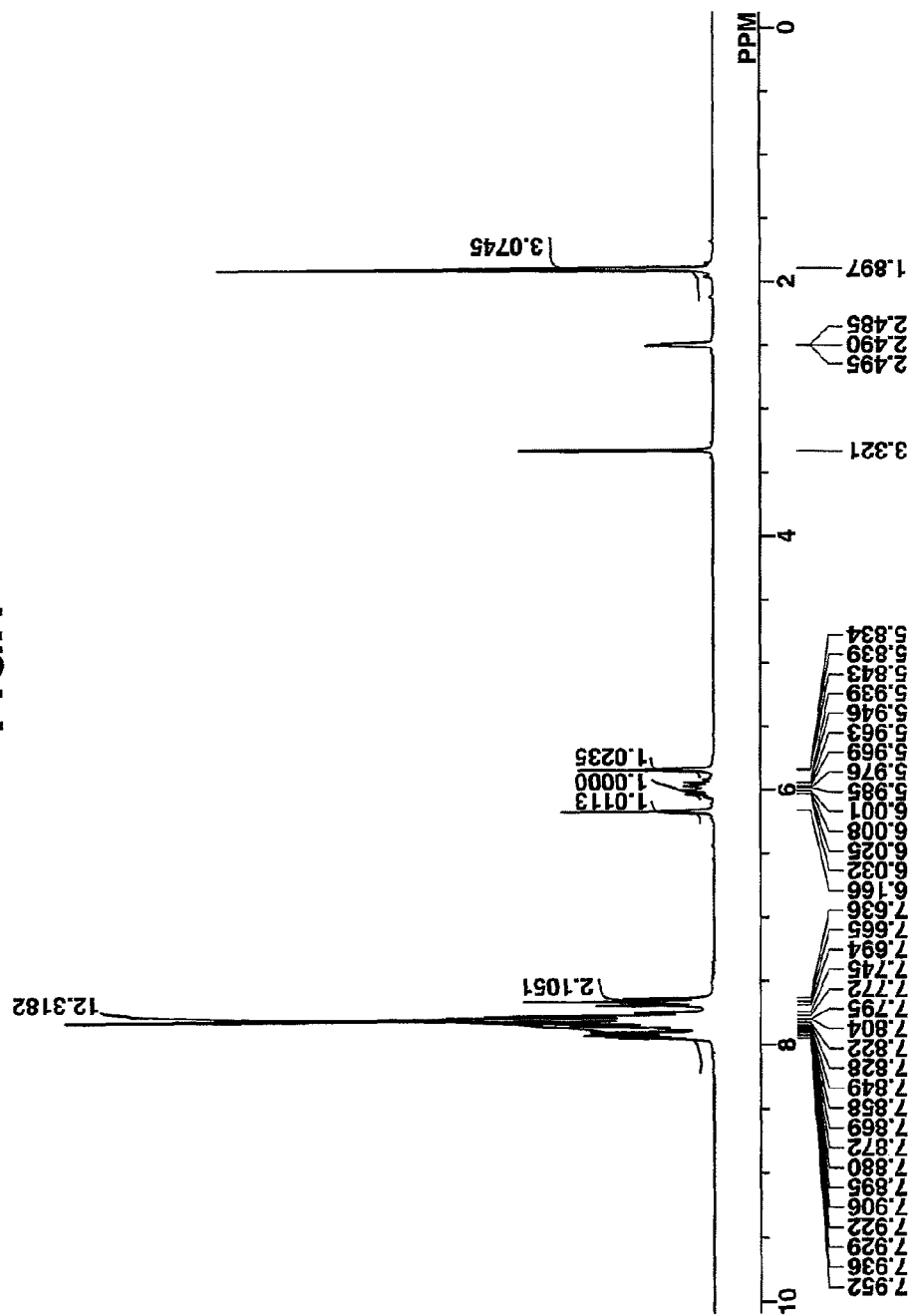
FIG. 1 is a diagram showing the $^1$H-NMR spectrum of PAG-1 in Synthesis Example 5.

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group.

The acronym "PAG" stands for photoacid generator, "PEB" for post-exposure bake, and "LER" for line edge roughness.

The term "high-energy radiation" is intended to encompass ultraviolet (UV) radiation, deep UV, electron beam (EB), extreme ultraviolet (EUV), x-ray, excimer laser, □-ray and synchrotron radiation.

Sulfonium Salt

In a first embodiment, the invention provides a sulfonium salt resulting from exchange between an ammonium salt having a polymerizable anion and a sulfonium salt having a 4-fluorophenyl group.

Described below is the synthesis of the sulfonium salt having the general formula (1). Notably, the well-known method such as JP-A 2008-133448 or JP-A 2009-263487 is not directly applicable to this synthesis. This is because in an attempt to produce 4-fluorophenylsulfonium 1,1,3,3,3-pentafluoro-2-hydroxypropane-1-sulfonate through hydrolysis/ alcoholysis of 4-fluorophenylsulfonium 2-acyloxy-1,1,3,3,3-pentafluoropropane-1-sulfonate according to the teaching of JP-A 2008-133448 or JP-A 2009-263487, hydrolysis/alcoholysis takes place on the 4-fluorophenylsulfonium cation whereby the cation is decomposed into a 4-hydroxyphenylsulfonium or 4-alkoxyphenylsulfonium cation.

The outline of the synthesis method is shown below.

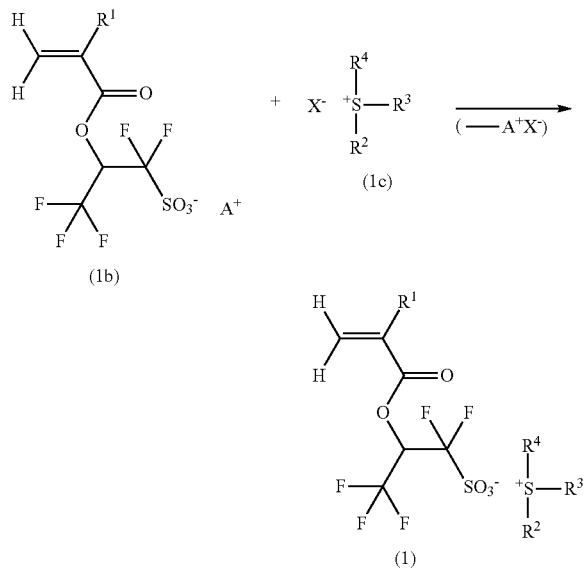

Herein, $R^1$ is hydrogen, fluorine, methyl or trifluoromethyl. $R^2$, $R^3$, and $R^4$ are each independently a substituted or unsubstituted, straight or branched $C_1$-$C_{10}$ alkyl, alkenyl or oxoalkyl group, a substituted or unsubstituted $C_6$-$C_{18}$ aryl, aralkyl or aryloxoalkyl group, or 4-fluorophenyl group, any two of $R^2$, $R^3$, and $R^4$ may bond together to form a ring with the sulfur atom, with the proviso that at least one of $R^2$, $R^3$, and $R^4$ is a 4-fluorophenyl group. $A^+$ is an ammonium cation or a $C_1$-$C_{16}$ primary, secondary, tertiary or quaternary ammonium cation. $X^-$ is a fluoride ion, chloride ion, bromide ion, iodide ion or methyl sulfate.

In formula (1b), $A^+$ is as defined just above. Examples of the $C_1$-$C_{16}$ primary, secondary, tertiary or quaternary ammonium cation include methylammonium, ethylammonium, propylammonium, butylammonium, tert-butylammonium, diethylammonium, triethylammonium, tributylammonium, tetramethylammonium, tetabutylammonium, pyridinium, 2,6-rutidinium, anilinium, benzyltimethylammonium, and benzyltriethylammonium, but are not limited thereto as long as an exchange with a 4-fluorophenylsulfonium salt is possible. Of these, triethylammonium and benzyltrimethylammonium are preferred for ease of handling such as organic solvent solubility and ease of ion exchange to be described later.

In formula (1c), $X^-$ is a fluoride ion, chloride ion, bromide ion, iodide ion or methyl sulfate, with chloride ion and methyl sulfate being preferred.

In formula (1b) and (1), $R^1$ is hydrogen, fluorine, methyl or trifluoromethyl, with hydrogen and methyl being preferred. $R^2$, $R^3$, and $R^4$ are each independently a substituted or unsubstituted, straight or branched $C_1$-$C_{10}$ alkyl, alkenyl or oxoalkyl group, a substituted or unsubstituted $C_6$-$C_{18}$ aryl, aralkyl or aryloxoalkyl group, or 4-fluorophenyl group. Suitable alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Suitable alkenyl groups include vinyl, allyl, propenyl, butenyl, hexenyl, and cyclohexenyl. Suitable oxoalkyl groups include 2-oxocyclopentyl, 2-oxocyclohexyl, 2-oxopropyl, 2-oxoethyl, 2-cyclopentyl-2-oxoethyl, 2-cyclohexyl-2-oxoethyl, and 2-(4-methylcyclohexyl)-2-oxoethyl. Suitable aryl groups include 4-fluorophenyl, phenyl, naphthyl and thienyl, as well as 4-hydroxyphenyl, alkoxyphenyl groups such as 4-methoxyphenyl, 3-methoxyphenyl, 2-methoxyphenyl, 4-ethoxyphenyl, 4-tert-butoxyphenyl, and 3-tert-butoxyphenyl, alkylphenyl groups such as 2-methylphenyl, 3-methylphenyl, 4-methylphenyl, 4-ethylphenyl, 4-tert-butylphenyl, 4-n-butylphenyl, and 2,4-dimethylphenyl, alkylnaphthyl groups such as methylnaphthyl and ethylnaphthyl, alkoxynaphthyl groups such as methoxynaphthyl and ethoxynaphthyl, dialkylnaphthyl groups such as dimethylnaphthyl and diethylnaphthyl, and dialkoxynaphthyl groups such as dimethoxynaphthyl and diethoxynaphthyl. Suitable aralkyl groups include benzyl, 1-phenylethyl, and 2-phenylethyl. Suitable aryloxoalkyl groups include 2-aryl-2-oxoethyl groups such as 2-phenyl-2-oxoethyl, 2-(1-naphthyl)-2-oxoethyl, and 2-(2-naphthyl)-2-oxoethyl. At least one of $R^2$, $R^3$, and $R^4$ is 4-fluorophenyl. When any two of $R^2$, $R^3$, and $R^4$ bond together to form a cyclic structure with the sulfur atom, suitable cyclic structures are shown below.

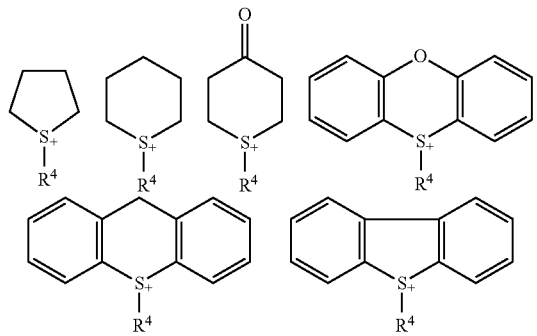

Exclusively in these formulae, $R^4$ is 4-fluorophenyl.

Illustrative of the sulfonium cation are 4-fluorophenyldiphenylsulfonium, bis(4-fluorophenyl)phenylsulfonium, tris(4-fluorophenyl)sulfonium, 4-fluorophenyldi(4-methylphenyl)sulfonium, bis(4-fluorophenyl)(4-methylphenyl)sulfonium, 4-fluorophenyldi(4-(1,1-dimethylethyl)phenyl)sulfonium, bis(4-fluorophenyl)(4-(1,1-dimethylethyl)phenyl)sulfonium, 4-fluorophenylbis(4-hydroxyphenyl)sulfonium, bis(4-fluorophenyl)-4-hydroxyphenylsulfonium, tris(4-fluorophenyl)sulfonium, 4-tert-butoxyphenylbis(4-fluorophenyl)sulfonium, bis(4-tert-butoxyphenyl)-4-fluorophenylsulfonium, (4-fluorophenyl)bis(4-dimethylaminophenyl)sulfonium, bis(4-fluorophenyl)(4-hydroxy-3,5-dimethylphenyl)sulfonium, 4-fluorophenyldimethylsulfonium, 2-oxo-2-(4-fluorophenyl)ethylthiacyclopentanium, 4-fluoronaphth-1-yltetahydrothiophenium, and 10-(4-fluorophenyl)phenoxathiinium. Since the so-called alkylsulfonium salts have problems like low thermal stability and high reactivity with nucleophilic reagents, preference is given to 4-fluorophenyldiphenylsulfonium, bis(4-fluorophenyl)phenylsulfonium, tris(4-fluorophenyl)sulfonium, 4-fluorophenyldi(4-methylphenyl)sulfonium, and 10-(4-fluorophenyl)phenoxathiinium.

Now the synthesis method is described in detail.

(1) Preparation of Sulfonic Acid Anion: Synthesis of (1b)

First, an aliphatic or aromatic carboxylic acid ester of 1,1,3,3,3-pentafluoropropen-2-yl, typically 1,1,3,3,3-pentafluoropropen-2-yl benzoate, which was developed by Nakai et al. using 1,1,1,3,3,3-hexafluoro-2-propanol as the starting reactant, is reacted with sodium hydrogen sulfite or sodium sulfite in a solvent such as water or alcohol or a mixture thereof in the presence of a radical initiator such as azobisisobutyronitrile or benzoyl peroxide, forming a corresponding 1,1,3,3,3-pentafluoro-2-acyloxypropanesulfonic acid salt or 1,1,3,3,3-pentafluoro-2-arenecarbonyloxypropane-sulfonic acid salt. This salt is salt-exchanged with an ammonium salt such as benzyltrimethylammonium bromide or triethylammonium chloride, obtaining an ammonium salt.

The ammonium salt, for example, benzyltrimethylammonium 1,1,3,3,3-pentafluoro-2-acyloxypropanesulfonate or benzyltrimethylammonium 1,1,3,3,3-pentafluoro-2-arenecarbonyloxypropanesulfonate is hydrolyzed with a base such as sodium hydroxide, and neutralized with an acid, obtaining benzyltrimethylammonium 1,1,3,3,3-pentafluoro-2-hydroxypropanesulfonate. Although the reaction to synthesize the polymerizable anion readily takes place by the well-known method, the reaction is preferably carried out by dissolving the intermediate in a solvent (e.g., methylene chloride, tetrahydrofuran or acetonitrile), and sequentially or simultaneously adding a base (e.g., triethylamine, pyridine or 4-dimethylaminopyridine) and an acid chloride or acid anhydride (e.g., acryloyl chloride, acrylic anhydride, methacryloyl chloride, methacrylic anhydride, 2-fluoroacryloyl chloride, 2-fluoroacrylic anhydride, □,□,□-trifluoromethacryloyl chloride, or □,□,□-trifluoromethacrylic anhydride) thereto, and optionally heating or cooling.

(2) Preparation of Cation: Synthesis of (1c)

In one exemplary procedure, 4-fluorophenyldiphenyl sulfonium chloride or analogs may be synthesized by the standard technique using diphenyl sulfoxide, trimethylsilyl chloride, and 4-fluorophenyl Grignard reagent. With respect to this synthesis, reference may be made to JP 4175115. Also, tris(4-fluorophenyl)sulfonium halide may be prepared from a Grignard reagent as described in JP 3063615 and JP 4207623.

Examples of the diaryl sulfoxide which can be used herein include bis(4-methylphenyl) sulfoxide, bis(4-fluorophenyl) sulfoxide, and phenoxathiin-5-oxide as well as diphenyl sulfoxide. Examples of the aryl Grignard reagent which can be used herein include phenyl Grignard reagent and 4-methylphenyl Grignard reagent as well as 4-fluorophenyl Grignard reagent.

(3) Preparation of Sulfonium Salt: Synthesis of (1)

The sulfonium salt (1) can be prepared from the ammonium salt having a polymerizable unit (1b) and the sulfonium salt having a fluorophenyl group (1c) by an ordinary salt exchange method. Specifically, the desired salt may be obtained by mixing the starting salts in an organic solvent (e.g., dichloromethane, ethyl acetate or methyl isobutyl ketone) or water, separating an organic layer, washing the organic layer with water, concentrating the organic layer, and purifying by recrystallization or column chromatography.

Although the description is redundant, an attempt to obtain the intermediate from the currently available step such as hydrolysis or alcoholysis of 4-fluorophenyldiphenylsulfonium 1,1,3,3,3-pentafluoro-2-acyloxypropanesulfonate in an aqueous methanol solution is undesirable because the fluorine atom of the sulfonium cation undergoes nucleophilic displacement by hydroxide ion or alkoxide, resulting in a 4-hydroxyphenyldiphenylsulfonium salt or 4-alkoxyphenyldiphenylsulfonium salt. This problem can be solved by separately preparing an anion moiety having a polymerizable unit as described above and exchanging it with a 4-fluorophenyldiphenylsulfonium cation.

In a second embodiment, the invention provides a polymer comprising recurring units having the general formulae (1a), (2), and (3).

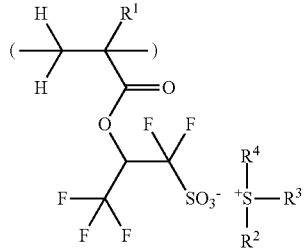

(1a)

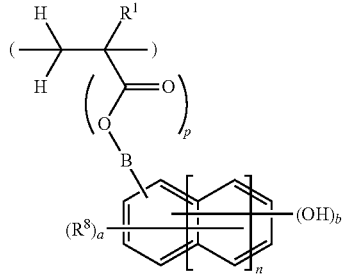

(2)

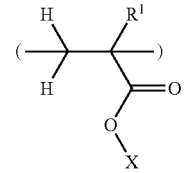

(3)

Herein $R^1$ is hydrogen, fluorine, methyl or trifluoromethyl. $R^2$, $R^3$, and $R^4$ are each independently a substituted or unsubstituted, straight or branched $C_1$-$C_{10}$ alkyl, alkenyl or oxoalkyl group, a substituted or unsubstituted $C_6$-$C_{18}$ aryl, aralkyl or aryloxoalkyl group, or 4-fluorophenyl group, any two of $R^2$, $R^3$, and $R^4$ may bond together to form a ring with the sulfur atom, with the proviso that at least one of $R^2$, $R^3$, and $R^4$ is 4-fluorophenyl, n is an integer of 0 to 2, $R^8$ is hydrogen or a $C_1$-$C_{10}$ alkyl group, p is 0 or 1, B is a single bond or a $C_1$-$C_{10}$ divalent organic group which may be substituted with an oxygen atom, a is an integer of 0 to 3, b is an integer of 1 to 3, and X is an acid labile group.

These recurring units are described in detail.

In formula (1a), $R^1$ is hydrogen, fluorine, methyl or trifluoromethyl, with hydrogen and methyl being preferred.

Examples of the recurring units having formula (1a) are given below.

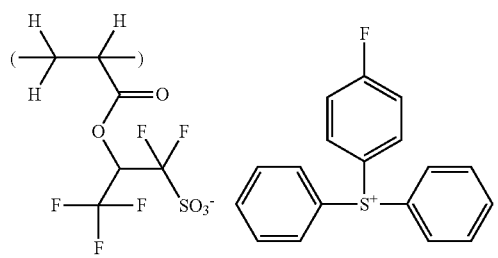

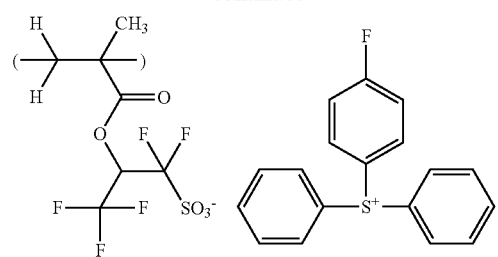
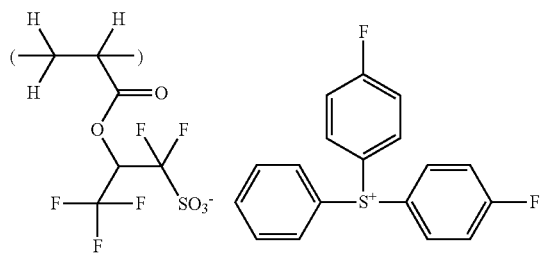
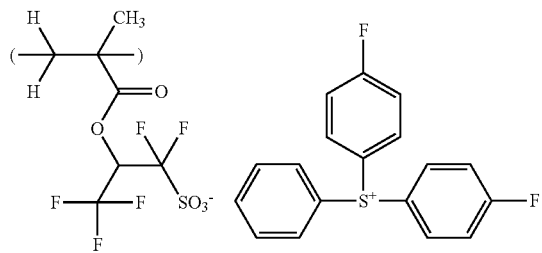
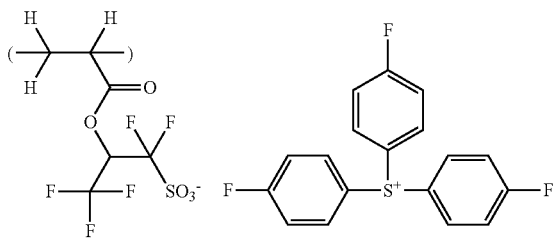
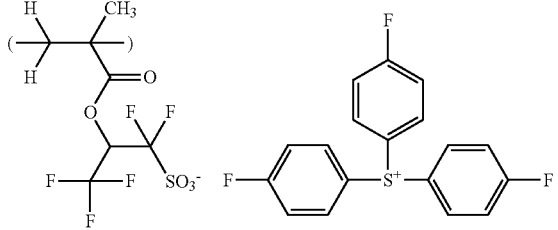
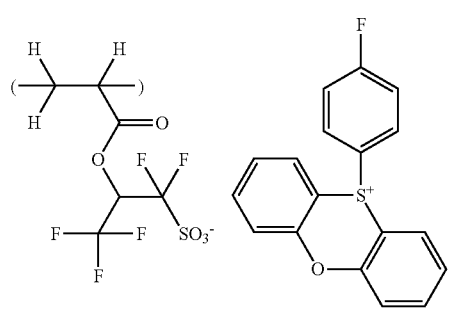

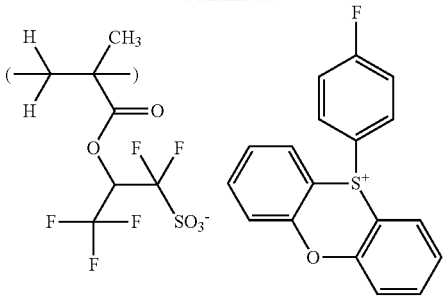
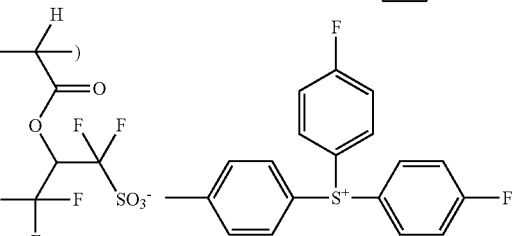
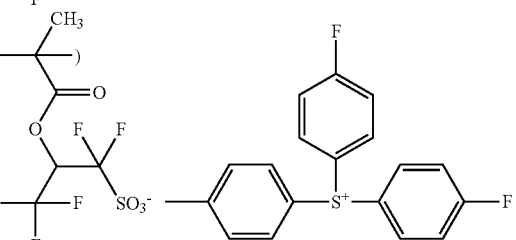
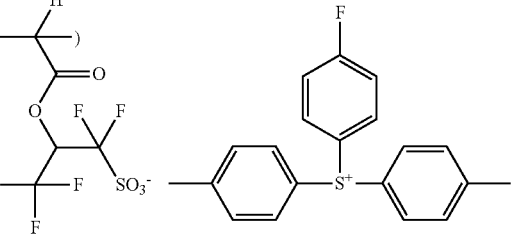
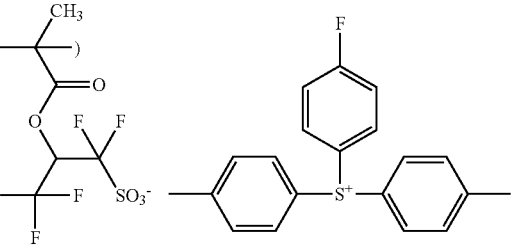

In formula (2), $R^1$ is hydrogen, fluorine, methyl or trifluoromethyl, with hydrogen and methyl being preferred. The subscript n is an integer of 0 to 2, preferably 1 or 2. $R^8$ is hydrogen or a $C_1$-$C_{10}$ alkyl group, preferably hydrogen or methyl. The subscript p is 0 or 1. B is a single bond or a $C_1$-$C_{10}$ divalent organic group which may be substituted with an oxygen atom, typically alkylene group such as methylene. Preferably B is a single bond or methylene. The subscript "a" is an integer of 0 to 3, preferably 0, and "b" is an integer of 1 to 3, preferably 1.

Examples of the recurring units having formula (2) are given below.

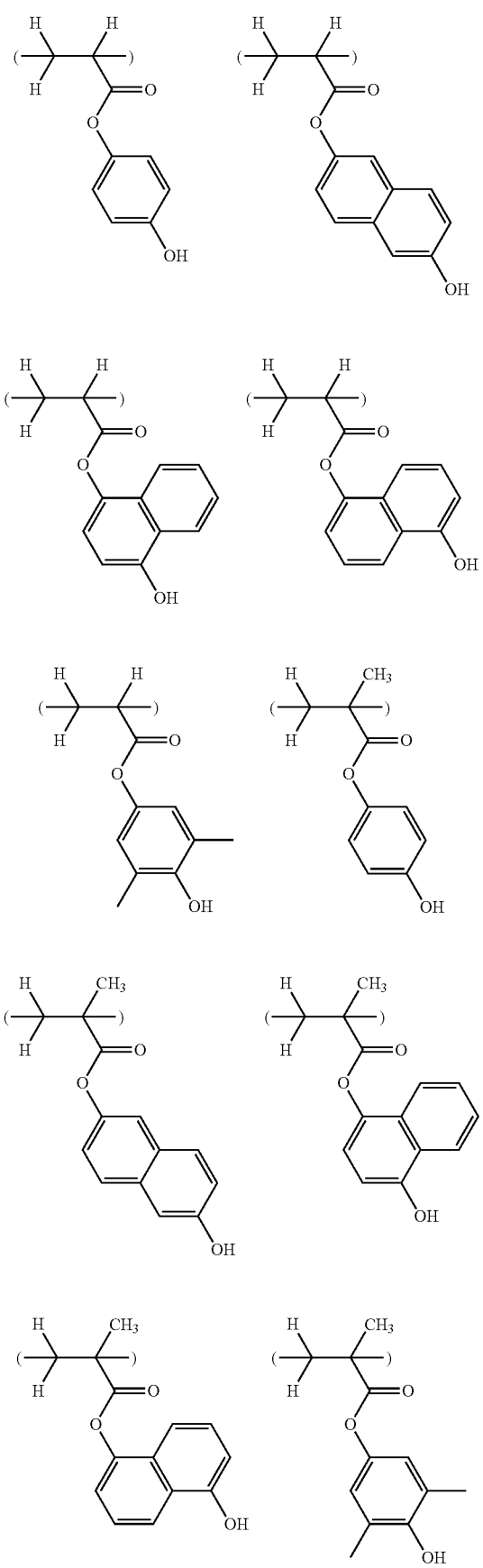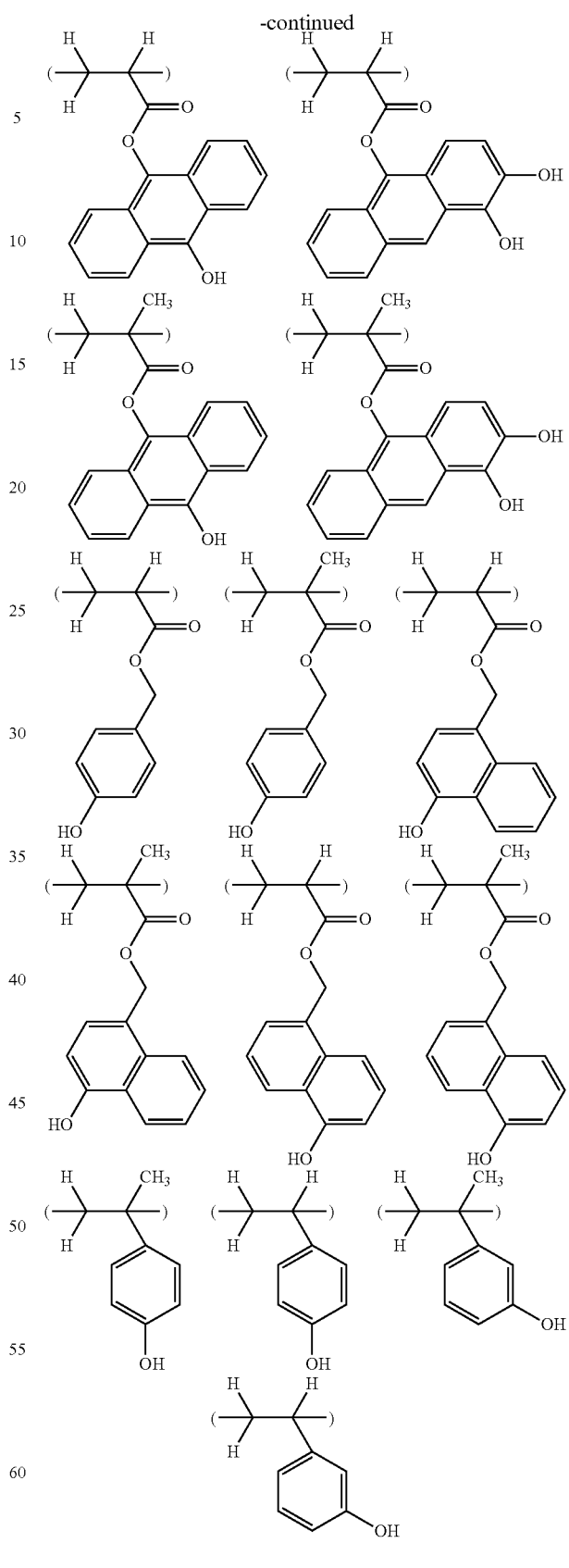
Under the action of an acid, a polymer comprising recurring units having formula (3) is decomposed to generate a carboxylic acid whereby it turns alkali soluble. X denotes an acid labile group. The acid labile group X may be selected from a variety of such groups, for example, groups of the following general formulae (L1) to (L4) and (L2-2), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

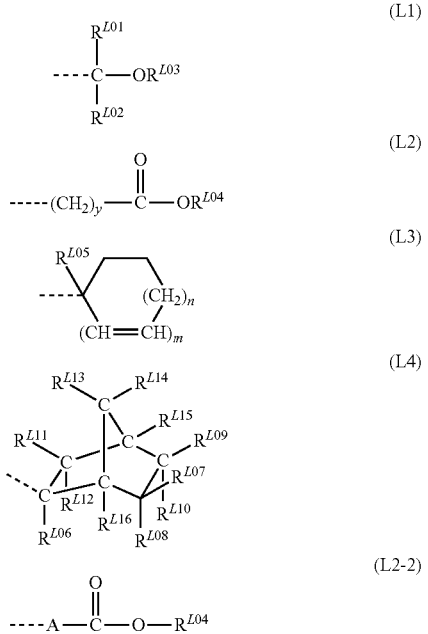

Herein and throughout the specification, the broken line denotes a valence bond.

In formula (L1), $R^{L01}$ and $R^{L02}$ are hydrogen or straight, branched or cyclic alkyl groups of 1 to 18 carbon atoms, preferably 1 to 10 carbon atoms, examples of which include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl and adamantyl. $R^{L03}$ is a monovalent hydrocarbon group of 1 to 18 carbon atoms, preferably 1 to 10 carbon atoms, which may contain a heteroatom such as oxygen, examples of which include straight, branched or cyclic alkyl groups and substituted forms of these groups in which some hydrogen atoms are replaced by hydroxyl, alkoxy, oxo, amino, alkylamino or the like. Exemplary substituted alkyl groups are illustrated below.

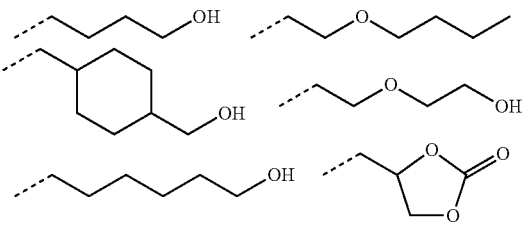

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. Each participant of $R^{L01}$, $R^{L02}$ and $R^{L03}$ is a straight or branched alkylene group of 1 to 18 carbon atoms, preferably 1 to 10 carbon atoms when they form a ring.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. In formula (L2), y is an integer of 0 to 6.

In formula (L2-2), $R^{L04}$ is as defined above, and a moiety of the formula:

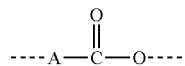

is selected from the following groups:

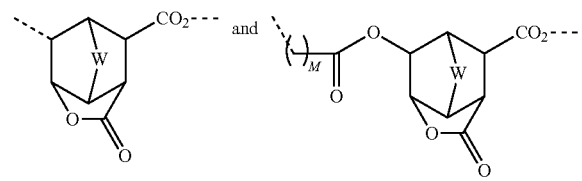

wherein the broken line denotes a valence bond, W is oxygen or $CH_2$, and M is an integer of 1 to 3.

In formula (L3), $R^{L05}$ is a substituted or unsubstituted, straight, branched or cyclic $C_1$-$C_8$ alkyl group or a substituted or unsubstituted $C_6$-$C_{20}$ aryl group. Examples of the optionally substituted alkyl groups include straight, branched or cyclic ones such as methyl, ethyl, propyl, isopropyl, n-butyl, sec-butyl, tert-butyl, tert-amyl, n-pentyl, n-hexyl, cyclopentyl, and cyclohexyl; and substituted forms of the foregoing in which some hydrogen atoms are replaced by hydroxyl, alkoxy, carboxy, alkoxycarbonyl, oxo, amino, alkylamino, cyano, mercapto, alkylthio, sulfo or other groups. Exemplary optionally substituted aryl groups are phenyl, methylphenyl, naphthyl, anthryl, phenanthryl, and pyrenyl. In formula (L3), m is 0 or 1, n is 0, 1, 2 or 3, and 2 m+n is equal to 2 or 3.

In formula (L4), $R^{L06}$ is a substituted or unsubstituted, straight, branched or cyclic $C_1$-$C_8$ alkyl group or a substituted or unsubstituted $C_6$-$C_{20}$ aryl group. Examples of these groups are the same as exemplified for $R^{L05}$. $R^{L07}$ to $R^{L16}$ each independently denote hydrogen or monovalent $C_1$-$C_{15}$ hydrocarbon groups. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of the foregoing in which some hydrogen atoms are replaced by hydroxyl, alkoxy, carboxy, alkoxycarbonyl, oxo, amino, alkylamino, cyano, mercapto, alkylthio, sulfo or other groups. Alternatively, two of $R^{L07}$ to $R^{L16}$ may bond together to form a ring with the carbon atom to which they are attached (for example, a pair of $R^{L07}$ and $R^{L08}$, $R^{L07}$ and $R^{L09}$, $R^{L07}$ and $R^{L10}$, $R^{L08}$ and $R^{L10}$, $R^{L09}$ and $R^{L10}$, $R^{L11}$ and $R^{L12}$, $R^{L13}$ and $R^{L14}$ or a similar pair). Each participant of $R^{L07}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, $R^{L14}$ and $R^{L15}$, or a similar pair).

Of the acid labile groups of formula (L1), the straight and branched ones are exemplified by the following groups.

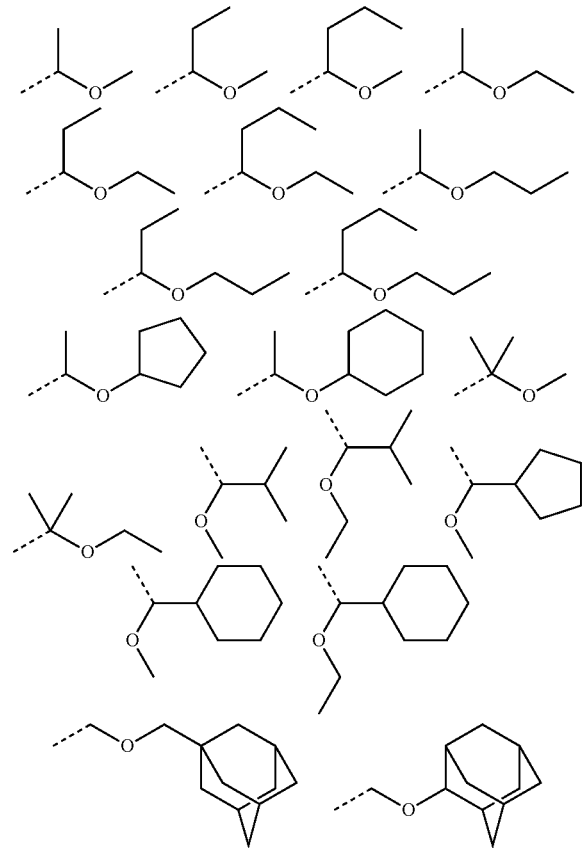

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Examples of the acid labile groups of formula (L2-2) include
9-(tert-butyloxycarbonyl)-5-oxo-4-oxatricyclo[4.2.1.0$^{3,7}$]-nonan-2-yl,
9-(tert-amyloxycarbonyl)-5-oxo-4-oxatricyclo[4.2.1.0$^{3,7}$]nonan-2-yl,
9-(2-(adamantan-1-yl)propan-2-yloxycarbonyl)-5-oxo-4-oxatricyclo[4.2.1.0$^{3,7}$]nonan-2-yl,
9-(1-ethylcyclopentyloxycarbonyl)-5-oxo-4-oxatricyclo-[4.2.1.0$^{3,7}$]nonan-2-yl,
9-(1-butylcyclopentyloxycarbonyl)-5-oxo-4-oxatricyclo-[4.2.1.0$^{3,7}$]nonan-2-yl,
9-(1-ethylcyclohexyloxycarbonyl)-5-oxo-4-oxatricyclo-[4.2.1.0$^{3,7}$]nonan-2-yl,
9-(1-butylcyclohexyloxycarbonyl)-5-oxo-4-oxatricyclo-[4.2.1.0$^{3,7}$]nonan-2-yl,
9-(2-methyl-2-adamantyloxycarbonyl)-5-oxo-4-oxatricyclo-[4.2.1.0$^{3,7}$]nonan-2-yl,
9-(2-ethyl-2-adamantyloxycarbonyl)-5-oxo-4-oxatricyclo-[4.2.1.0$^{3,7}$]nonan-2-yl,
9-(4-ethyltetracyclo[6.2.1.1$^{3,6}$.0$^{2,7}$]dodecan-4-yloxycarbonyl)-5-oxo-4-oxatricyclo[4.2.1.0$^{3,7}$]nonan-2-yl,
2-(9-(tert-butyloxycarbonyl)-5-oxo-4-oxatricyclo[4.2.1.0$^{3,7}$]-nonan-2-yloxy)-2-oxoethyl,
2-(9-(tert-amyloxycarbonyl)-5-oxo-4-oxatricyclo[4.2.1.0$^{3,7}$]-nonan-2-yloxy)-2-oxoethyl,
2-(9-(2-(adamantan-1-yl)propan-2-yloxycarbonyl)-5-oxo-4-oxatricyclo[4.2.1.0$^{3,7}$]nonan-2-yloxy)-2-oxoethyl,
2-(9-(1-ethylcyclopentyloxycarbonyl)-5-oxo-4-oxatricyclo-[4.2.1.0$^{3,7}$]nonan-2-yloxy)-2-oxoethyl,
2-(9-(1-butylcyclopentyloxycarbonyl)-5-oxo-4-oxatricyclo-[4.2.1.0$^{3,7}$]nonan-2-yloxy)-2-oxoethyl,
2-(9-(1-ethylcyclohexyloxycarbonyl)-5-oxo-4-oxatricyclo-[4.2.1.0$^{3,7}$]nonan-2-yloxy)-2-oxoethyl,
2-(9-(1-butylcyclohexyloxycarbonyl)-5-oxo-4-oxatricyclo-[4.2.1.0$^{3,7}$]nonan-2-yloxy)-2-oxoethyl,
2-(9-(2-methyl-2-adamantyloxycarbonyl)-5-oxo-4-oxatricyclo-[4.2.1.0$^{3,7}$]nonan-2-yloxy)-2-oxoethyl,
2-(9-(2-ethyl-2-adamantyloxycarbonyl)-5-oxo-4-oxatricyclo-[4.2.1.0$^{3,7}$]nonan-2-yloxy)-2-oxoethyl,
2-(9-(4-ethyltetracyclo[6.2.1.1$^{3,6}$.0$^{2,7}$]dodecan-4-yloxycarbonyl)-5-oxo-4-oxatricyclo[4.2.1.0$^{3,7}$]nonan-2-yloxy)-2-oxoethyl,
4-(9-(tert-butyloxycarbonyl)-5-oxo-4-oxatricyclo[4.2.1.0$^{3,7}$]-nonan-2-yloxy)-4-oxobutyl,
4-(9-(tert-amyloxycarbonyl)-5-oxo-4-oxatricyclo[4.2.1.0$^{3,7}$]-nonan-2-yloxy)-4-oxobutyl,
4-(9-(2-(adamantan-1-yl)propan-2-yloxycarbonyl)-5-oxo-4-oxatricyclo[4.2.1.0$^{3,7}$]nonan-2-yloxy)-4-oxobutyl,
4-(9-(1-ethylcyclopentyloxycarbonyl)-5-oxo-4-oxatricyclo-[4.2.1.0$^{3,7}$]nonan-2-yloxy)-4-oxobutyl,
4-(9-(1-butylcyclopentyloxycarbonyl)-5-oxo-4-oxatricyclo-[4.2.1.0$^{3,7}$]nonan-2-yloxy)-4-oxobutyl,
4-(9-(1-ethylcyclohexyloxycarbonyl)-5-oxo-4-oxatricyclo-[4.2.1.0$^{3,7}$]nonan-2-yloxy)-4-oxobutyl,
4-(9-(1-butylcyclohexyloxycarbonyl)-5-oxo-4-oxatricyclo-[4.2.1.0$^{3,7}$]nonan-2-yloxy)-4-oxobutyl,
4-(9-(2-methyl-2-adamantyloxycarbonyl)-5-oxo-4-oxatricyclo-[4.2.1.0$^{3,7}$]nonan-2-yloxy)-4-oxobutyl,
4-(9-(2-ethyl-2-adamantyloxycarbonyl)-5-oxo-4-oxatricyclo-[4.2.1.0$^{3,7}$]nonan-2-yloxy)-4-oxobutyl,
4-(9-(4-ethyltetracyclo[6.2.1.1$^{3,6}$.0$^{2,7}$]dodecan-4-yloxycarbonyl)-5-oxo-4-oxatricyclo[4.2.1.0$^{3,7}$]nonan-2-yloxy)-4-oxobutyl, etc.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Of the acid labile groups of formula (L4), those groups of the following formulae (L4-1) to (L4-4) are more preferred.

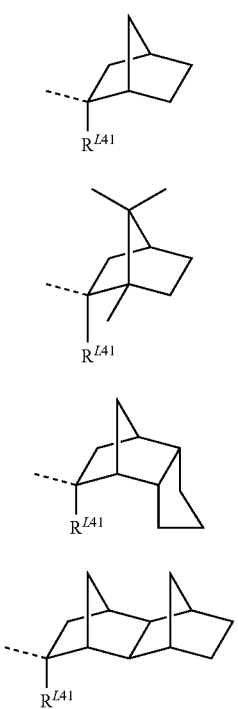

(L4-1)

(L4-2)

(L4-3)

(L4-4)

In formulae (L4-1) to (L4-4), the broken line denotes a bonding site and direction. $R^{L41}$ is each independently selected from monovalent hydrocarbon groups, typically straight, branched or cyclic $C_1$-$C_{10}$ alkyl groups, for example, methyl, ethyl, propyl, isopropyl, n-butyl, sec-butyl, tert-butyl, tert-amyl, n-pentyl, n-hexyl, cyclopentyl, and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

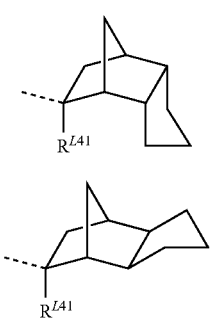

(L4-3-1)

(L4-3-2)

Similarly, the general formula (L4-4) represents one or a mixture of two or more selected from groups having the following general formulas (L4-4-1) to (L4-4-4).

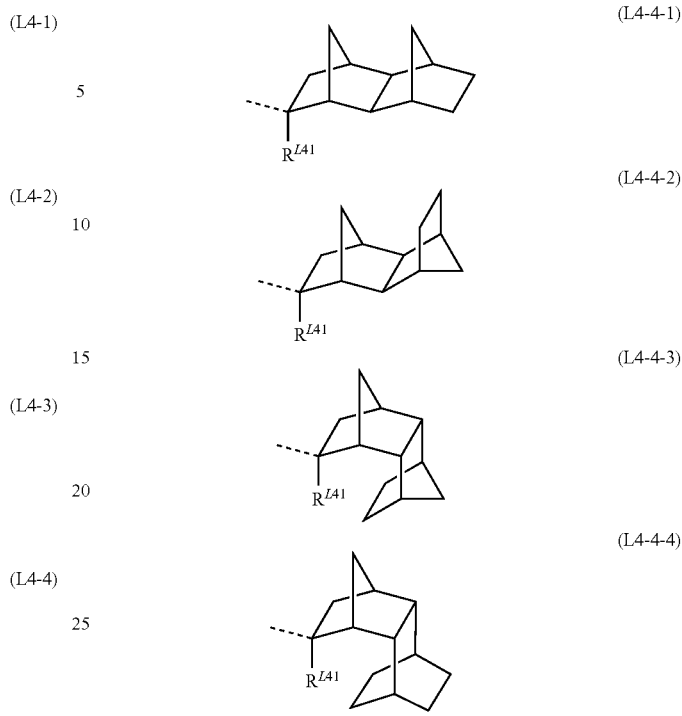

(L4-4-1)

(L4-4-2)

(L4-4-3)

(L4-4-4)

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1] heptane ring, which ensures high reactivity for acid catalyzed elimination reaction (see JP-A 2000-336121). In preparing these monomers having a tertiary exo-alkyl group of bicyclo [2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

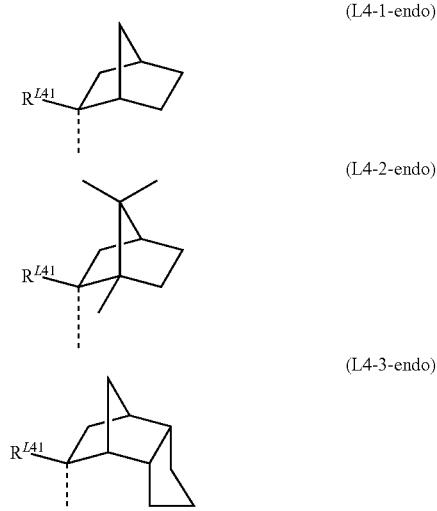

(L4-1-endo)

(L4-2-endo)

(L4-3-endo)

-continued

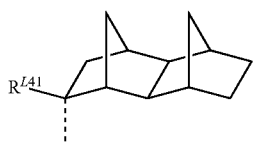
(L4-4-endo)

(See JP-A 2000-336121)

Illustrative examples of the acid labile group of formula (L4) are given below, but not limited thereto.

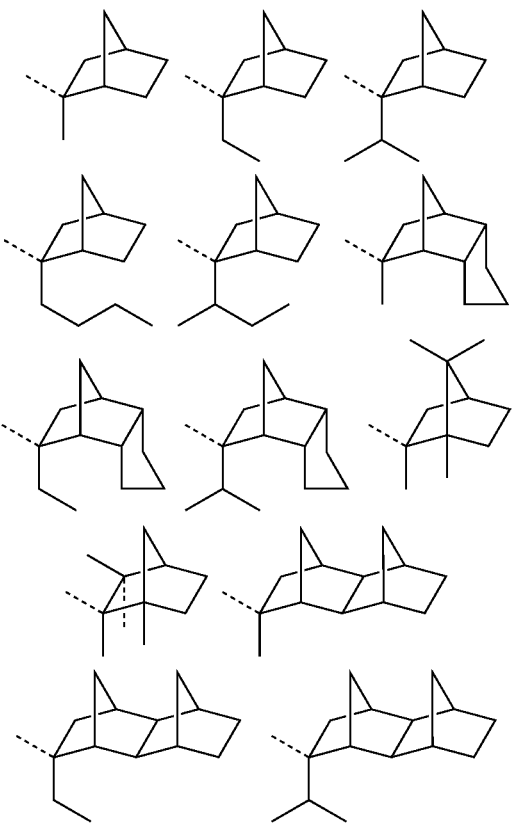

Examples of the tertiary $C_4$-$C_{20}$ alkyl, tri($C_1$-$C_6$-alkyl)silyl and $C_4$-$C_{20}$ oxoalkyl groups are as exemplified above for $R^{L04}$.

Illustrative, non-limiting examples of the recurring units of formula (3) are given below. Although only (meth)acrylates are illustrated, those which are separated by a divalent linking group of formula (L2) or (L2-2) are also useful.

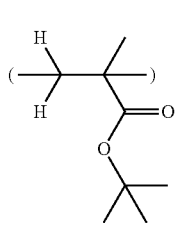 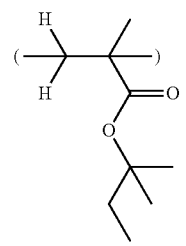

-continued

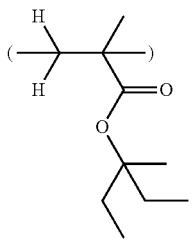 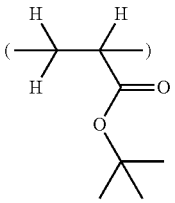

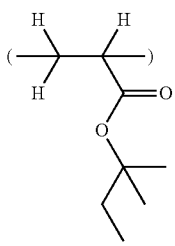 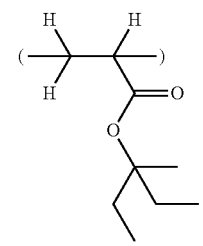

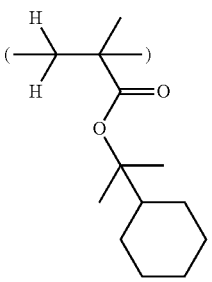 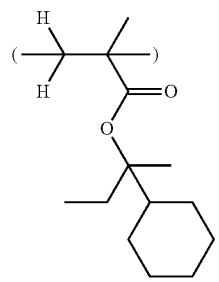

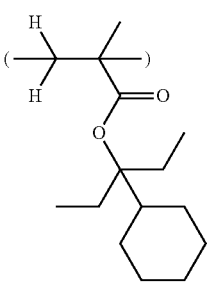 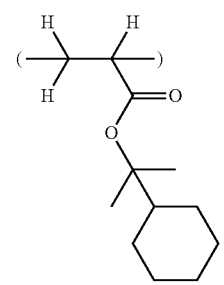

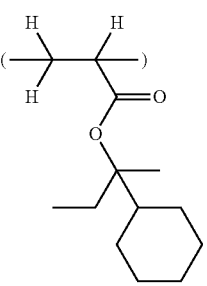 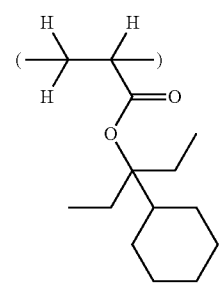

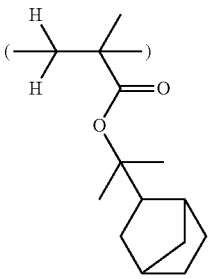 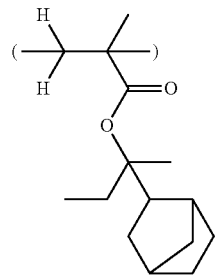

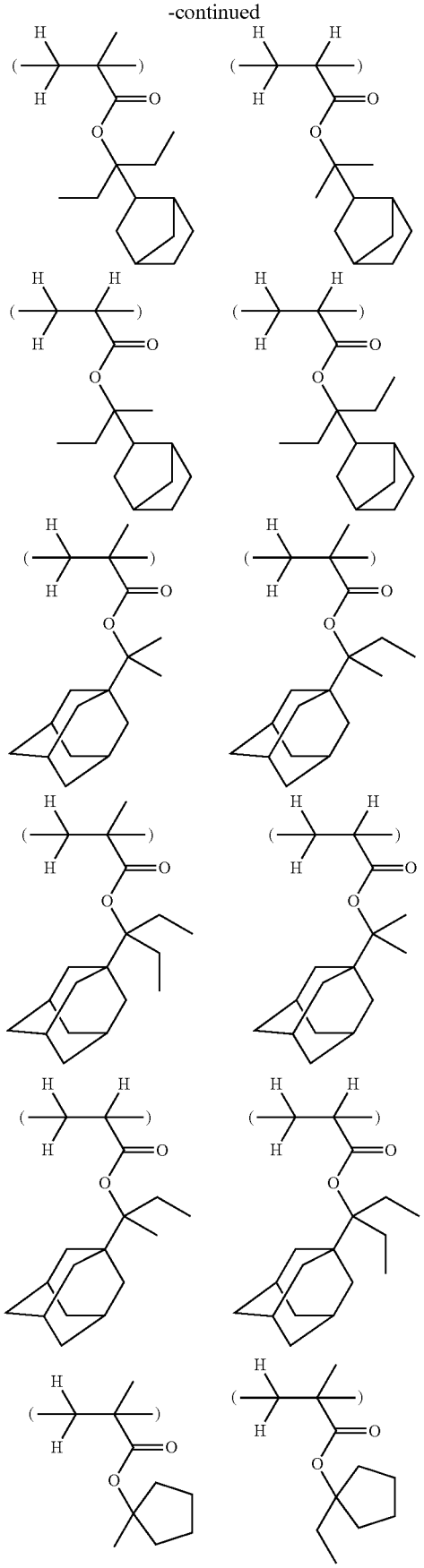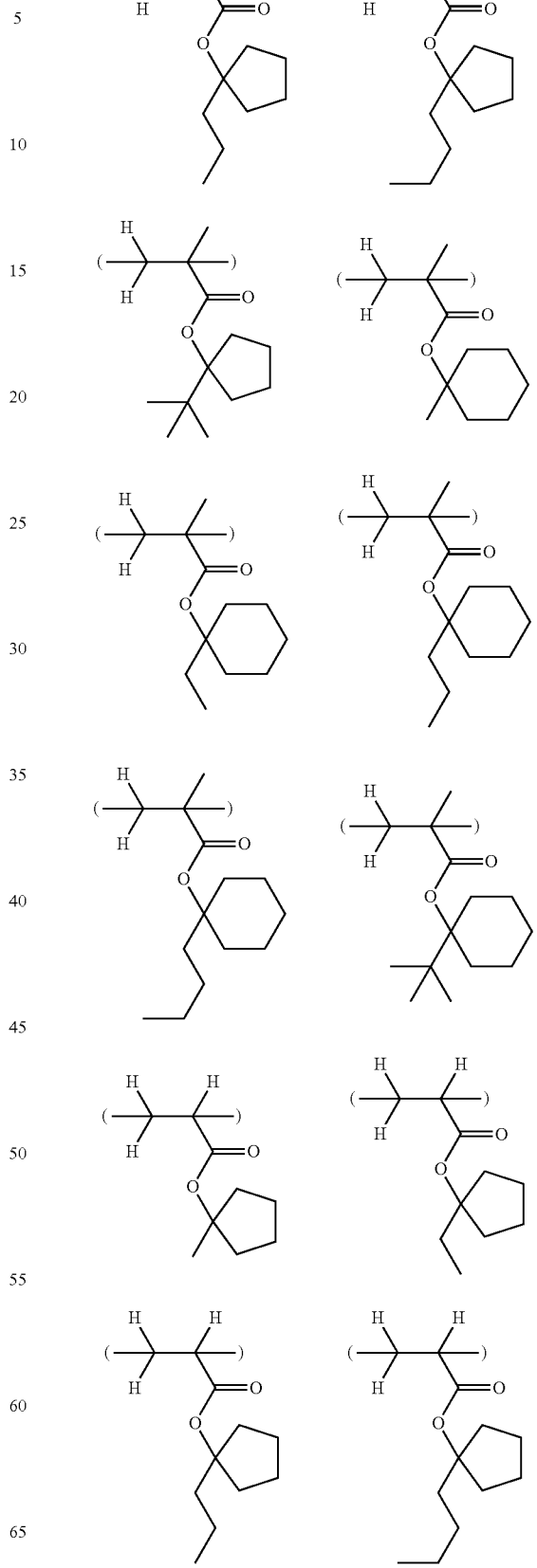

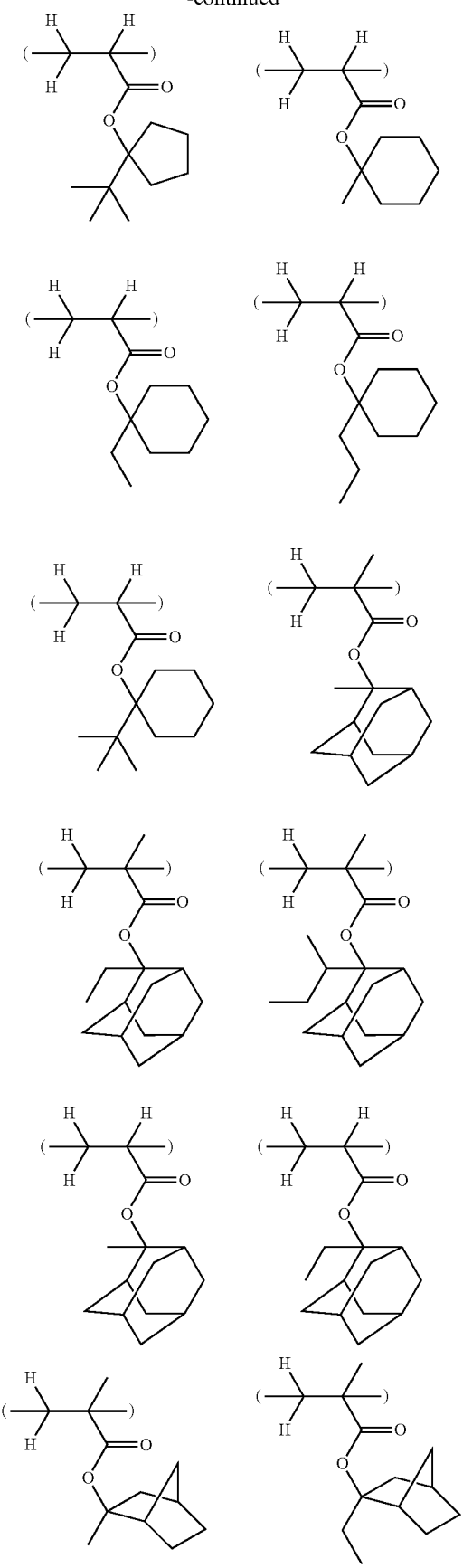
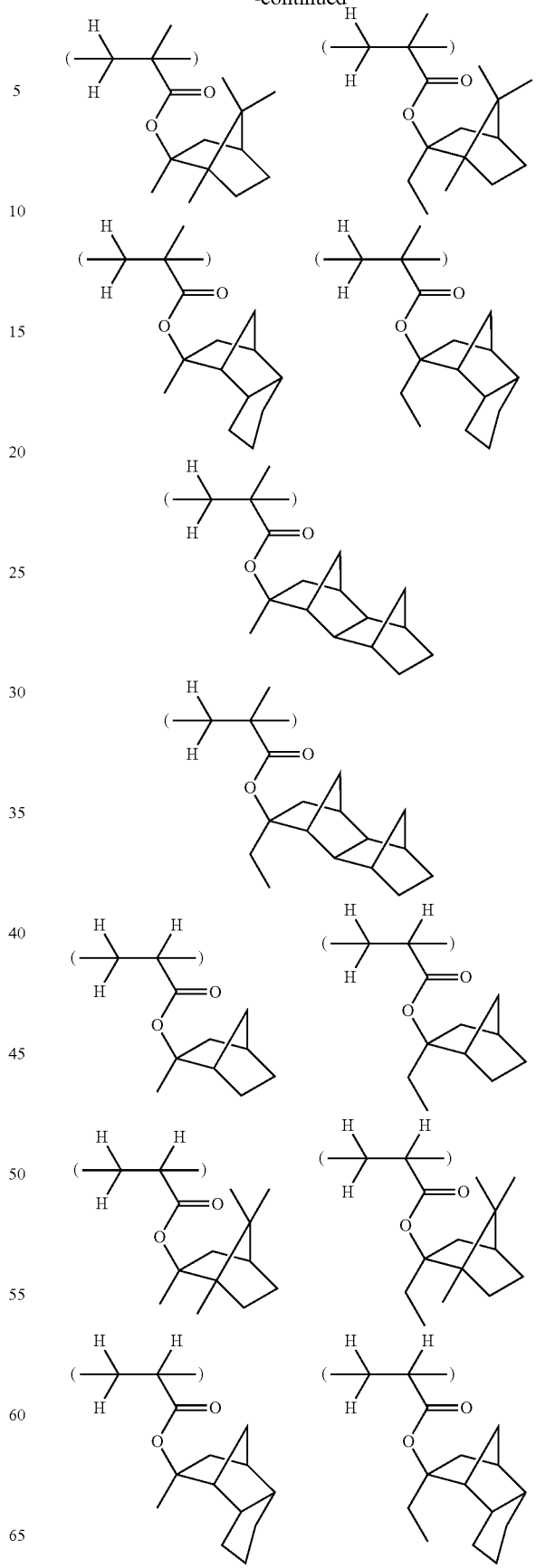

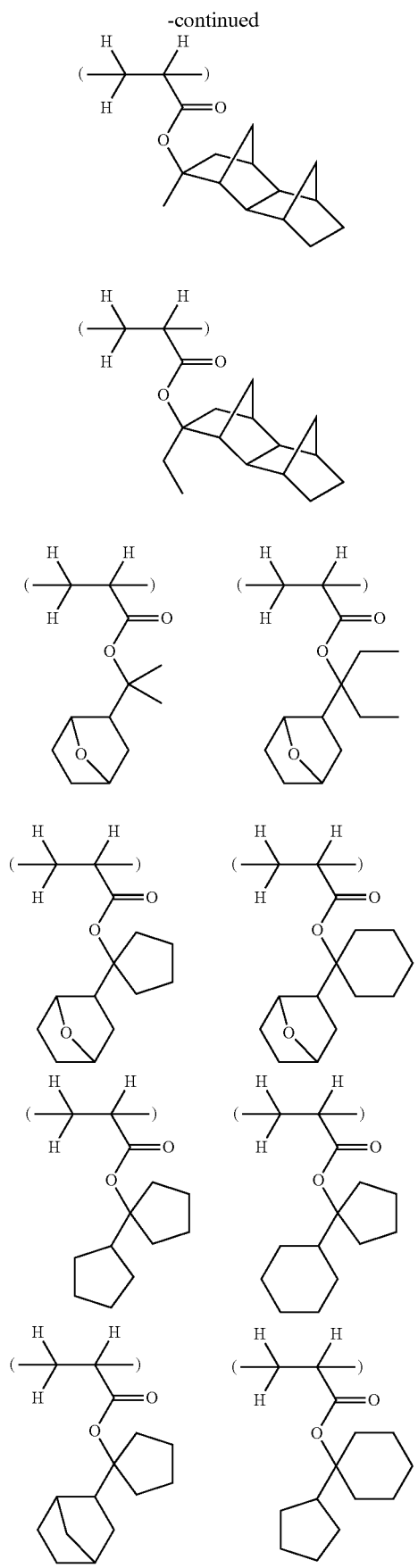
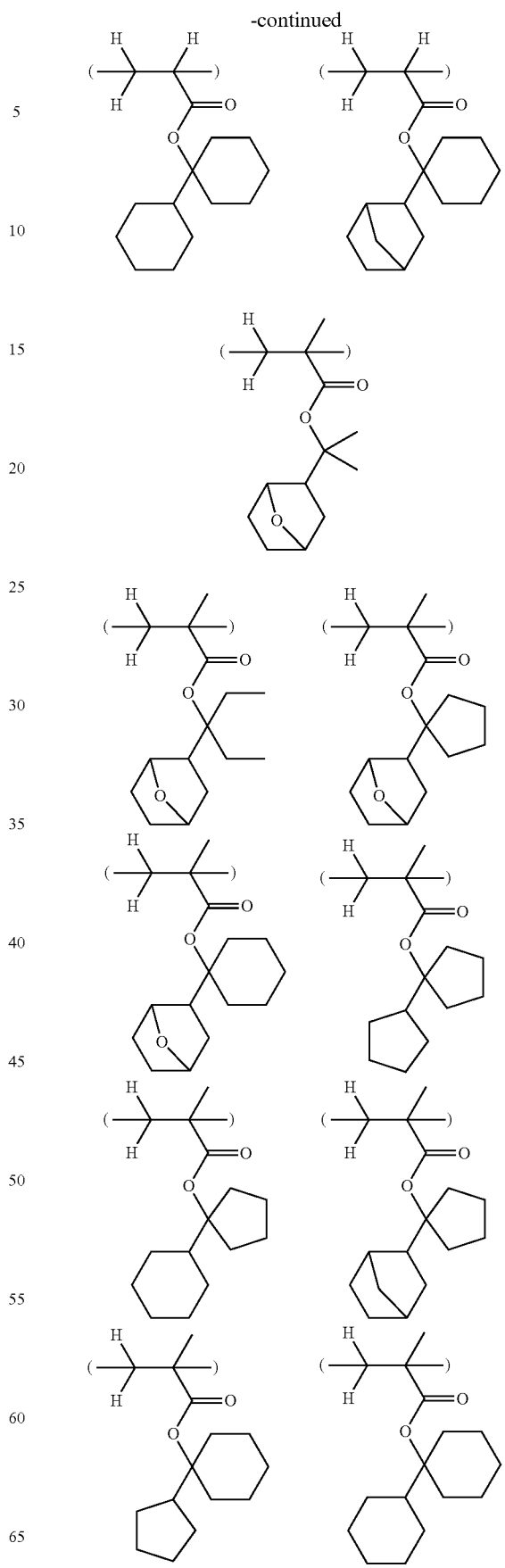

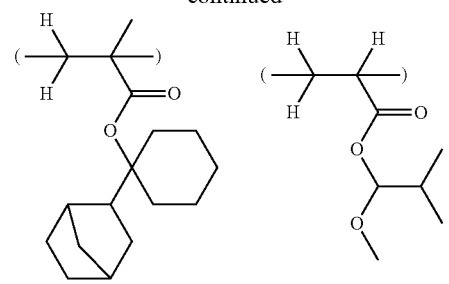
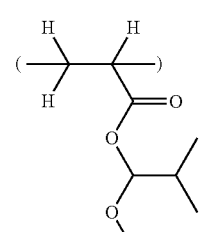
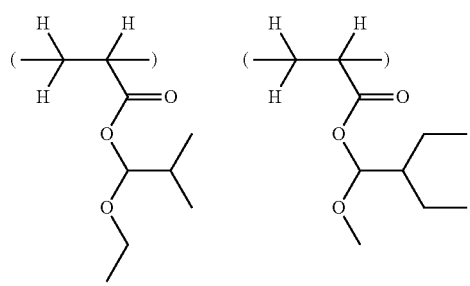
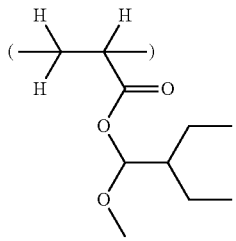
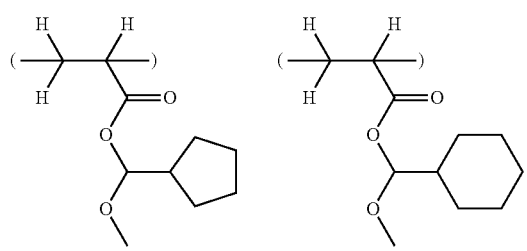
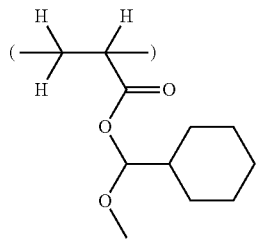
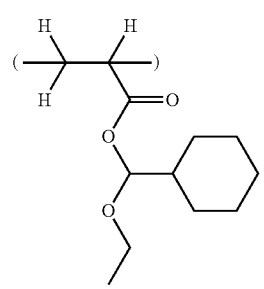
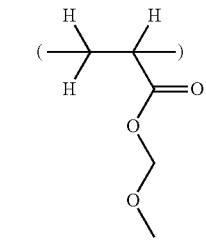
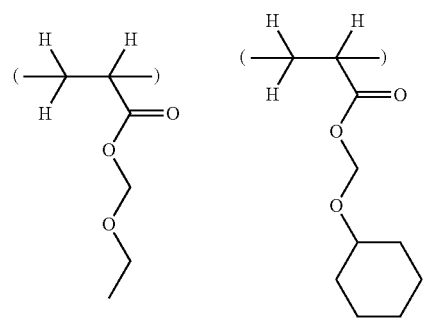
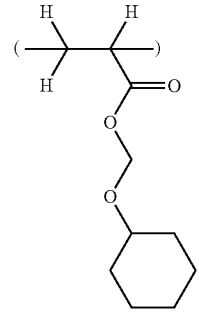
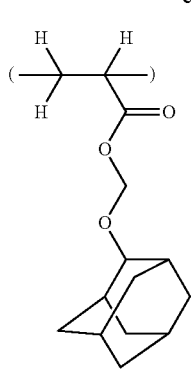
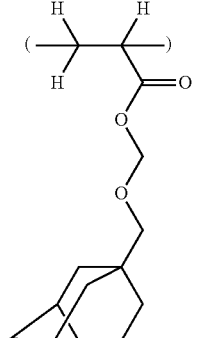
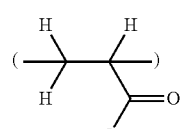
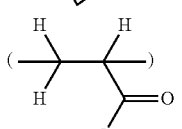
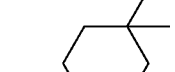
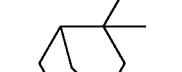
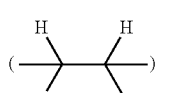
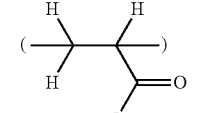
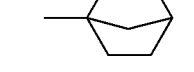
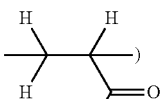
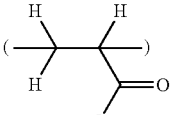
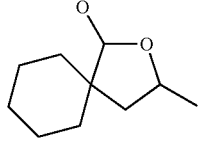
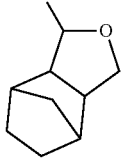

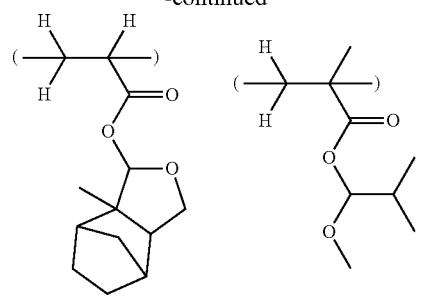
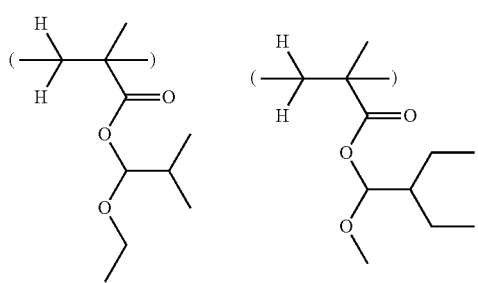
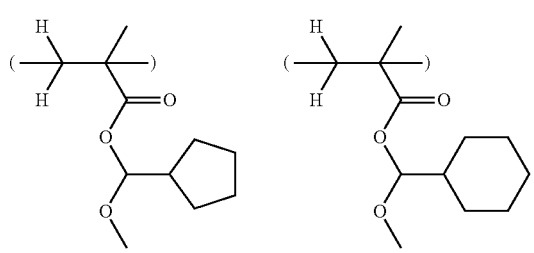
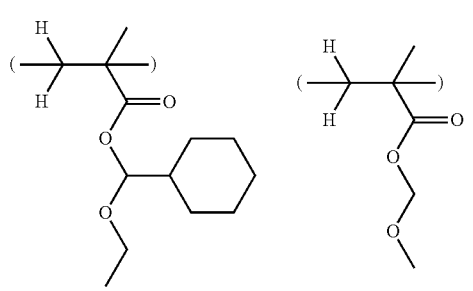
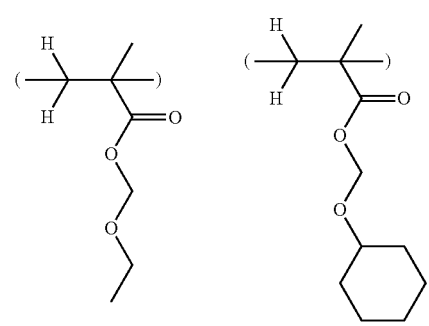
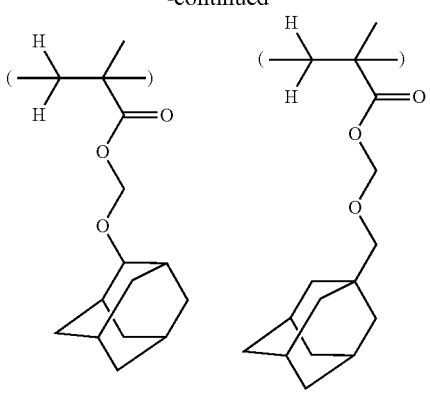
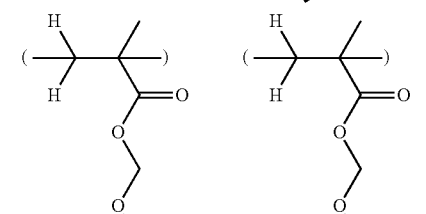
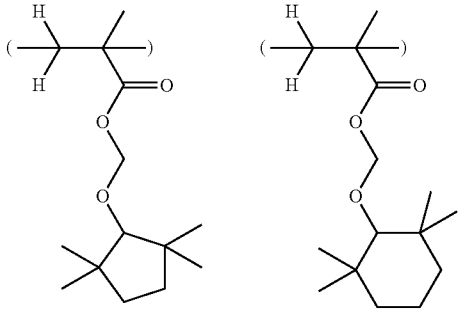
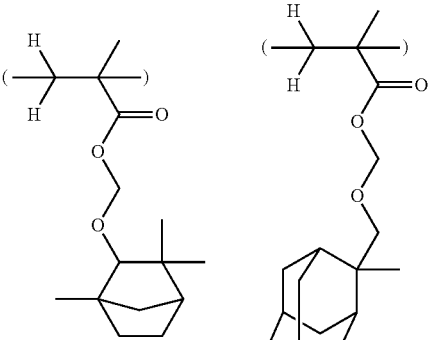
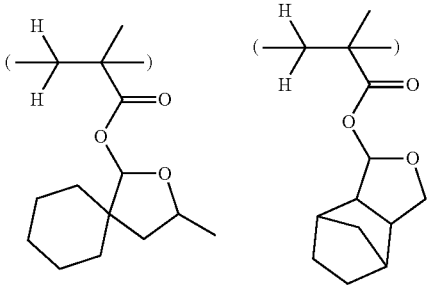

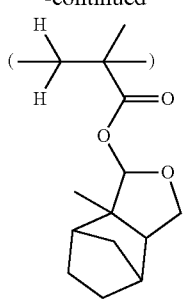

In addition to the recurring units having formulae (1a), (2), and (3), the polymer may further comprise recurring units of at least one type selected from the following general formulae (4), (5), and (6).

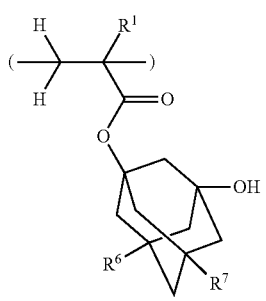 (4)

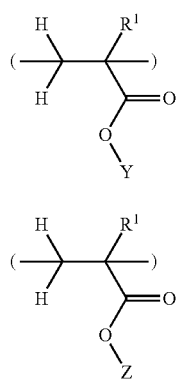 (5)

(6)

Herein $R^1$ is hydrogen, fluorine, methyl or trifluoromethyl, $R^6$ and $R^7$ are each independently hydrogen or hydroxyl, Y is a substituent group having lactone structure, Z is hydrogen, a $C_1$-$C_{15}$ fluoroalkyl group or $C_1$-$C_{15}$ fluoroalcohol-containing substituent group.

Examples of the recurring units having formula (4) are given below.

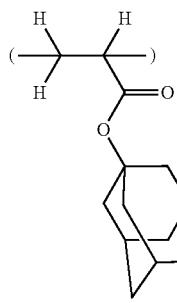 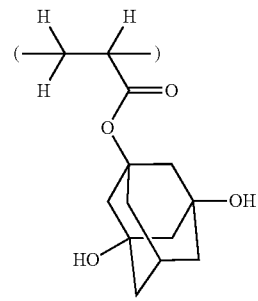

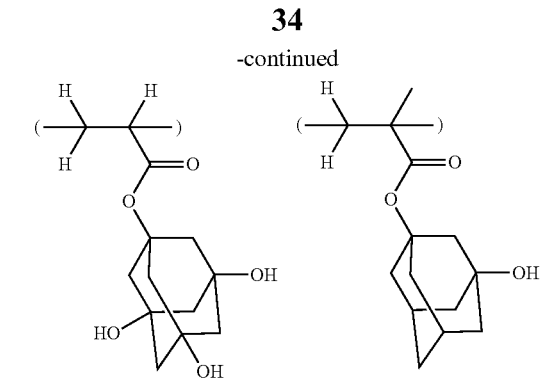

Examples of the recurring units having formula (5) are given below. Notably, recurring units having an acid labile group are also included. Examples of such units overlap the examples of formula (L2-2) illustrated above as the acid labile group, and they may be used either as the lactone unit or as the acid labile group-containing unit.

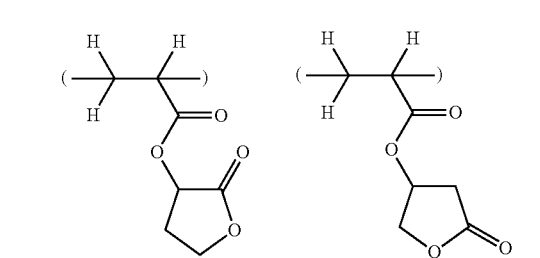

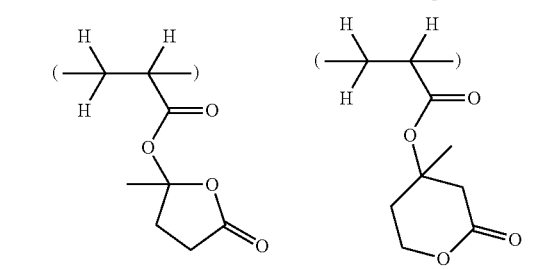

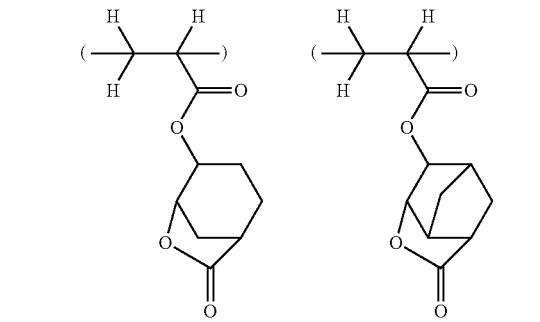

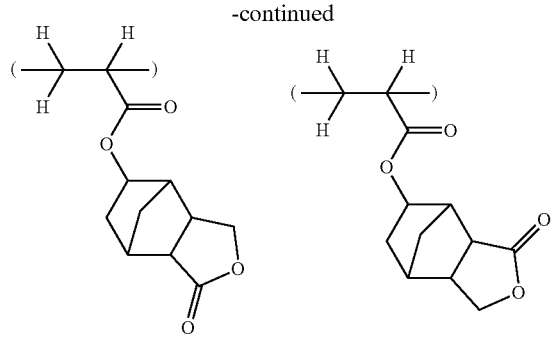
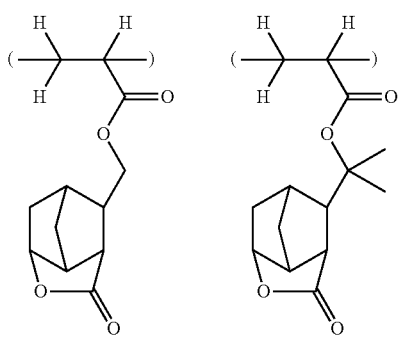
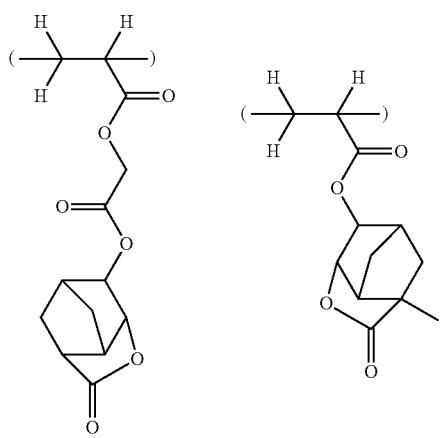
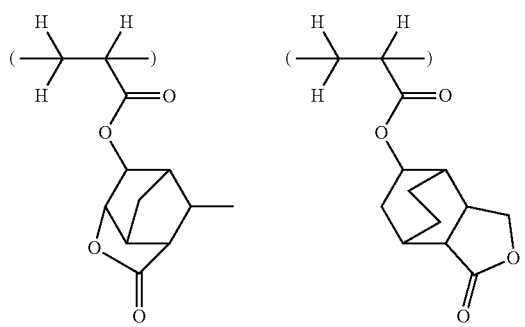
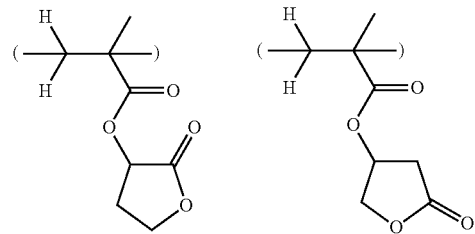
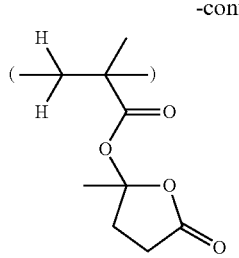
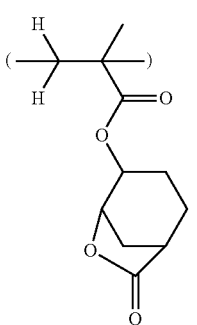
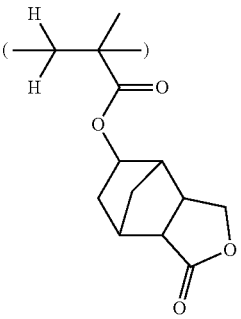
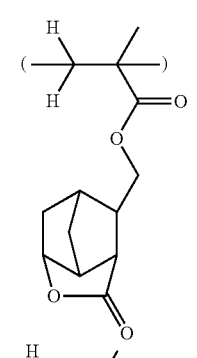

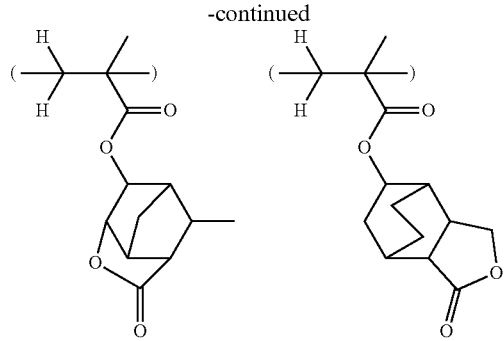
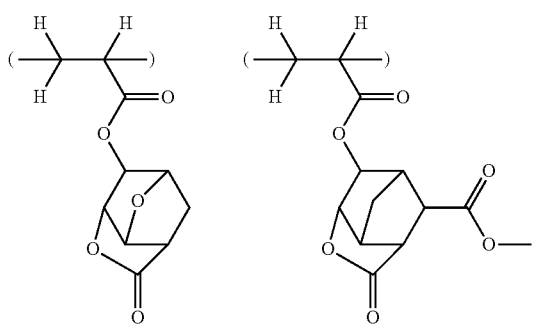
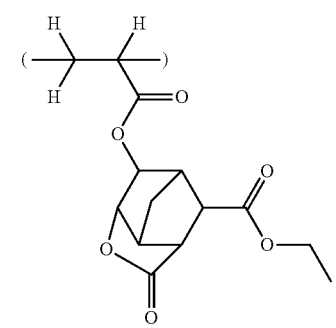
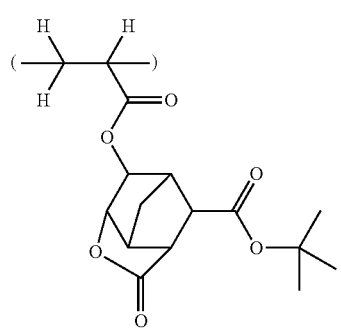
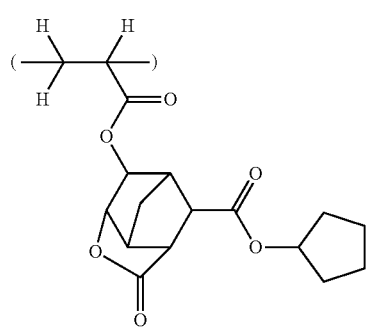
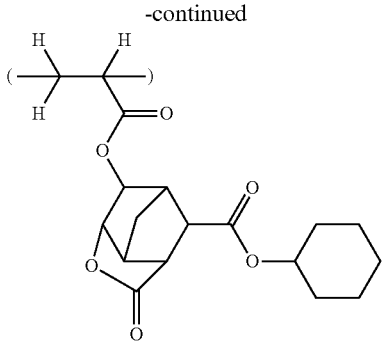
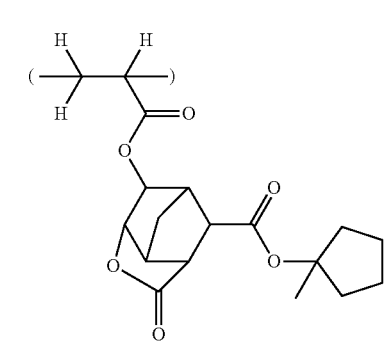
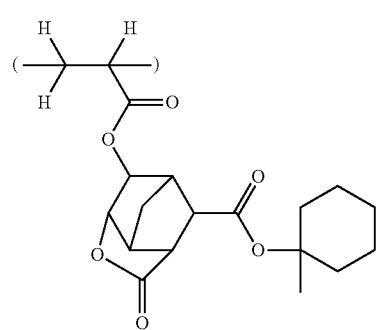
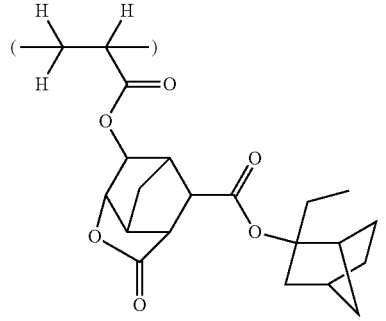

-continued
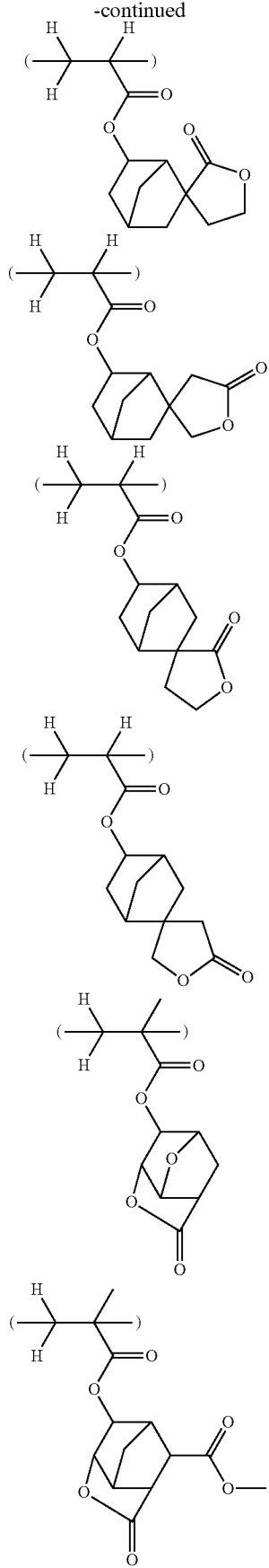
-continued
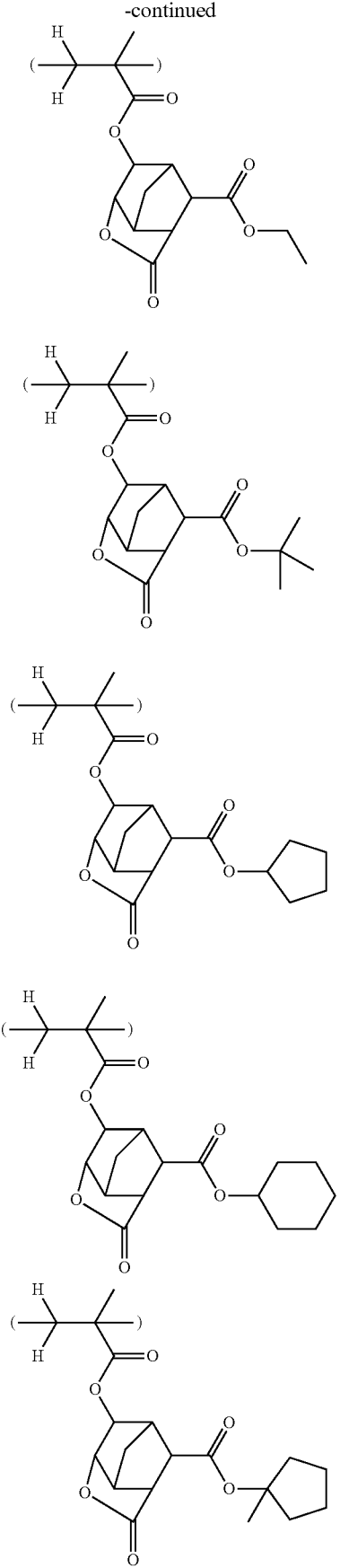

-continued

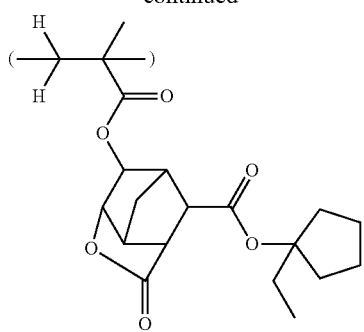

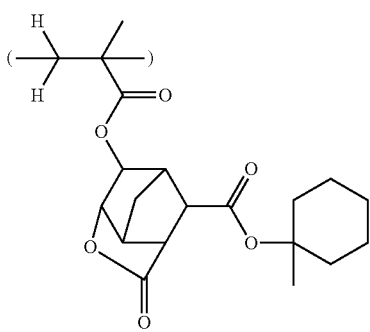

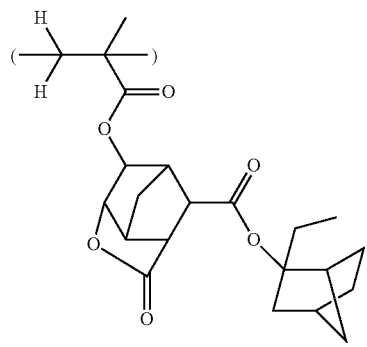

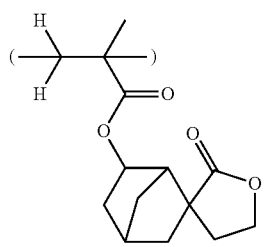

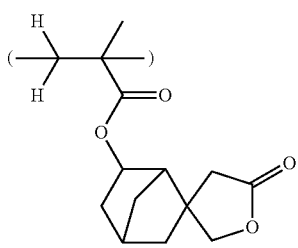

-continued

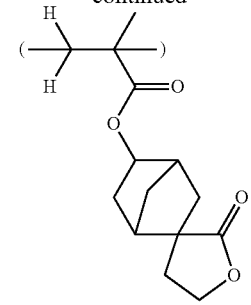

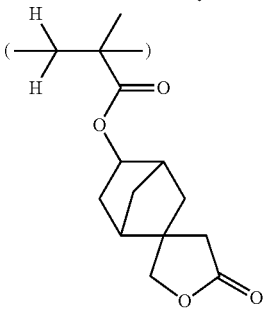

Also, units of the general formula (5L-1) may be advantageously used.

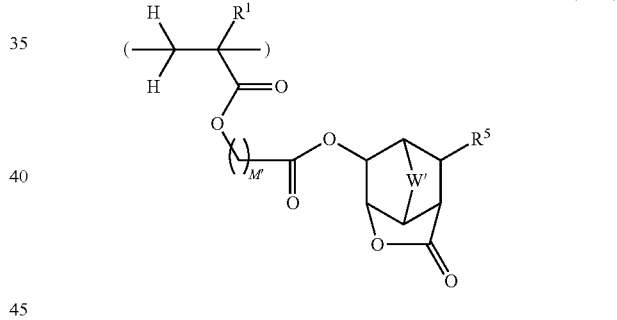

(5L-1)

In formula (5L-1), $R^1$ is hydrogen, fluorine, methyl or trifluoromethyl, and preferably methyl. $R^5$ is hydrogen, $CO_2R^{5'}$ or $CO_2X$ wherein $R^{5'}$ is hydrogen or a straight, branched or cyclic $C_1$-$C_{15}$ monovalent hydrocarbon group which may have halogen or oxygen. W' is $CH_2$, O or S. M' is an integer of 1 to 3.

Examples of $R^{5'}$ include hydrogen, methyl, ethyl, n-propyl, isopropyl, n-butyl, sec-butyl, isobutyl, tert-butyl, cyclopentyl, cyclohexyl, 1-methylcyclopentyl, 1-ethylcyclopentyl, 1-methylcyclohexyl, 1-ethylcyclohexyl, 2-ethylhexyl, n-octyl, 2-methylbicyclo[2.2.1]heptan-2-yl, 2-ethylbicyclo[2.2.1]heptan-2-yl, 2-methyladamantan-2-yl, 2-ethyladamantan-2-yl, 8-methyltricyclo[5.2.1.0$^{2,6}$]decan-8-yl, 8-ethyltricyclo[5.2.1.0$^{2,6}$]decan-8-yl, 4-methyltetracyclo[6.2.1.1$^{3,6}$.0$^{2,7}$]dodecan-4-yl, 4-ethyltetracyclo[6.2.1.1$^{3,6}$.0$^{2,7}$]dodecan-4-yl, methoxymethyl, ethoxymethyl, methoxyethyl, ethoxyethyl, and methoxyethoxyethyl, as well as the groups shown below.

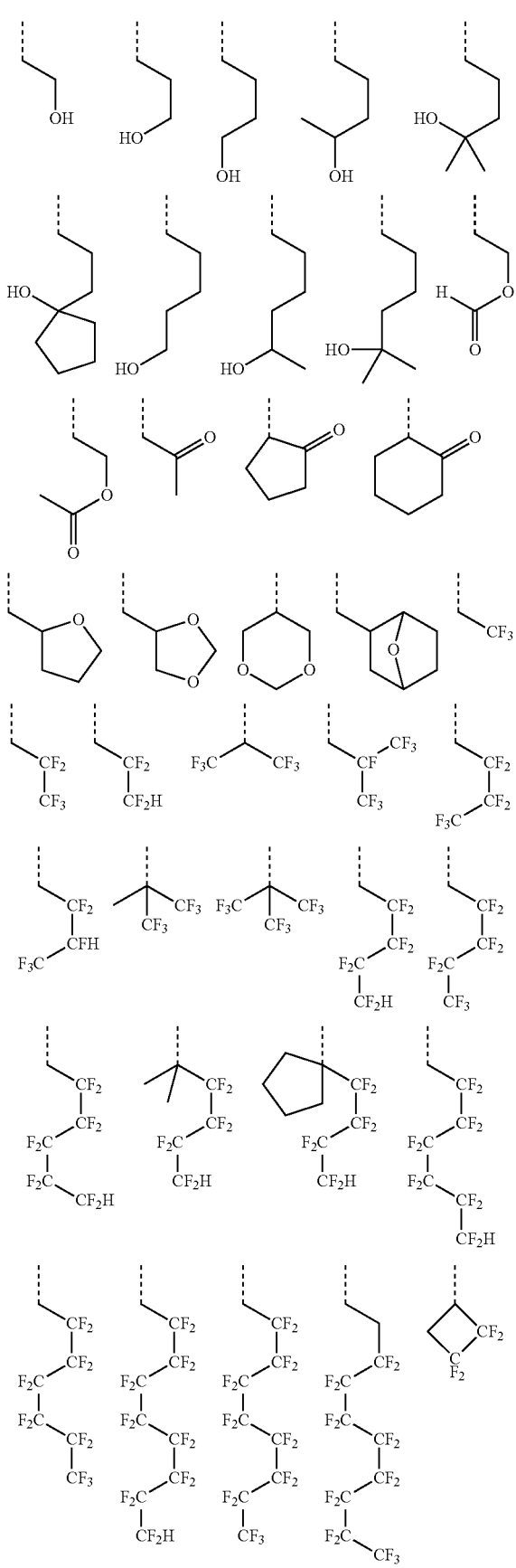
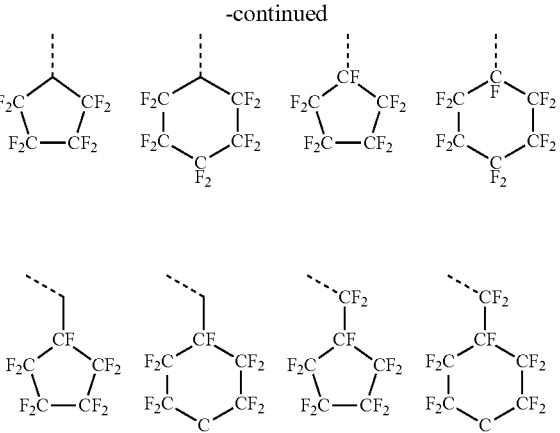

(The broken line denotes a valence bond.)

Preferred examples of $R^{5'}$ include methyl, 1-methylcyclopentyl, 1-ethylcyclopentyl, 1-methylcyclohexyl, 1-ethylcyclohexyl, 2-methyladamantan-2-yl, 2-ethyladamantan-2-yl, 8-methyltricyclo[5.2.1.0$^{2,6}$]decan-8-yl, 8-ethyltricyclo[5.2.1.0$^{2,6}$]decan-8-yl, 4-ethyltetracyclo[6.2.1.1$^{3,6}$.0$^{2,7}$]dodecan-4-yl. Preferably W' is $CH_2$.

Examples of suitable monomers from which recurring units of formula (5L-1) are derived are given below.

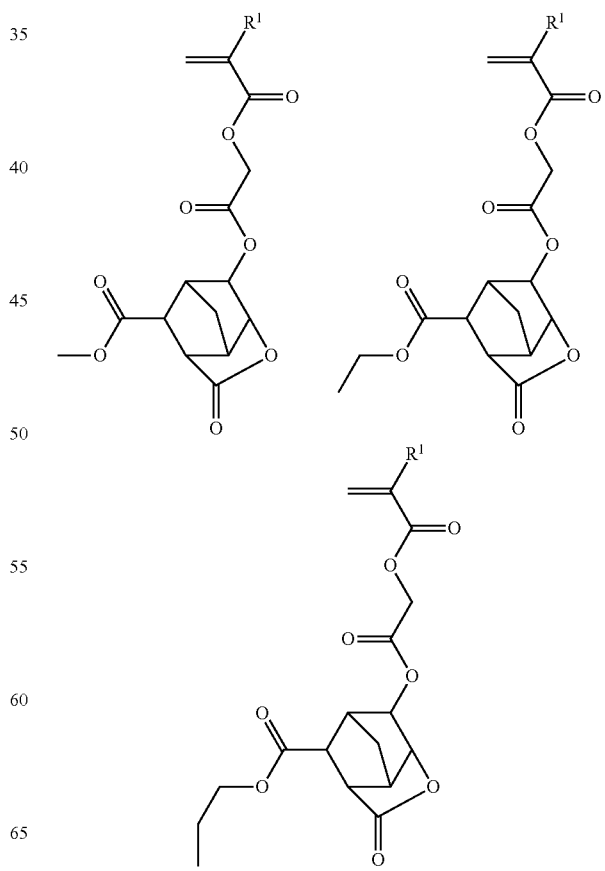

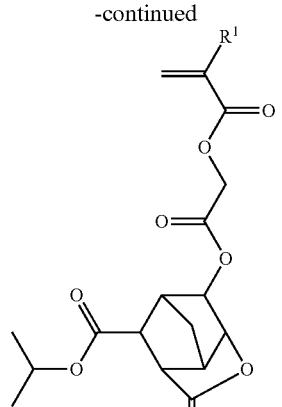
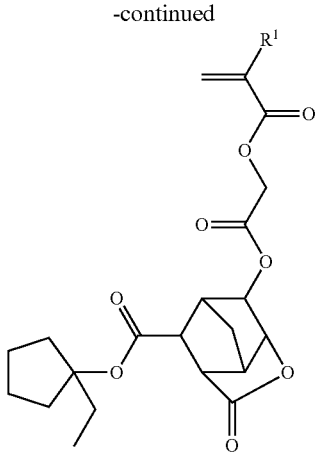

47
-continued
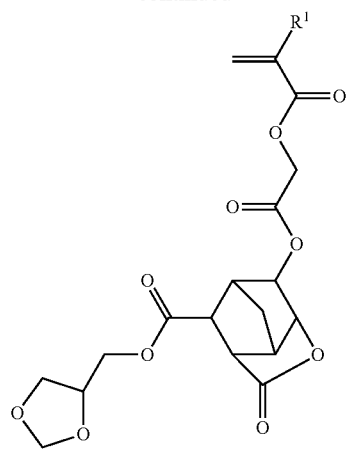
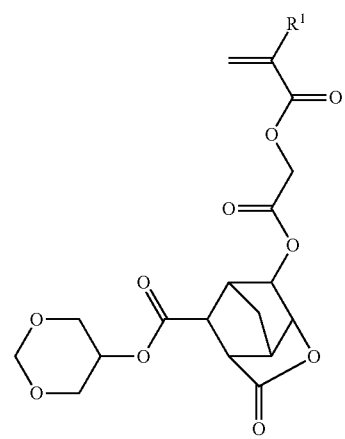
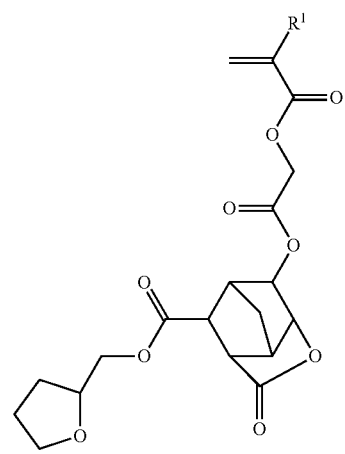
48
-continued
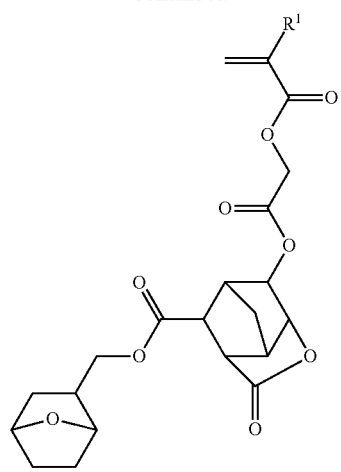
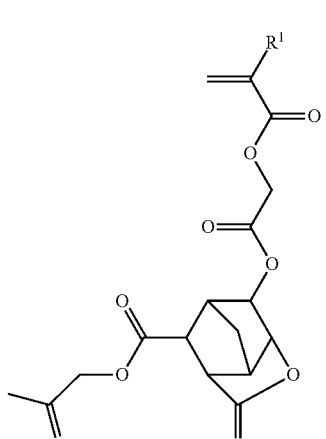
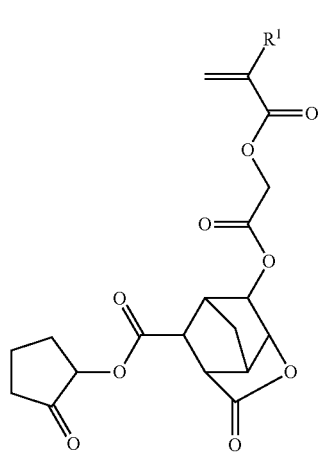

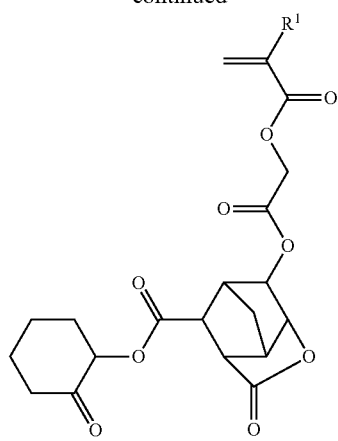
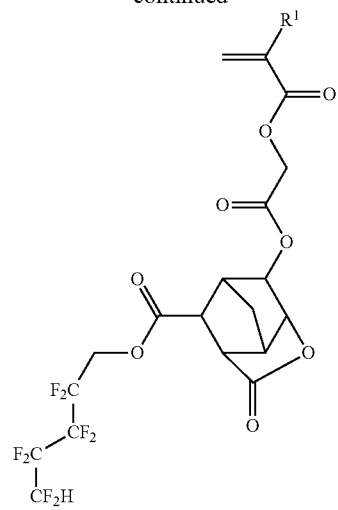
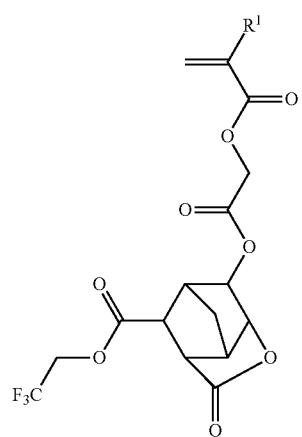
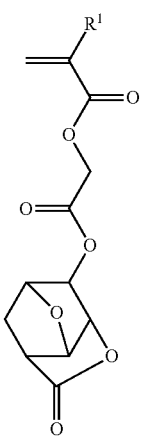
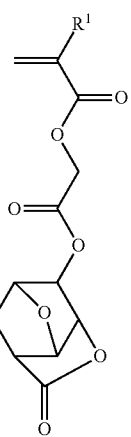
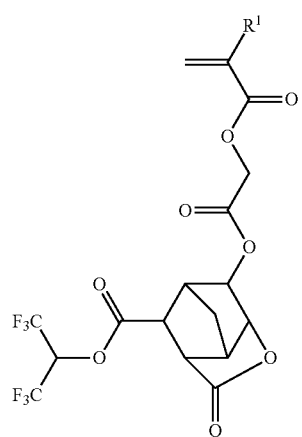
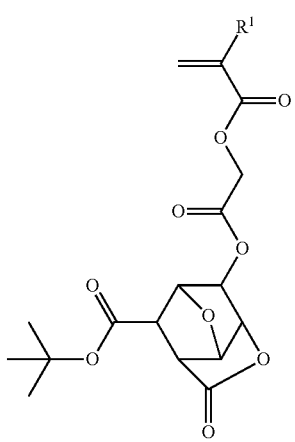

51
-continued
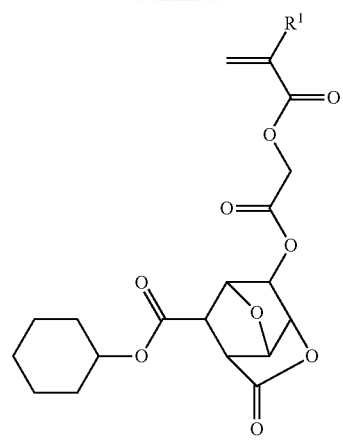
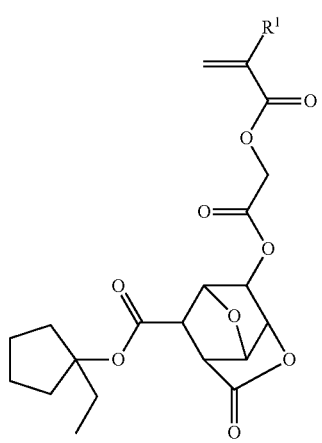
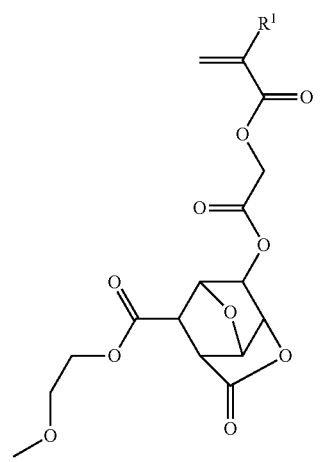
52
-continued
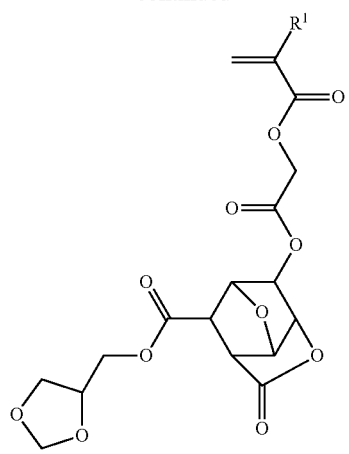
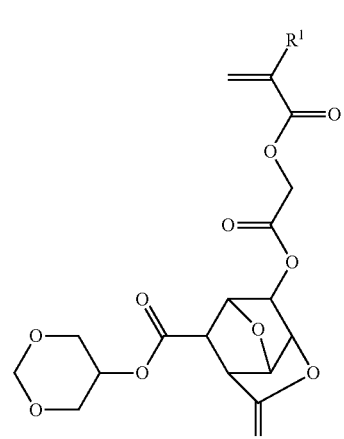
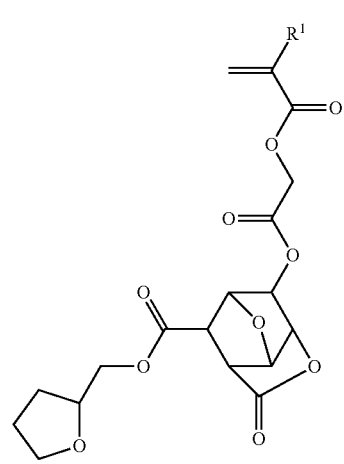

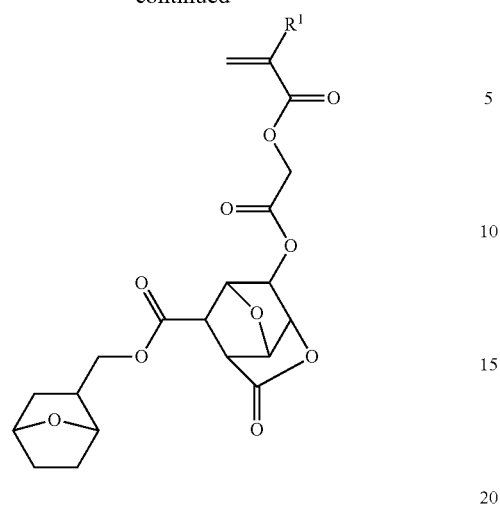
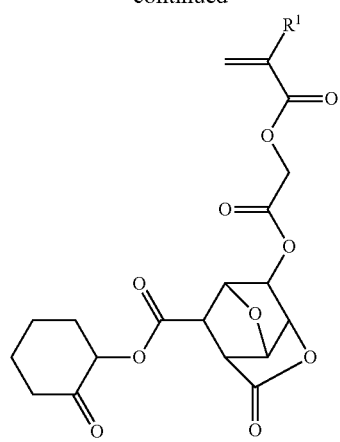
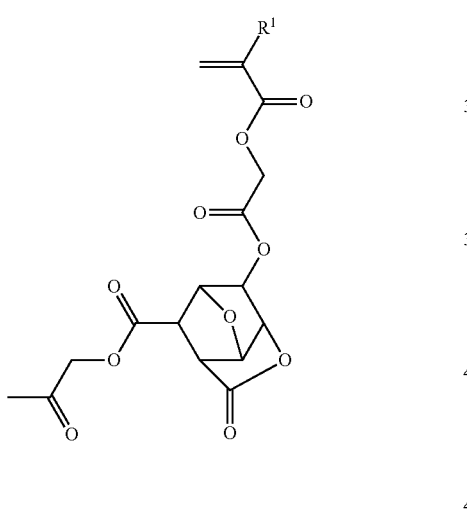
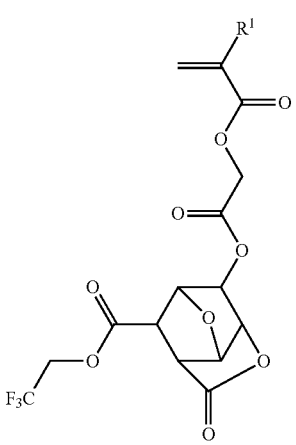
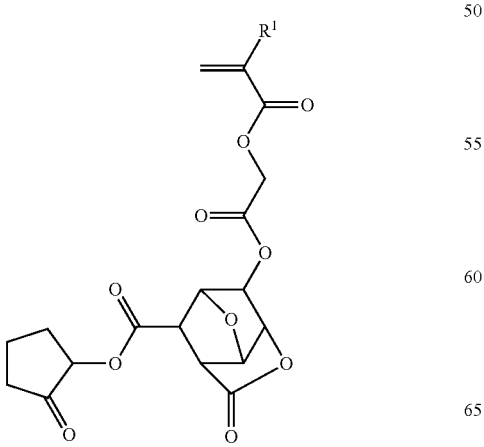
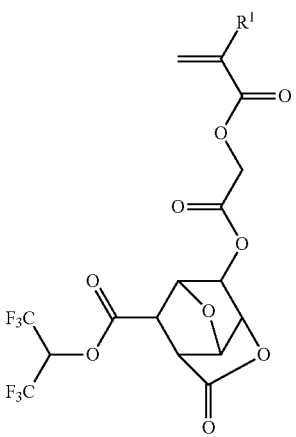

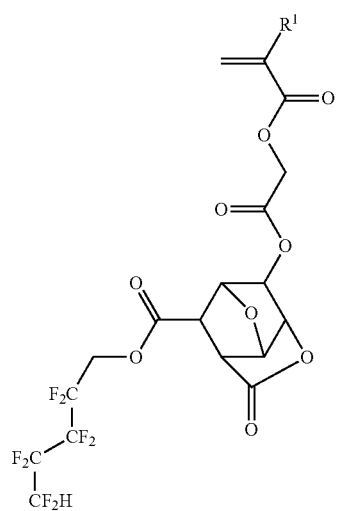

Herein R¹ is as defined above.

Of the monomers from which recurring units of formula (5L-1) are derived, those monomers wherein M'=1 are described in JP-A 2008-031298. Those monomers wherein M'=3 may be similarly synthesized aside from using chlorobutyric chloride instead of chloroacetyl chloride used as the reactant in the synthesis of the compounds wherein M'=1.

Illustrative examples of the recurring units of formula (6) are given below.

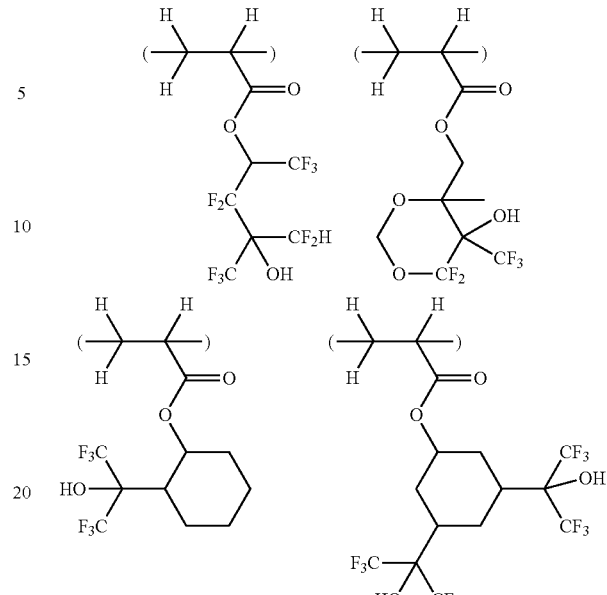

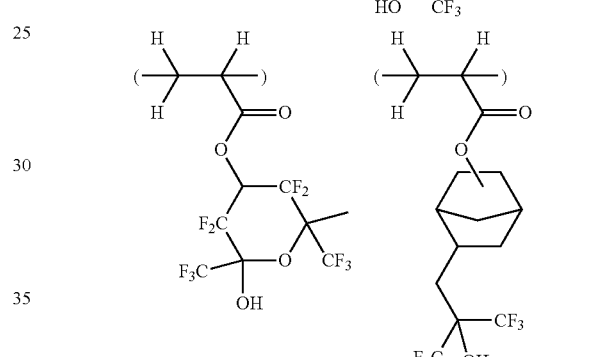

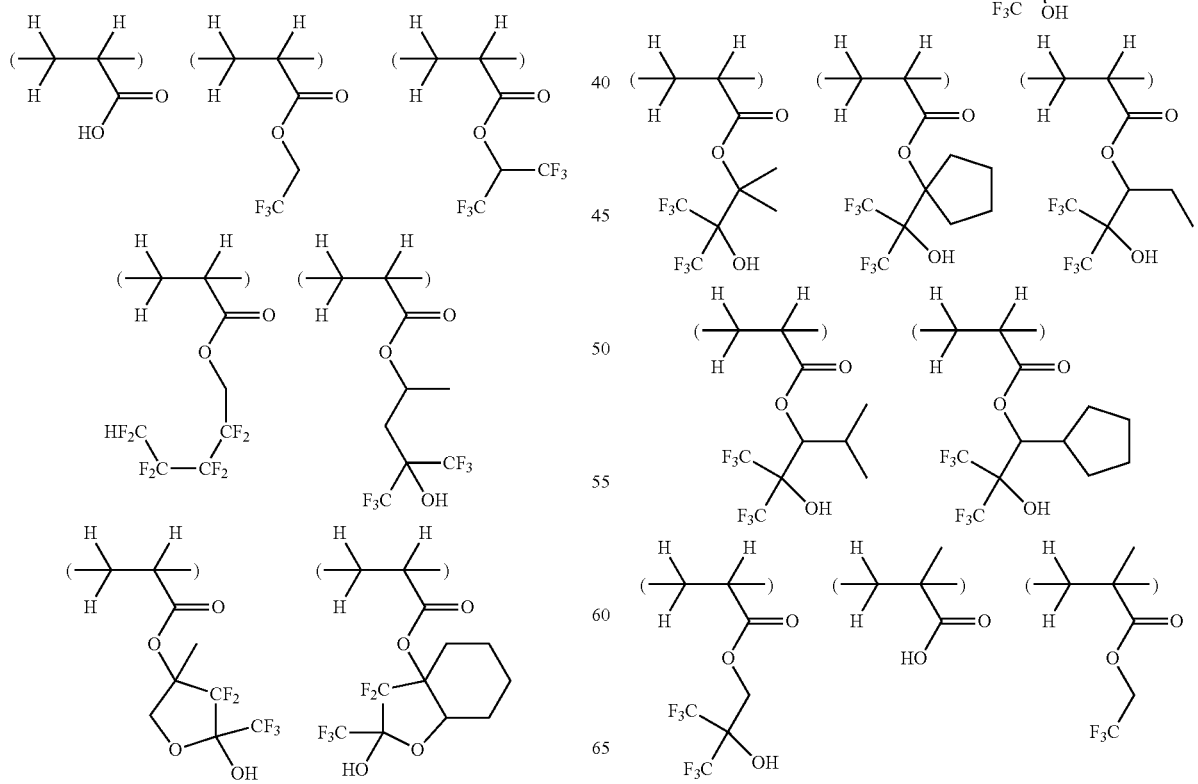

-continued

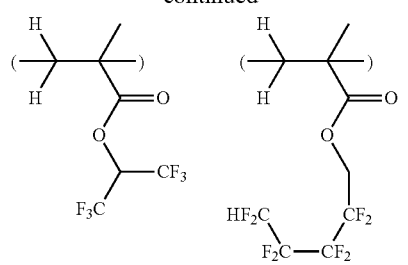
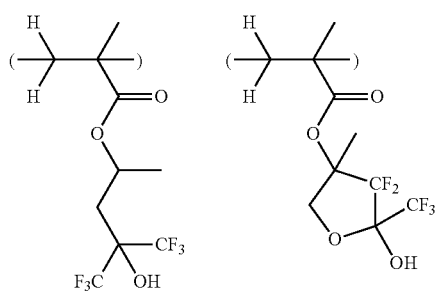
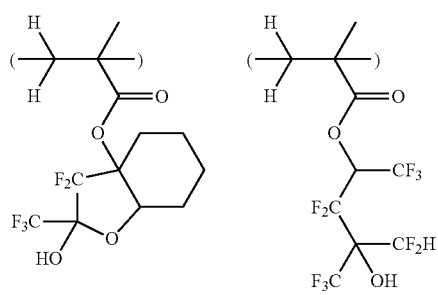
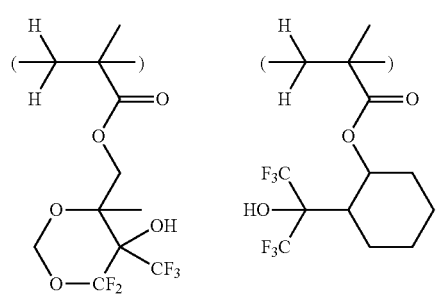
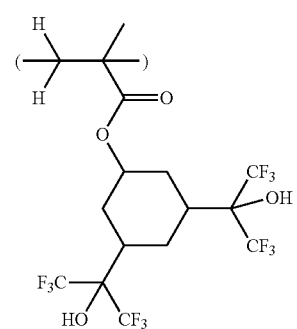

-continued

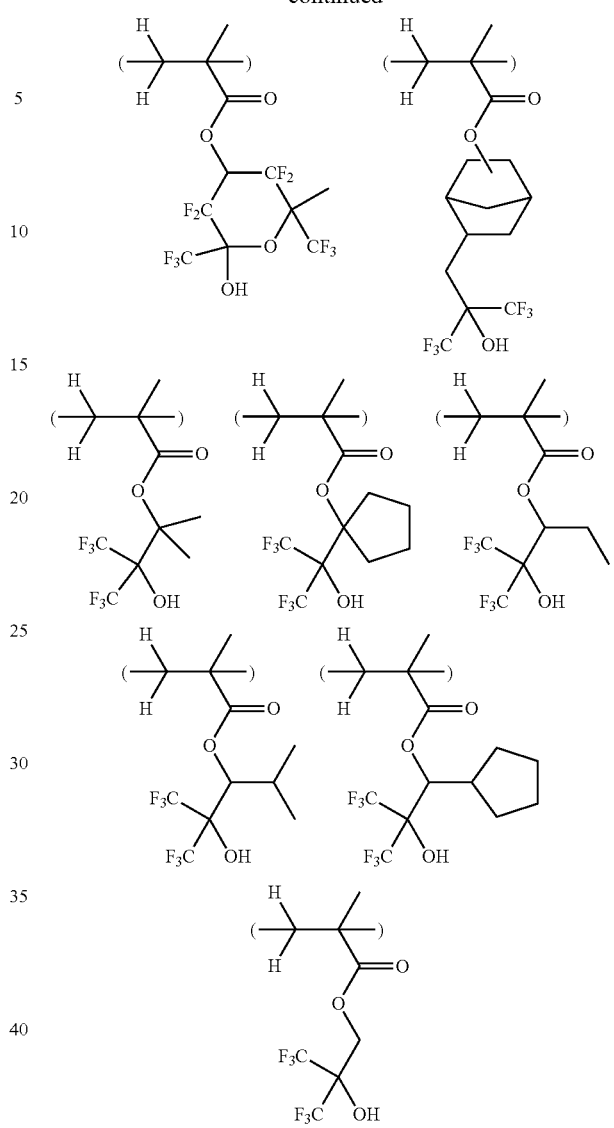

The polymer of the invention may further comprise recurring units derived from another monomer having a carbon-to-carbon double bond other than the foregoing. Examples of the additional monomer include substituted acrylates such as methyl methacrylate, methyl crotonate, dimethyl maleate, and dimethyl itaconate, unsaturated carboxylic acids such as maleic acid, fumaric acid and itaconic acid, cyclic olefins such as norbornene, norbornene derivatives, and tetracyclo [$6.2.1.1^{3,6}.0^{2,7}$]dodecene derivatives, unsaturated acid anhydrides such as itaconic anhydride, and other monomers.

The polymers of the invention are applicable not only to the ArF photolithography, but also to another lithography such as KrF, EB or EUV lithography.

In a still further embodiment, the polymer may further comprise recurring units of at least one type selected from the general formulae (7) to (9) and optionally, recurring units of at least one type selected from the general formulae (4) to (6).

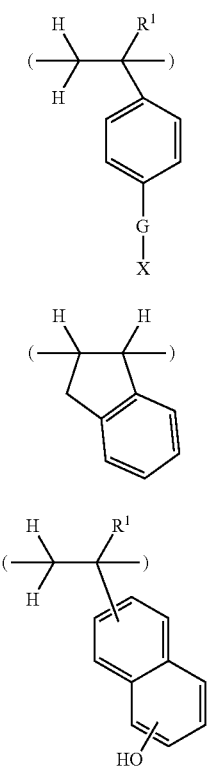

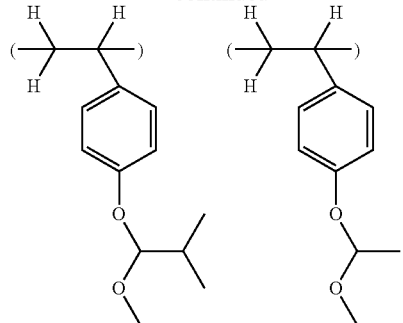

Herein R¹ and X are as defined above, and G is an oxygen atom or carbonyloxy group (—C(=O)O—).

Under the action of an acid, a polymer comprising recurring units of formula (7) is decomposed to generate a phenolic hydroxyl group and/or carboxylic acid whereby it becomes alkali soluble. The acid labile group X may be selected from a variety of such groups, for example, groups of formulae (L1) to (L4) and (L2-2), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms, as illustrated previously.

Illustrative non-limiting examples of the recurring units of formula (7) are given below.

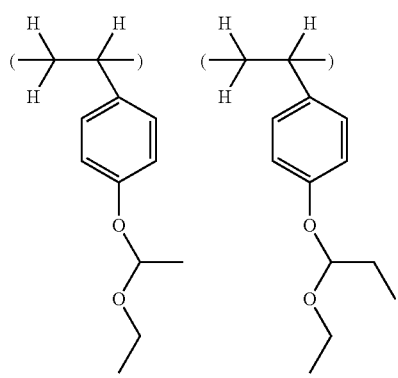

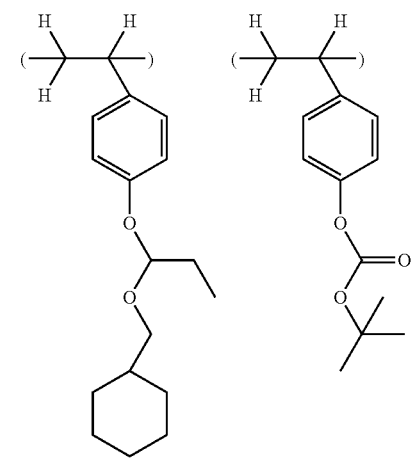

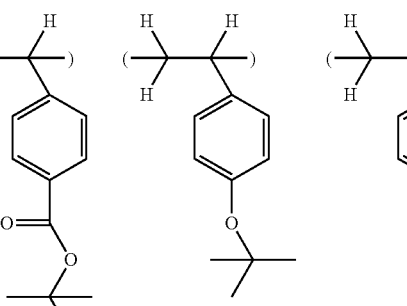

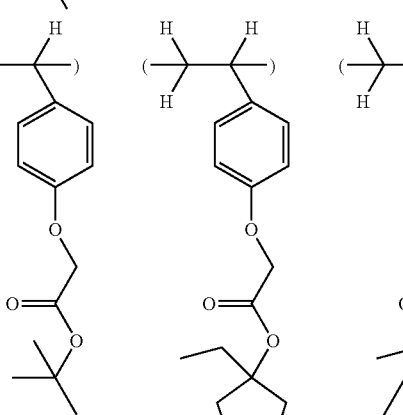

-continued

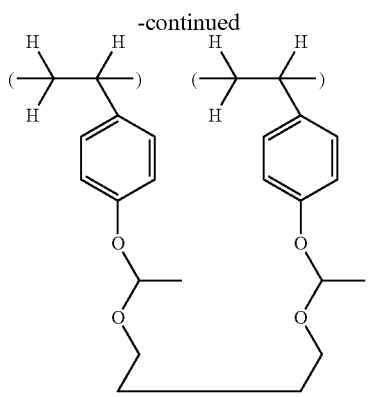

While hydroxyvinylnaphthalene of formula (9) may be substituted at arbitrary positions, typical substituted ones include 6-hydroxy-2-vinylnaphthalene and 4-hydroxy-1-vinylnaphthalene, with 6-hydroxy-2-vinylnaphthalene being preferred.

More preferred are those polymers comprising recurring units of any one type selected from formulae (7) to (9) and recurring units of formula (4) selected from among the recurring units of formulae (4) to (6).

The polymer of the invention comprising recurring units having a sulfonium salt with a polymerizable anion and recurring units of any one or more type selected from formulae (7) to (9) may further comprise recurring units derived from another monomer having a carbon-to-carbon double bond other than the foregoing. Examples of the additional monomer include substituted acrylates such as methyl methacrylate, methyl crotonate, dimethyl maleate, and dimethyl itaconate, unsaturated carboxylic acids such as maleic acid, fumaric acid and itaconic acid, cyclic olefins such as norbornene, norbornene derivatives, tetracyclo[6.2.1.1$^{3,6}$.0$^{2,7}$] dodecene derivatives, and norbornadiens, unsaturated acid anhydrides such as itaconic anhydride, styrene, acenaphthylene, vinylnaphthalene, and other monomers.

The polymers have a weight average molecular weight (Mw) of 1,000 to 500,000, and preferably 3,000 to 100,000. Outside the range, a polymer may suffer an extreme drop of etching resistance or a reduced resolution due to a failure to provide a difference in dissolution rate before and after exposure. The measurement of molecular weight may be performed by gel permeation chromatography (GPC) versus polystyrene standards using N,N-dimethylforamide (DMF) containing a trace of lithium bromide as elute, or a light scattering method.

In the inventive polymer, the preferred proportion of respective recurring units derived from discrete monomers may fall, for example, in the range (mol %) shown below, but is not limited thereto. The polymer may consist essentially of:

(I) from more than 0 mol % to 50 mol %, preferably 1 to 30 mol %, and more preferably 5 to 20 mol % of constituent units of one or more type having formula (1a);

(II) from more than 0 mol % to 80 mol %, preferably 10 to 50 mol %, and more preferably 20 to 40 mol % of constituent units of one or more type having formula (2);

(III) from more than 0 mol % to 80 mol %, preferably 10 to 50 mol %, and more preferably 20 to 40 mol % of constituent units of one or more type having formula (3); and optionally (IV) from 0 mol % to 80 mol %, preferably 0 to 70 mol %, and more preferably 0 to 50 mol % of constituent units of one or more type having formulae (4) to (6) and/or formulae (7) to (9) (if incorporated, more than 0 mol %, and preferably at least 1 mol %); and optionally, (V) from 0 mol % to 50 mol %, preferably 0 to 40 mol %, and more preferably 0 to 30 mol % of constituent units of one or more type derived from the additional monomer(s).

The polymer may be prepared through copolymerization reaction using the compound having formula (1) are derived as a first monomer and one or more compounds having a polymerizable double bond as second and subsequent monomers. Although various modes of copolymerization reaction may be used for the preparation of the inventive polymer, radical polymerization is preferred.

For radical polymerization, preferred reaction conditions include (a) a solvent selected from hydrocarbon solvents such as benzene, ether solvents such as tetrahydrofuran, alcohol solvents such as ethanol, and ketones such as methyl isobutyl ketone; (b) a polymerization initiator selected from azo compounds such as 2,2'-azobisisobutyronitrile and peroxides such as benzoyl peroxide and lauroyl peroxide; (c) a reaction temperature in the range of about 0° C. to about 100° C.; and (d) a reaction time in the range of about 0.5 to about 48 hours. Reaction parameters outside these ranges need not be excluded. Once a polymer is prepared by the above-described procedure, it may be modified by deprotecting some or all acid labile groups and then introducing different acid labile groups so that acid labile groups different from the acid labile groups initially introduced during polymerization are introduced into the polymer. For example, once a polymer is formed through radical polymerization of 4-ethoxyethoxy-styrene and a sulfonium salt with a polymerizable anion as represented by formula (1), the polymer may be modified by eliminating ethoxyethoxy groups from the polymer using acetic acid, pyridinium tosylate or the like, and reacting with di-tert-butyl dicarbonate, tert-butyl chloroacetate, vinyl ether or the like. Then acid labile groups different from the acid labile groups (ethoxyethoxy) initially introduced during polymerization are introduced into the polymer.

Resist Composition

The polymer of the invention is advantageously used as a base resin in a resist composition, and specifically a chemically amplified positive resist composition. Thus a third embodiment of the invention is a positive resist composition comprising the polymer. The positive resist composition preferably comprises:

(A) a base resin comprising the inventive polymer,
(C) an organic solvent, and optionally,
(B) an acid generator,
(D) a quencher, and
(E) a surfactant.

For the positive resist composition, the base resin as component (A) may comprise another resin having a dissolution rate in an alkaline developer that increases under the action of an acid, if desired, as well as the inventive polymer. Exemplary other resins include, but are not limited to, (i) poly(meth)acrylic acid derivatives, (ii) norbornene derivative/maleic anhydride copolymers, (iii) hydrogenated products of ring-opening metathesis polymerization (ROMP) polymers, (iv) vinyl ether/maleic anhydride/(meth)acrylic acid derivative copolymers, and (v) polyhydroxystyrene derivatives. Examples of these resins are described in JP-A 2009-263487 (US 20090269696, EP 2112554).

The inventive polymer and the other polymer are preferably blended in a weight ratio from 100:0 to 10:90, more preferably from 100:0 to 20:80. If the blend ratio of the inventive polymer is below this range, the resist composition would become poor in some of the desired properties. The performance of the resist composition can be adjusted by properly changing the blend ratio of the inventive polymer. The polymer is not limited to one type and a mixture of two or more polymers may be added. The use of plural polymers allows for easy adjustment of resist properties.

In the practice of the invention, an acid generator is optionally used as component (B). Where a photoacid generator is added as the acid generator, it may be any compound capable of generating an acid upon exposure to high-energy radiation. Suitable PAGs include sulfonium salts, iodonium salts, sulfonyldiazomethane, N-sulfonyloxyimide, and oxime-O-sulfonate acid generators. Exemplary PAGs are given in JP-A 2009-263487.

Preferred among others are those acid generators having the general formula (PAG-1).

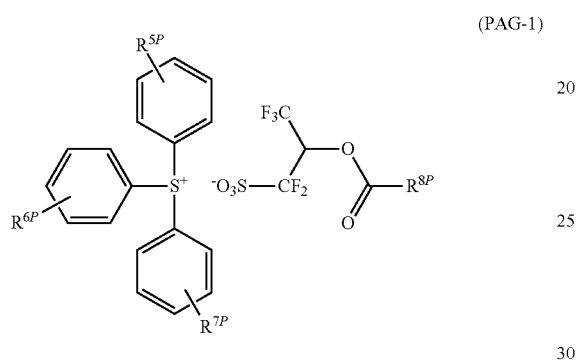

(PAG-1)

Herein $R^{5P}$, $R^{6P}$ and $R^{7P}$ are each independently hydrogen or a monovalent, straight, branched or cyclic $C_1$-$C_{20}$ hydrocarbon group which may contain a heteroatom. Examples of the hydrocarbon group which may contain a heteroatom include methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, butyladamantyl, and modified forms of the foregoing in which any carbon-carbon bond is interrupted by a heteroatom group such as —O—, —S—, —SO—, —SO$_2$—, —NH—, —C(=O)—, —C(=O)O—, or —C(=O)NH—, or any hydrogen atom is replaced by a functional group such as —OH, —NH$_2$, —CHO, or —CO$_2$H. $R^{8P}$ is a monovalent, straight, branched or cyclic $C_7$-$C_{30}$ hydrocarbon group which may contain a heteroatom, examples of which are illustrated below, but not limited thereto.

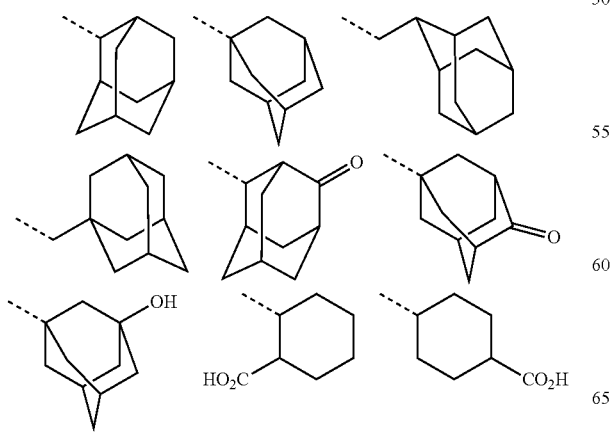

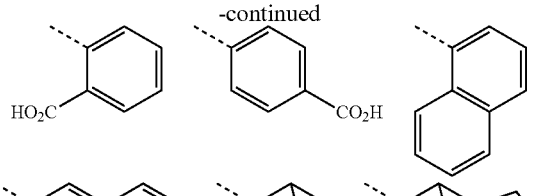

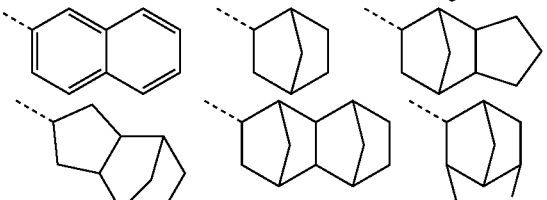

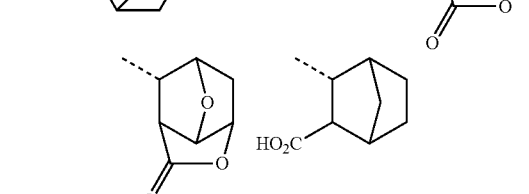

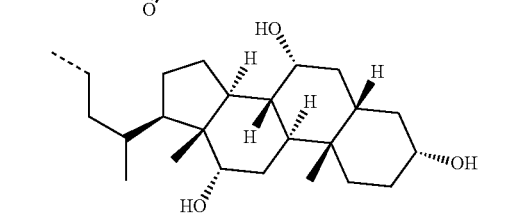

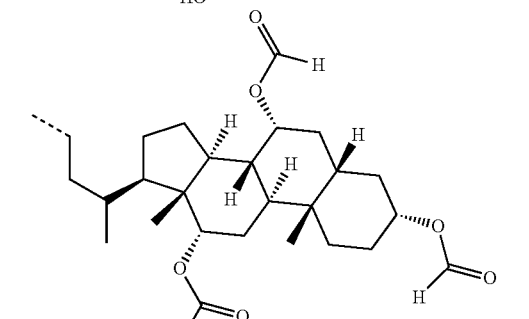

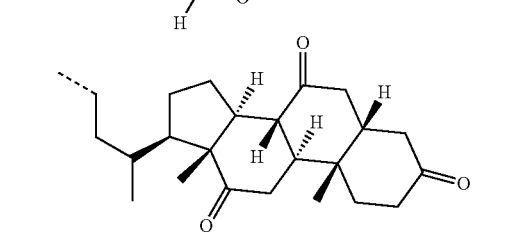

Illustrative examples of the acid generators having formula (PAG-1) are given below.

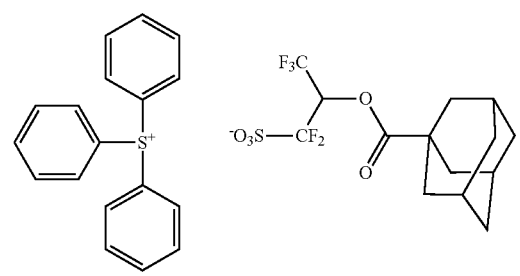

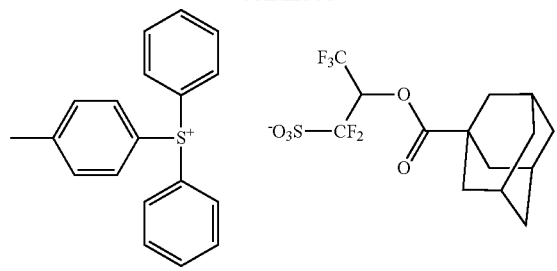
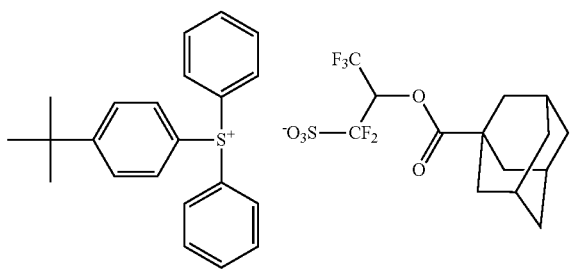
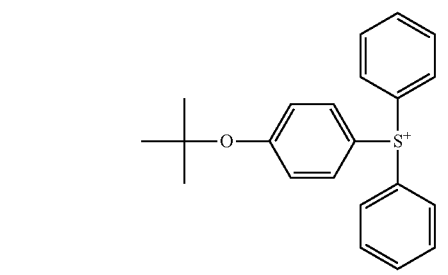
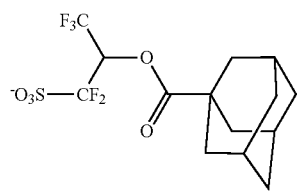
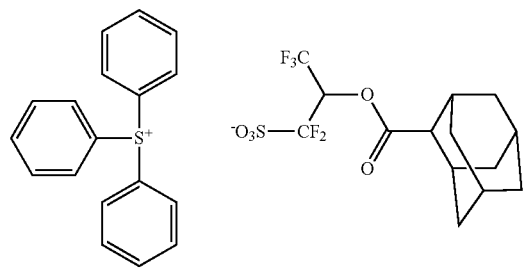
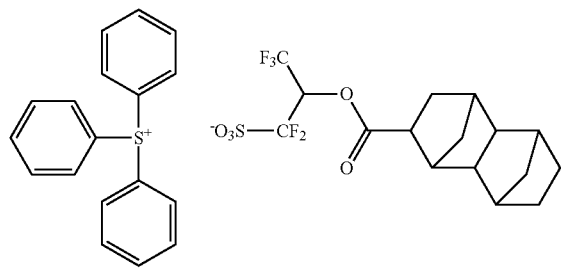
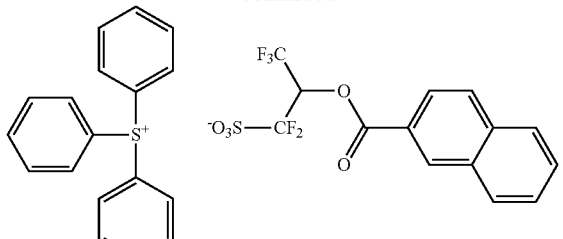
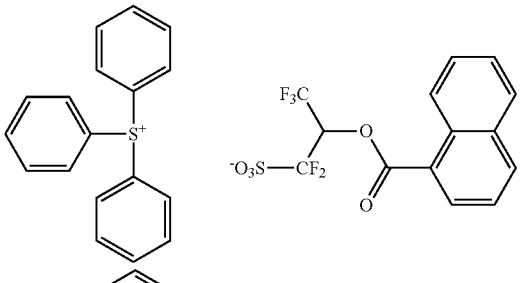
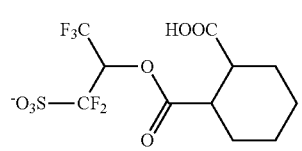
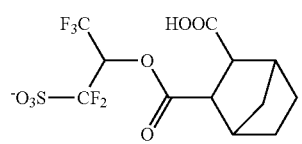
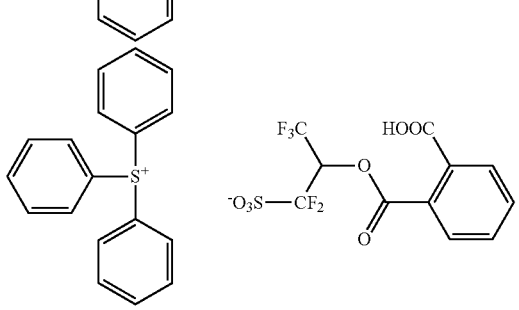
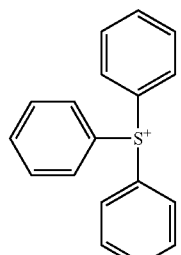
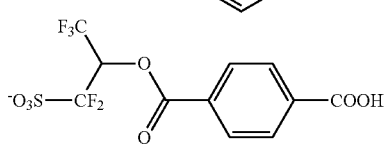

-continued

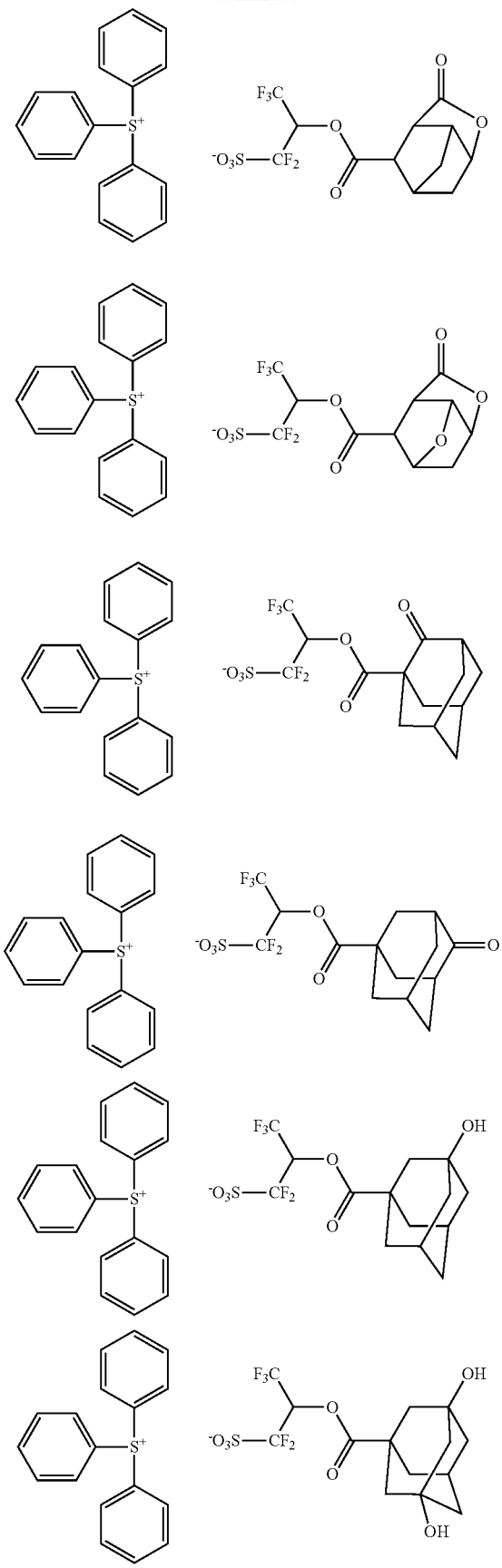

-continued

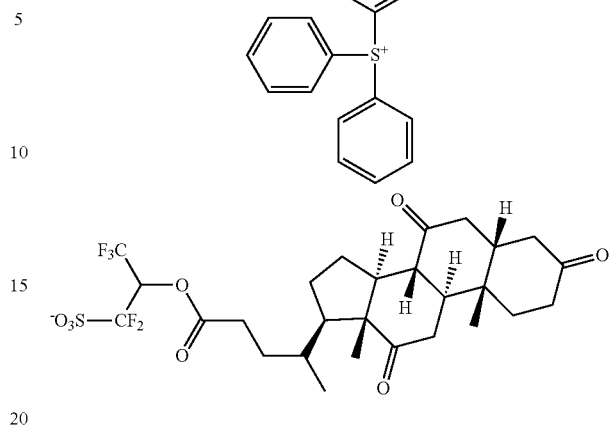

In the chemically amplified resist composition, the PAG (B) may be added in any desired amount as long as the objects of the invention are not compromised. An appropriate amount of the PAG is 0.1 to 10 parts, and more preferably 0.1 to 5 parts by weight per 100 parts by weight of the base resin in the composition. Too high a proportion of the PAG may give rise to problems of degraded resolution and foreign matter upon development and resist film peeling. The PAGs may be used alone or in admixture of two or more. The transmittance of the resist film can be controlled by using a PAG having a low transmittance at the exposure wavelength and adjusting the amount of the PAG added.

It is noted that an acid diffusion controlling function may be provided when the PAG is an onium salt capable of generating a weak acid. Specifically, in a system using the inventive polymer capable of generating a strong acid in combination with an onium salt capable of generating a weak acid (e.g., non-fluorinated sulfonic acid or carboxylic acid), if the strong acid generated from the inventive polymer upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If an onium salt capable of generating a strong acid and an onium salt capable of generating a weak acid are used in admixture, an exchange from the strong acid to the weak acid as above can take place, but it never happens that the weak acid collides with the unreacted onium salt capable of generating a strong acid to induce a salt exchange. This is because of a likelihood of an onium cation forming an ion pair with a stronger acid anion.

The organic solvent (C) used herein may be any organic solvent in which the base resin, acid generator, and other components are soluble. Illustrative, non-limiting, examples of the organic solvent include ketones such as cyclohexanone and methyl amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as □-butyrolactone. These solvents may be used alone or in combinations of two or more thereof. Of the above organic solvents, it is recommended to use diethylene glycol dimethyl ether, 1-ethoxy-2-propanol, PGMEA, and mixtures thereof because the acid generator is most soluble therein.

An appropriate amount of the organic solvent used is 200 to 1,000 parts, especially 400 to 800 parts by weight per 100 parts by weight of the base resin.

A quencher (D) may be optionally used in the resist composition of the invention. The term "quencher" as used herein has a meaning generally known in the art and refers to a compound capable of suppressing the rate of diffusion when the acid generated by the acid generator diffuses within the resist film. The inclusion of quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile.

Examples of suitable quenchers include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, carbamate derivatives, and ammonium salts. Exemplary quenchers are given in JP-A 2009-263487.

The quencher is preferably formulated in an amount of 0.001 to 2 parts, and especially 0.01 to 1 part by weight, per 100 parts by weight of the base resin. Less than 0.001 phr of the quencher may achieve no addition effect whereas more than 2 phr may lead to too low a sensitivity.

Optionally, the resist composition of the invention may further comprise (E) a surfactant which is commonly used for improving the coating characteristics. The surfactant may be added in conventional amounts so long as this does not compromise the objects of the invention.

Illustrative, non-limiting, examples of the surfactant include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (JEMCO Inc.), Megaface F171, F172, F173, R08, R30, R90 and R94 (DIC Corp.), Fluorad FC-430, FC-431, FC-4430 and FC-4432 (Sumitomo 3M Co., Ltd.), Asahiguard AG710, Surflon S-381, S-382, S-386, SC101, SC102, SC103, SC104, SC105, SC106, KH-10, KH-20, KH-30, KH-40, S-386, S-651 and S-420 (AGC Seimi Chemical Co., Ltd.), and Surfynol E1004 (Nisshin Chemical Co., Ltd.); organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo Co., Ltd.).

Additional useful surfactants include partially fluorinated oxetane ring-opened polymers having the structural formula (surf-1).

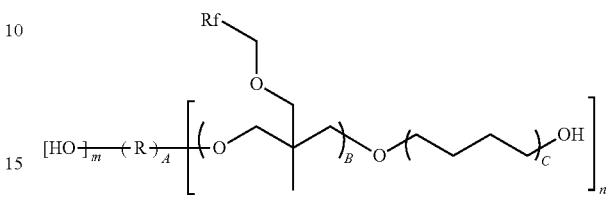

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

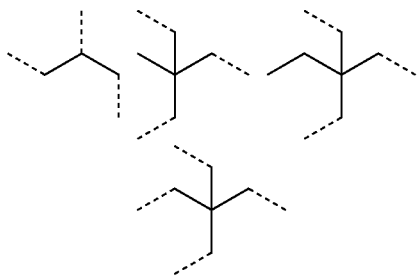

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used. Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. A is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either in blocks or randomly. For the preparation of surfactants in the form of partially fluorinated oxetane ring-opened polymers, reference should be made to U.S. Pat. No. 5,650,483, for example.

Of the foregoing surfactants, FC-4430, Surflon S-381, Surfynol E1004, KH-20, S-386, S-651, S-420 and oxetane ring-opened polymers of formula (surf-1) are preferred. These surfactants may be used alone or in admixture.

In the chemically amplified resist composition, the surfactant is preferably added in an amount of up to 2 parts, and especially up to 1 part by weight, per 100 parts by weight of the base resin. If used, the amount of surfactant is at least 0.01 phr.

In one embodiment of the invention wherein the resist composition is worked by immersion lithography using water, especially in the absence of a resist protective coating, a surfactant may be added to the resist composition, the surfactant having a function to segregate at the resist surface after spin coating to prevent or reduce water penetration or leaching. This surfactant is a polymeric surfactant which is insoluble in water and soluble in an alkaline developer, and preferably improves water repellency and water slippage. Exemplary polymeric surfactants are described in JP-A 2009-263487.

In the resist composition, the polymeric surfactant is preferably added in an amount of 0.001 to 20 parts, and more preferably 0.01 to 10 parts by weight, per 100 parts by weight of the base resin. With respect to the polymeric surfactant, reference should also be made to JP-A 2007-297590.

While the resist composition of the invention typically comprises a polymer or base resin, organic solvent, acid generator, and quencher as described above, there may be added optional other ingredients such as dissolution inhibitors, acidic compounds, stabilizers, and dyes. Optional ingredients may be added in conventional amounts so long as this does not compromise the objects of the invention.

Process

A fourth embodiment is a pattern forming process using the resist composition described above. Pattern formation using the resist composition of the invention may be performed by well-known lithography processes. The process generally involves coating, prebaking, exposure, PEB, and development. If necessary, any additional steps may be added.

First the resist composition is applied onto a substrate for integrated circuitry fabrication (e.g., Si, $SiO_2$, SiN, SiON, TiN, WSi, BPSG, SOG, organic antireflective film, etc.) or a substrate for mask circuitry fabrication (e.g., Cr, CrO, CrON, MoSi, etc.) by a suitable coating technique such as spin coating. The coating is prebaked on a hot plate at a temperature of 60 to 150° C. for 1 to 10 minutes, preferably 80 to 140° C. for 1 to 5 minutes. The resulting resist film is generally 0.05 to 2.0 μm thick. Through a photomask having a desired pattern disposed over the substrate, the resist film is then exposed to high-energy radiation such as deep-UV, excimer laser or x-ray, or soft x-ray having a wavelength of 3 to 15 nm in an exposure dose preferably in the range of 1 to 200 $mJ/cm^2$, more preferably 10 to 100 $mJ/cm^2$. Alternatively, pattern formation may be performed by writing with an electron beam directly (not through a mask). Light exposure may be done by a conventional exposure process or in some cases, by an immersion process of providing liquid impregnation between the mask and the resist. In the case of immersion lithography, a protective coating which is insoluble in water may be used. The resist film is then post-exposure baked (PEB) on a hot plate at 60 to 150° C. for 1 to 5 minutes, and preferably at 80 to 140° C. for 1 to 3 minutes. Finally, development is carried out using as the developer an aqueous alkali solution, such as a 0.1 to 5 wt %, preferably 2 to 3 wt %, aqueous solution of tetramethylammonium hydroxide (TMAH), this being done by a conventional method such as dip, puddle, or spray development for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV or excimer laser having a wavelength of 250 to 190 nm, x-ray, or electron beam. The desired pattern may not be obtainable outside the upper and lower limits of the above range.

The water-insoluble protective coating which is used in the immersion lithography is to prevent the resist coating from being leached and to improve water slippage at the coating surface and is generally divided into two types. The first type is an organic solvent-strippable protective coating which must be stripped, prior to alkaline development, with an organic solvent in which the resist coating is not dissolvable. The second type is an alkali-soluble protective coating which is soluble in an alkaline developer so that it can be removed simultaneously with the removal of solubilized areas of the resist coating. The protective coating of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a solution, from which the protective coating of the second type is formed.

Any desired step may be added to the pattern forming process. For example, after a photoresist coating is formed, the process may proceed to a step of rinsing with pure water (post-soaking) for extracting the acid generator or the like from the coating surface or washing away particles. After exposure, the process may proceed to a step of rinsing (post-soaking) for removing any water remaining on the coating after exposure.

EXAMPLE

Examples and Comparative Examples are given below by way of illustration and not by way of limitation.

Polymerizable sulfonium salts for use in polymers were synthesized according to the following formulation.

Synthesis Example 1

Synthesis of 4-fluorophenyldiphenylsulfonium bromide

Diphenyl sulfoxide, 40 g (0.2 mole), was dissolved in 400 g of dichloromethane, which was stirred under ice cooling. At a temperature below 20° C., 65 g (0.6 mole) of trimethylsilyl chloride was added dropwise to the solution, which was aged for 30 minutes at the temperature. Then, a Grignard reagent which had been prepared from 14.6 g (0.6 mole) of metallic magnesium, 105 g (0.6 mole) of 4-fluorobromobenzene and 300 g of tetrahydrofuran (THF) was added dropwise at a temperature below 20° C. The reaction solution was aged for one hour, after which 50 g of water at a temperature below 20° C. was added to quench the reaction. To this solution, 300 g of water, 10 g of 12N hydrochloric acid, and 200 g of diethyl ether were further added. The water layer was separated and washed with 100 g of diethyl ether, yielding an aqueous solution of 4-fluorophenyldiphenylsulfonium bromide. The compound in aqueous solution form was used in the subsequent reaction without further isolation.

Synthesis Example 2

Synthesis of benzyltrimethylammonium 1,1,3,3,3-pentafluoro-2-pivaloyloxypropane-1-sulfonate In 325 g of water was dispersed 46.4 g (0.2 mole) of 1,1,3,3,3-pentafluoro-2-propan-2-yl pivalate which had been synthesized by the standard method. 41.6 g (0.4 mole) of sodium hydrogen sulfite was added to the dispersion, whereupon reaction took place at 100° C. for 48 hours. After the reaction solution was allowed to cool down, toluene was added for separatory operation. The water layer was separated, and 37.1 g (0.2 mole) of benzyltrimethylammonium chloride and 300 g of dichloromethane were added thereto, whereby the desired compound was extracted into the organic layer. By washing the organic layer with water, removing the solvent, adding diisopropyl ether to the residue for crystallization, filtration and drying, the target compound was obtained. White crystals, 77 g, yield 83%.

Synthesis Example 3

Synthesis of benzyltrimethylammonium 1,1,3,3,3-pentafluoro-2-hydroxypropane-1-sulfonate In 139 g of methanol was dissolved 46.3 g (0.1 mole) of benzyltrimethylammonium 1,1,3,3,3-pentafluoro-2-pivaloyloxypropane-1-sulfonate in Synthesis Example 2. The solution was stirred under ice cooling, to which a solution of 8.0 g (0.2 mole) of sodium hydroxide in 24 g of water was added dropwise at a temperature below 20° C. The solution was stirred overnight at room temperature, after which 21 g of conc. hydrochloric acid and 60 g of water were added to quench the reaction. Methanol was removed in vacuum from the reaction solution, dichloromethane and water were added to the residue, and the organic layer was separated and concentrated again. To the residue containing some white crystals, 150 g of diisopropyl ether was added for crystallization. Filtration and drying gave the target compound. White crystals, 37 g, yield 98%.

Synthesis Example 4

Synthesis of benzyltrimethylammonium 1,1,3,3,3-pentafluoro-2-(methacryloyloxy)propane-1-sulfonate In 152 g of dichloromethane was dissolved 37.9 g (0.1 mole) of benzyltrimethylammonium 1,1,3,3,3-pentafluoro-2-hydroxypropane-1-sulfonate in Synthesis Example 3. The solution was combined with 11.1 g (0.11 mole) of triethylamine and 0.06 g (0.005 mole) of 4-dimethylaminopyridine and stirred under ice cooling. At a temperature below 20° C., 16.2 g (0.105 mole) of methacrylic anhydride was added dropwise thereto. Stirring was continued overnight at room temperature, after which 13 g of conc. hydrochloric acid and 40 g of water were added to quench the reaction. The organic layer was separated and washed three times with 100 g of a 10 wt % aqueous solution of benzyltrimethylammonium chloride. A minute amount of a polymerization inhibitor was added, the solvent was removed in vacuum, and 150 g of diisopropyl ether was added to the residue for crystallization. Filtration and drying gave the target compound. White crystals, 31 g, yield 73%.

Synthesis Example 5

Synthesis of 4-fluorophenyldiphenylsulfonium 1,1,3,3,3-pentafluoro-2-(methacryloyloxy)propane-1-sulfonate (PAG-1)

An amount (corresponding to 0.05 mole) of an aqueous solution of 4-fluorophenyldiphenylsulfonium bromide in Synthesis Example 1 and 22.4 g (0.05 mole) of benzyltrimethylammonium 1,1,3,3,3-pentafluoro-2-(methacryloyloxy)propane-1-sulfonate in Synthesis Example 4 were added to 200 g of dichloromethane and stirred. The organic layer was separated and washed three times with 200 g of water. A minute amount of a polymerization inhibitor was added to the organic layer, and the solvent was removed in vacuum. Diisopropyl ether was added to the residue for crystallization. Filtration and drying gave the target compound. White crystals, 27.5 g, yield 95%.

Figure 2:
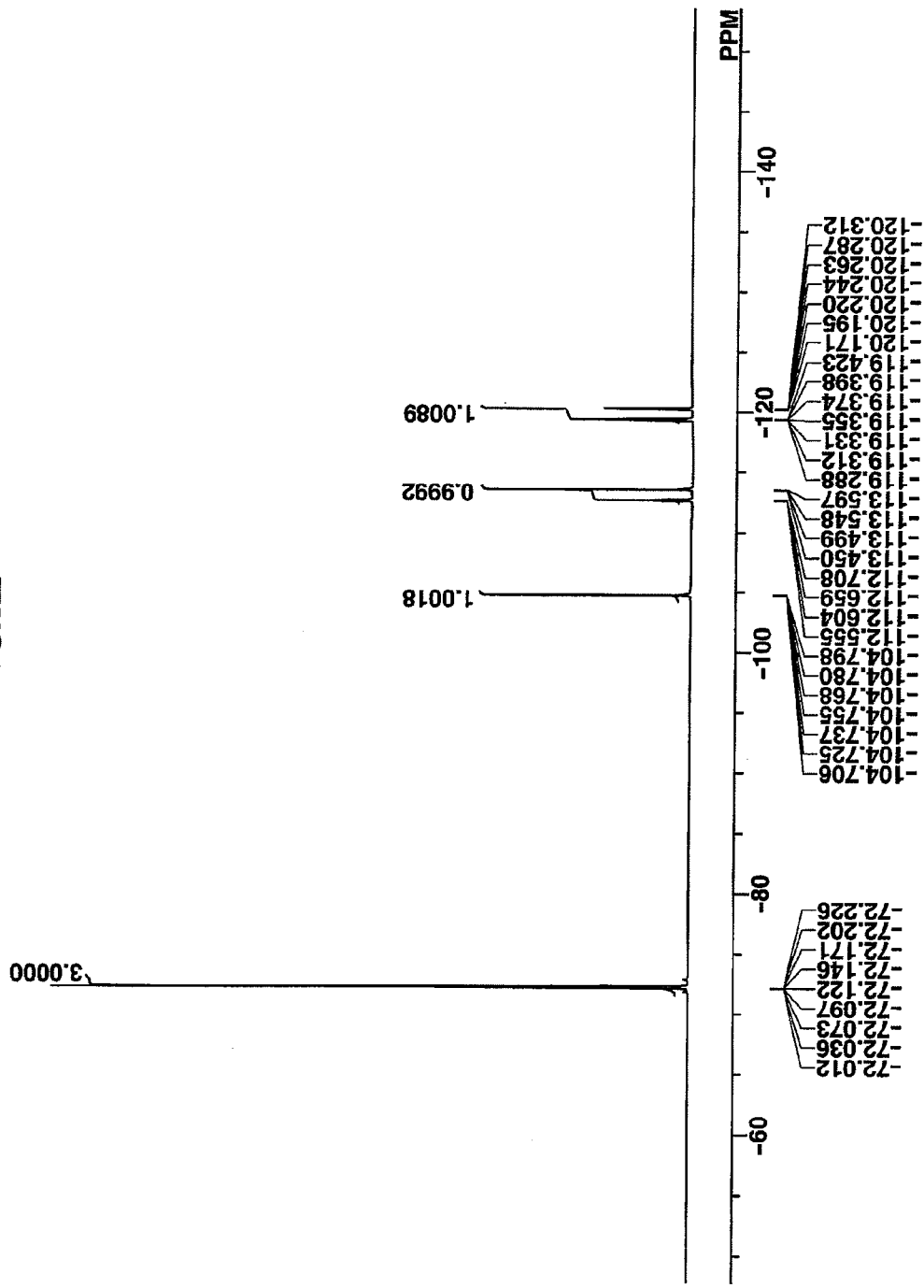
FIG. 2 is a diagram showing the $^{19}$F-NMR spectrum of PAG-1 in Synthesis Example 5.

The target compound was analyzed by spectroscopy. The nuclear magnetic resonance spectra, $^1$H-NMR and $^{19}$F-NMR are shown in FIGS. 1 and 2, respectively. The data of infrared (IR) absorption spectroscopy and time-of-flight mass spectrometry (TOFMS) are shown below.

IR spectra (KBr): 1733, 1588, 1492, 1474, 1445, 1375, 1256, 1213, 1184, 1172, 1161, 1138, 1116, 1068, 1009, 991, 902, 839, 811, 767, 755, 686, 639 cm$^{-1}$
TOFMS (MALDI): positive M$^+$281
(corresponding to $(C_6H_4F)(C_6H_5)_2S^+$)
negative M$^-$297
(corresponding to $CF_3CH(OCO(CH_3)=CH_2) CF_2SO_3^-$)

Comparative Synthesis Example 1

Synthesis of 4-fluorophenyldiphenylsulfonium 1,1,3,3,3-pentafluoro-2-pivaloyloxypropane-1-sulfonate (PAG-2)

An aqueous solution of 4-fluorophenyldiphenylsulfonium bromide in Synthesis Example 1 and benzyltrimethylammonium 1,1,3,3,3-pentafluoro-2-pivaloyloxypropane-1-sulfonate were mixed in dichloromethane. The organic layer was separated and washed three times with water, from which the solvent was removed in vacuum. Diisopropyl ether was added to the residue for crystallization. Filtration and drying gave the target compound.

Figure 3:
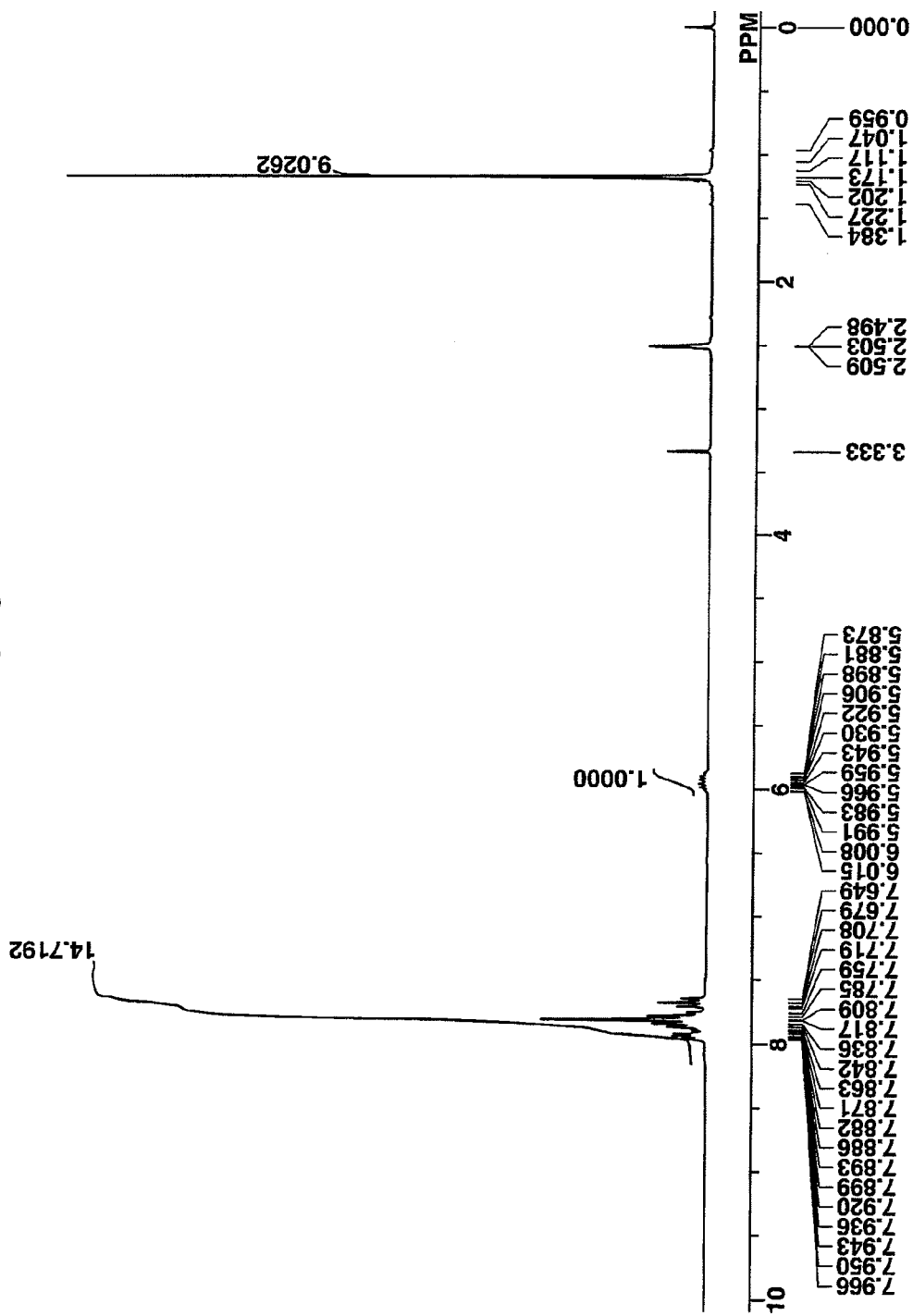
FIG. 3 is a diagram showing the $^1$H-NMR spectrum of PAG-2 in Comparative Synthesis Example 1.
Figure 4:
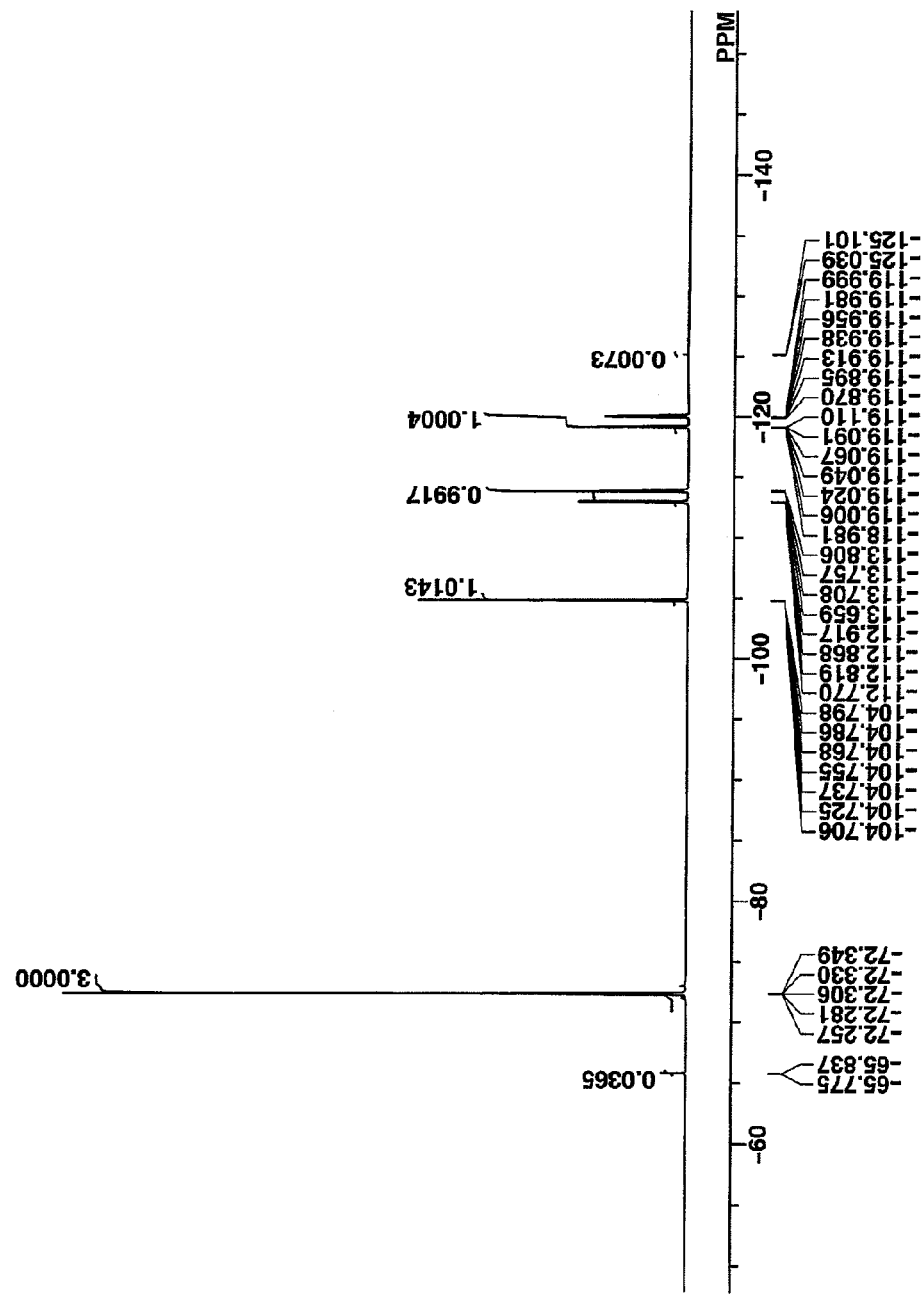
FIG. 4 is a diagram showing the $^{19}$F-NMR spectrum of PAG-2 in Comparative Synthesis Example 1.

The compound was analyzed by spectroscopy. The nuclear magnetic resonance spectra, $^1$H-NMR and $^{19}$F-NMR are shown in FIGS. 3 and 4, respectively. In $^{19}$F-NMR, a peak assigned to fluorine in 4-fluorophenyldiphenylsulfonium cation was observed near −104 ppm.

Comparative Synthesis Example 2

Figure 5:
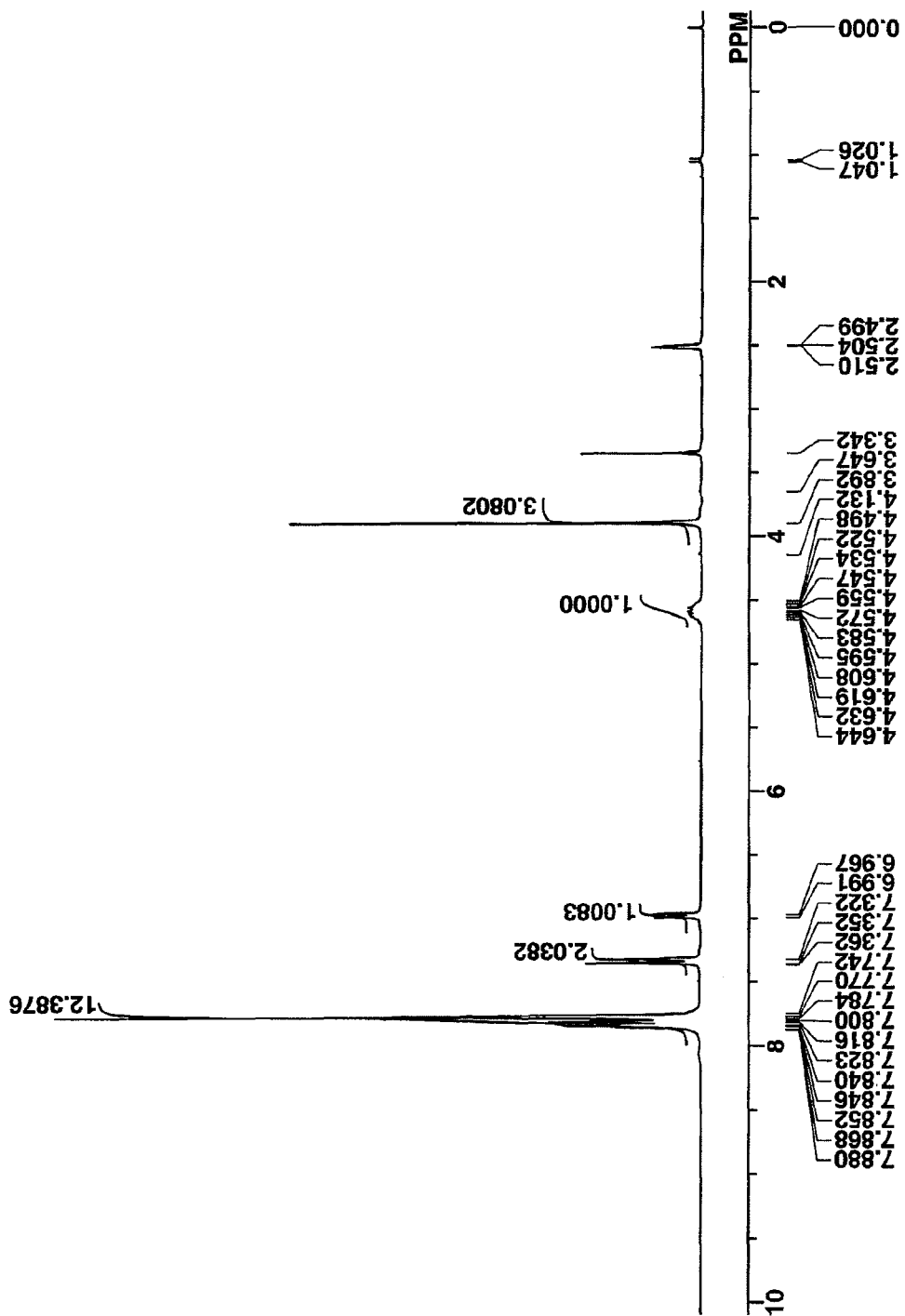
FIG. 5 is a diagram showing the $^1$H-NMR spectrum of PAG-3 in Comparative Synthesis Example 2.
Figure 6:
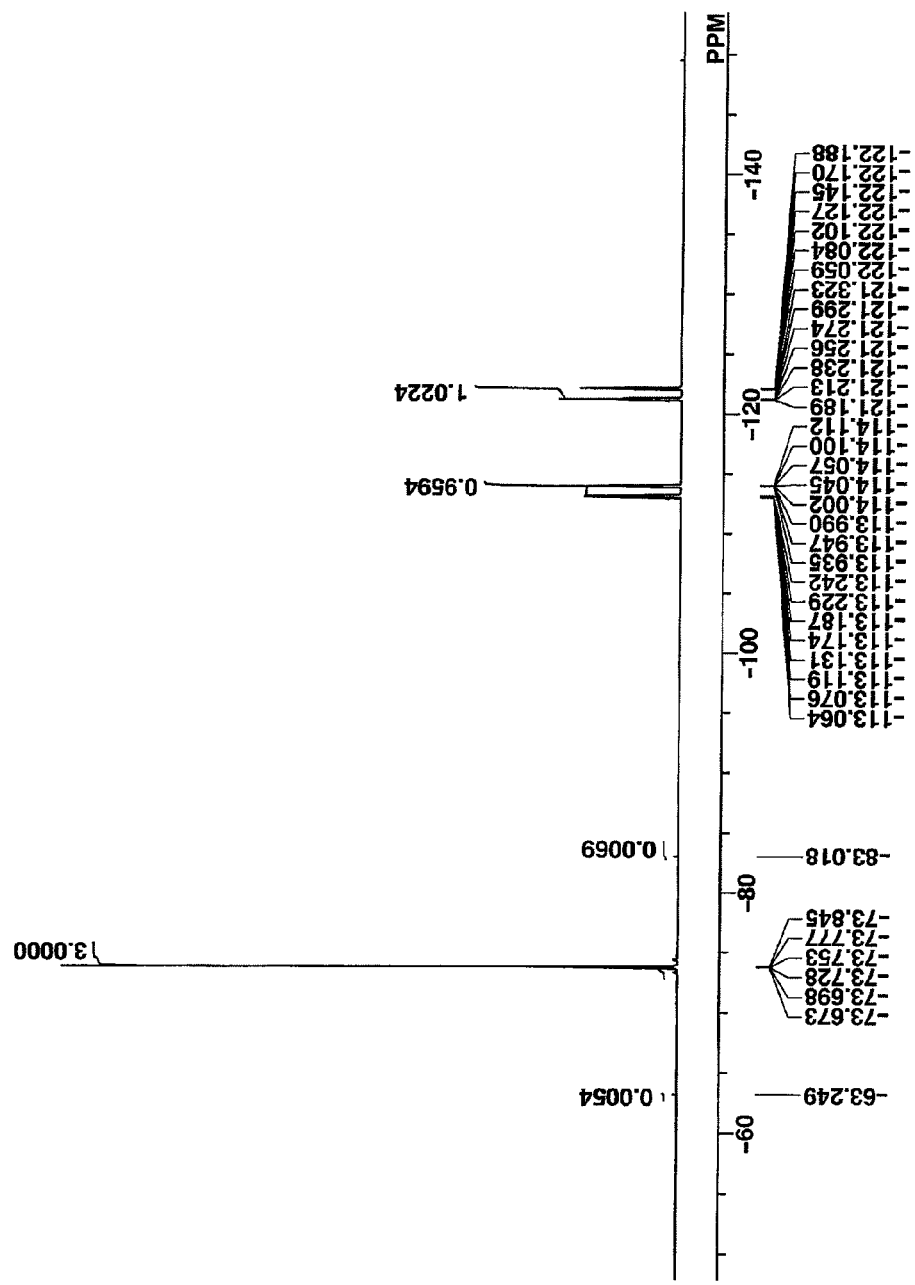
FIG. 6 is a diagram showing the $^{19}$F-NMR spectrum of PAG-3 in Comparative Synthesis Example 2.

Synthesis trial of 4-fluorophenyldiphenylsulfonium 1,1,3,3,3-pentafluoro-2-hydroxypropane-1-sulfonate In 139 g of methanol was dissolved 59.4 g (0.1 mole) of 4-fluorophenyldiphenylsulfonium 1,1,3,3,3-pentafluoro-2-pivaloyloxypropane-1-sulfonate in Comparative Synthesis Example 1. The solution was stirred under ice cooling, to which a solution of 8.0 g (0.2 mole) of sodium hydroxide in 24 g of water was added dropwise at a temperature below 20° C. The solution was stirred overnight at room temperature, after which 21 g of conc. hydrochloric acid and 60 g of water were added to quench the reaction. Methanol was removed in vacuum from the reaction solution, dichloromethane and water were added to the residue, and the organic layer was separated and concentrated again. Diisopropyl ether was added to the residue for crystallization. Filtration and drying gave white crystals. On $^{19}$F-NMR analysis of the crystal, however, the peak assigned to fluorine in 4-fluorophenyldiphenylsulfonium cation and observed near −104 ppm extinguished. The product was identified as 4-methoxyphenyldiphenylsulfonium 1,1,3,3,3-pentafluoro-2-hydroxypropane-1-sulfonate (PAG-3). The $^1$H-NMR and $^{19}$F-NMR spectra of PAG-3 are shown in FIGS. 5 and 6, respectively.

While 2 equivalents of sodium hydroxide was used in the above trial, it was found that 1 equivalent led to insufficient hydrolysis/alcoholysis of ester and 1.5 to 2 equivalents were necessary to drive hydrolysis/alcoholysis to completion. It was difficult to decompose only the ester while controlling decomposition of 4-fluorophenyldiphenylsulfonium cation.

Polymers were synthesized according to the following formulation.

Example 1-1

Synthesis of Polymer 1

A flask in nitrogen blanket was charged with 8.9 g of 4-fluorophenyldiphenylsulfonium 1,1,3,3,3-pentafluoro-2-methacryloyloxypropane-1-sulfonate, 12.7 g of 4-ethyltetracyclo[6.2.1.1$^{3,7}$.0$^{2,6}$]dodecan-4-yl methacrylate, 10.3 g of 2-oxo-4-oxahexahydro-3,5-methano-2H-cyclopenta[b]-furan-6-yl methacrylate, 8.2 g of 4-hydroxyphenyl methacrylate, 1.77 g of methyl 2,2'-azobisisobutyrate, 0.2 g of mercaptoethanol, and 84.8 g of methyl ethyl ketone (MEK) to form a monomer solution. Another flask in nitrogen blanket was charged with 23.3 g of MEK and heated at 80° C. with stirring, to which the monomer solution was added dropwise over 4 hours. After the completion of dropwise addition, the reaction solution was stirred for 2 hours for polymerization while maintaining the temperature of 80° C., and then cooled to room temperature. With vigorous stirring, the polymerization solution was added dropwise to 400 g of hexane whereupon a copolymer precipitate was collected by filtration. The copolymer was washed twice with a solvent mixture of 45.4 g of MEK and 194.6 g of hexane. On vacuum drying at 50° C. for 20 hours, 31 g of the copolymer (Polymer 1) was obtained in white powder form. The copolymer was analyzed by $^{13}$C-NMR, finding a copolymer compositional ratio of 10/30/30/30 mol % in the described order of monomers.

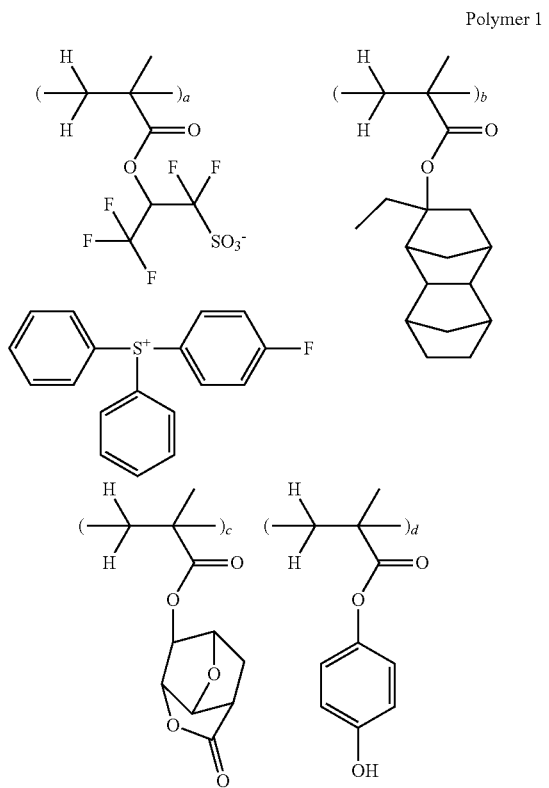

Polymer 1

Comparative Example 1-1

Synthesis of Comparative Polymer 1

Comparative Polymer 1 was similarly synthesized. Specifically, a flask in nitrogen blanket was charged with 8.7 g of triphenylsulfonium 1,1,3,3,3-pentafluoro-2-methacryloyloxypropane-1-sulfonate, 12.8 g of 4-ethyltetracyclo[6.2.1.1$^{3,7}$.0$^{2,6}$]dodecan-4-yl methacrylate, 10.4 g of 2-oxo-4-oxahexahydro-3,5-methano-2H-cyclopenta[b]-furan-6-yl methacrylate, 8.3 g of 4-hydroxyphenyl methacrylate, 1.78 g of methyl 2,2'-azobisisobutyrate, 0.2 g of mercaptoethanol, and 84.8 g of MEK to form a monomer solution. Another flask in nitrogen blanket was charged with 23.3 g of MEK and heated at 80° C. with stirring, to which the monomer solution was added dropwise over 4 hours. After the completion of dropwise addition, the reaction solution was stirred for 2 hours for polymerization while maintaining the temperature of 80° C., and then cooled to room temperature. With vigorous stirring, the polymerization solution was added dropwise to 400 g of hexane whereupon a copolymer precipitate was collected by filtration. The copolymer was washed twice with a solvent mixture of 45.4 g of MEK and 194.6 g of hexane. On vacuum drying at 50° C. for 20 hours, 31 g of the copolymer (Comparative Polymer 1) was obtained in white powder form. The copolymer was analyzed by $^{13}$C-NMR, finding a copolymer compositional ratio of 10/30/30/30 mol % in the described order of monomers.

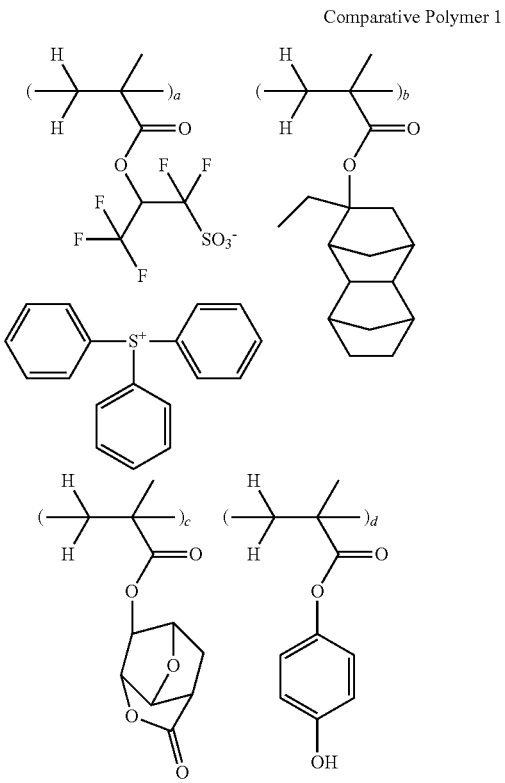

Comparative Polymer 1

Comparative Example 1-2

Synthesis of Comparative Polymer 2

A polymer was synthesized by the same procedure as in Example 1-1 except that 4-fluorophenyldiphenylsulfonium 1,1-difluoro-2-methacryloyloxyethanesulfonate described in JP-A 2010-77377 was used instead of 4-fluorophenyldiphenylsulfonium 1,1,3,3,3-pentafluoro-2-methacryloyloxypropane-1-sulfonate in Example 1-1. A polymer precipitated out during the process to inhibit a further progress of polymerization reaction.

Examples 1-2 to 1-13 and Comparative Examples 1-3, 1-4

Synthesis of Polymers 2 to 13 and Comparative Polymers 3 and 4

Resins (or polymers) as shown in Table 1 were prepared by the same procedure as in Example 1-1 aside from changing the type and amount of monomers. Polymer 13 was obtained by deprotection of ethoxyethyl from Polymer 12. Protection and deprotection on these polymers may be carried out according to the teaching of JP-A 2009-263487. In Table 1, a ratio of unit incorporated is expressed on a molar basis.

L-3: butano-4-lacton-3-yl methacrylate
L-4: 5-oxo-9-methoxycarbonyl-4-oxatricyclo[4.2.1.0$^{3,7}$]nonan-2-yl methacrylate
H-1: 4-hydroxyphenyl methacrylate
H-2: 6-hydroxy-2-naphthyl methacrylate
H-3: 4-hydroxystyrene
H-4: 3-hydroxytricyclo[3.3.1.1$^{3,7}$]dec-1-yl methacrylate The foregoing Polymers 1 to 13 and Comparative Polymers 1, 3, 4 are designated by P-1 to 13 and RP-1,3,4, respectively.

Preparation of Resist Compositions

Examples 2-1 to 2-12 & Comparative Examples 2-1 to 2-3

Resist compositions (R-1 to 12) or Comparative Resist compositions (RR-1 to 3) were prepared by combining, mixing and dissolving an inventive resin (P-1 to 11, 13) or comparative resin (RP-1,3,4), an acid generator, a quencher (or

TABLE 1

| | | Resin | Unit 1 (ratio) | Unit 2 (ratio) | Unit 3 (ratio) | Unit 4 (ratio) | Unit 5 (ratio) |
|---|---|---|---|---|---|---|---|
| Example | | | | | | | |
| | 1-1 | Polymer 1 | PM-1(0.10) | A-1(0.30) | L-1(0.30) | H-1(0.30) | |
| | 1-2 | Polymer 2 | PM-1(0.10) | A-1(0.30) | L-3(0.30) | H-1(0.30) | |
| | 1-3 | Polymer 3 | PM-1(0.10) | A-2(0.30) | L-1(0.30) | H-1(0.30) | |
| | 1-4 | Polymer 4 | PM-1(0.10) | A-3(0.30) | L-1(0.30) | H-2(0.30) | |
| | 1-5 | Polymer 5 | PM-1(0.10) | A-4(0.30) | L-1(0.30) | H-1(0.30) | |
| | 1-6 | Polymer 6 | PM-1(0.10) | A-5(0.30) | L-1(0.30) | H-1(0.30) | |
| | 1-7 | Polymer 7 | PM-1(0.10) | A-6(0.30) | L-1(0.30) | H-1(0.30) | |
| | 1-8 | Polymer 8 | PM-1(0.10) | A-7(0.30) | L-1(0.30) | H-1(0.30) | |
| | 1-9 | Polymer 9 | PM-1(0.10) | A-7(0.20) | A-8(0.10) | L-1(0.30) | H-1(0.30) |
| | 1-10 | Polymer 10 | PM-1(0.10) | A-1(0.30) | L-1(0.10) | L-3(0.20) | H-2(0.30) |
| | 1-11 | Polymer 11 | PM-1(0.10) | A-5(0.30) | L-2(0.10) | L-4(0.20) | H-1(0.30) |
| | 1-12 | Polymer 12 | PM-1(0.10) | A-8(0.30) | A-9(0.30) | L-4(0.30) | |
| | 1-13 | Polymer 13 | PM-1(0.10) | A-8(0.30) | H-3(0.30) | L-4(0.30) | |
| Comparative Example | | | | | | | |
| | 1-1 | Comparative Polymer 1 | PM-2(0.10) | A-1(0.30) | L-1(0.30) | H-1(0.30) | |
| | 1-2 | Comparative Polymer 2 | A polymer precipitated out during the process to inhibit further polymerization reaction. | | | | |
| | 1-3 | Comparative Polymer 3 | PM-1(0.10) | A-1(0.40) | L-1(0.30) | H-4(0.30) | |
| | 1-4 | Comparative Polymer 4 | | A-1(0.34) | L-1(0.33) | H-1(0.33) | |

The polymerized units in Table 1 represent the following compounds.
PM-1: 4-fluorophenyldiphenylsulfonium 1,1,3,3,3-pentafluoro-2-methacryloyloxypropane-1-sulfonate
PM-2: triphenylsulfonium 1,1,3,3,3-pentafluoro-2-methacryloyloxypropane-1-sulfonate
A-1: 4-ethyltetracyclo[6.2.1.1$^{3,7}$.0$^{2,6}$]dodecan-4-yl methacrylate
A-2: 2-ethyltricyclo[3.3.1.1$^{3,7}$]dec-2-yl methacrylate
A-3: 8-ethyltricyclo[5.2.1.0$^{2,6}$]dec-8-yl methacrylate
A-4: 1-ethylcyclohexyl methacrylate
A-5: 1-(1-methylethyl)cyclopentyl methacrylate
A-6: 6-methylspiro[4.5]dec-6-yl methacrylate
A-7: 1-methyl-1-(tricyclo[3.3.1.1$^{3,7}$]dec-1-yl)ethyl methacrylate
A-8: 4-t-amyloxystyrene
A-9: 4-(1-ethoxyethoxy)styrene
L-1: 2-oxo-4-oxahexahydro-3,5-methano-2H-cyclopenta[b]furan-6-yl methacrylate
L-2: 2-oxooxolan-3-yl methacrylate basic compound), and a solvent in accordance with the recipe shown in Table 2, and filtering through a Teflon® filter having a pore size of 0.2 µm.

TABLE 2

| | | Resist composition | Resin (pbw) | Acid generator (pbw) | Basic compound (pbw) | Solvent (pbw) |
|---|---|---|---|---|---|---|
| Example | | | | | | |
| | 2-1 | R-1 | P-1 (100) | | Base-1 (0.94) | Ternary (2,500) |
| | 2-2 | R-2 | P-2 (100) | | Base-1 (0.94) | Ternary (2,500) |
| | 2-3 | R-3 | P-3 (100) | | Base-1 (0.94) | Ternary (2,500) |
| | 2-4 | R-4 | P-4 (100) | | Base-1 (0.94) | Ternary (2,500) |
| | 2-5 | R-5 | P-5 (100) | | Base-1 (0.94) | Ternary (2,500) |
| | 2-6 | R-6 | P-6 (100) | | Base-1 (0.94) | Ternary (2,500) |

TABLE 2-continued

| | | Resist com-position | Resin (pbw) | Acid generator (pbw) | Basic compound (pbw) | Solvent (pbw) |
|---|---|---|---|---|---|---|
| | 2-7 | R-7 | P-7 (100) | | Base-1 (0.94) | Ternary (2,500) |
| | 2-8 | R-8 | P-8 (100) | | Base-1 (0.94) | Ternary (2,500) |
| | 2-9 | R-9 | P-9 (100) | | Base-1 (0.94) | Ternary (2,500) |
| | 2-10 | R-10 | P-10 (100) | | Base-1 (0.94) | Ternary (2,500) |
| | 2-11 | R-11 | P-11 (100) | | Base-1 (0.94) | Ternary (2,500) |
| | 2-12 | R-12 | P-13 (100) | | Base-1 (0.94) | Ternary (2,500) |
| Comparative Example | | | | | | |
| | 2-1 | RR-1 | RP-1 (100) | | Base-1 (0.94) | Ternary (2,500) |
| | 2-2 | RR-2 | RP-3 (100) | | Base-1 (0.94) | Ternary (2,500) |
| | 2-3 | RR-3 | RP-4 (100) | PAG-□ (10) | Base-1 (0.94) | Ternary (2,500) |

Components in Table 2 including acid generator, quencher, and solvent are shown below.

PAG-□: 4-fluorophenyldiphenylsulfonium 2-(adamantane-1-carbonyloxy)-1,1,3,3,3-hexafluoropropane-1-sulfonate Base-1: tri(2-methoxymethoxyethyl)amine Ternary: 1-methoxy-2-propyl acetate/1-methoxy-2-propanol/cyclohexanone solvent mixture (weight ratio: 1000/500/2000) containing 0.01 wt % of a surfactant PolyFox® PF636 (Omnova Solutions, Inc.).

Evaluation of Sensitivity and Resolution on EUV Lithography

Examples 3-1 to 3-12 & Comparative Examples 3-1 to 3-3

On a silicon wafer (diameter 4 inches, treated with hexamethyldisilazane HMDS), each of the inventive resist compositions (R-1 to 12) or comparative resist compositions (RR-1 to 3) was spin coated and prebaked at 105° C. for 60 seconds to form a resist film of 50 nm thick. The resist film was exposed by means of an EUV micro-stepper (NA 0.3, dipole illumination), baked (PEB) at the temperature shown in Table 3 for 60 seconds, and puddle developed for 30 seconds with a 2.38 wt % tetramethylammonium hydroxide (TMAH) aqueous solution, obtaining a positive pattern.

The resist pattern was evaluated as follows. The sensitivity or optimum exposure (Eop) was defined as the exposure dose (mJ/cm$^2$) which provided a 1:1 resolution at the top and bottom of a 35-nm line-and-space pattern. The resolution of the resist was defined as the minimum line width of a line-and-space pattern that was ascertained separate at the optimum exposure. The LER of a 35-nm line-and-space pattern was measured under SEM. The results are shown in Table 3.

TABLE 3

| | Resist com-position | PEB temp. (° C.) | Sensitivity (mJ/cm$^2$) | Resolution (nm) | LER (nm) |
|---|---|---|---|---|---|
| Example | | | | | |
| 3-1 | R-1 | 95 | 14 | 22 | 3.8 |
| 3-2 | R-2 | 85 | 15 | 24 | 5.0 |
| 3-3 | R-3 | 100 | 16 | 24 | 4.5 |
| 3-4 | R-4 | 95 | 14 | 24 | 4.2 |
| 3-5 | R-5 | 95 | 14 | 24 | 4.3 |
| 3-6 | R-6 | 85 | 14 | 24 | 4.4 |
| 3-7 | R-7 | 90 | 14 | 24 | 4.2 |
| 3-8 | R-8 | 100 | 16 | 20 | 3.6 |
| 3-9 | R-9 | 90 | 16 | 20 | 3.7 |
| 3-10 | R-10 | 90 | 14 | 24 | 5.0 |
| 3-11 | R-11 | 85 | 15 | 24 | 5.3 |
| 3-12 | R-12 | 85 | 14 | 24 | 5.0 |
| Comparative Example | | | | | |
| 3-1 | RR-1 | 90 | 17 | 26 | 5.5 |
| 3-2 | RR-2 | 90 | 35 | 30 | 8.0 |
| 3-3 | RR-3 | 90 | 13 | 35 | 8.0 |

It is evident from Table 3 that the resist compositions within the scope of the invention have a high sensitivity and improved resolution when processed by EUV lithography.

Positive resist patterns were also formed when a 3.84 wt % tetraethylammonium hydroxide aqueous solution, a 5.31 wt % tetrapropylammonium hydroxide aqueous solution, and a 6.78 wt % tetrabutylammonium hydroxide aqueous solution were used instead of the 2.38 wt % tetramethylammonium hydroxide aqueous solution. Resolution and LER were more or less improved.

Japanese Patent Application No. 2010-258496 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonium salt having the general formula (1):

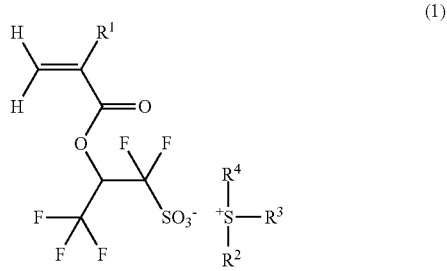

(1)

wherein $R^1$ is hydrogen, fluorine, methyl or trifluoromethyl, $R^2$, $R^3$, and $R^4$ are each independently a substituted or unsubstituted, straight or branched $C_1$-$C_{10}$ alkyl, alkenyl or oxoalkyl group, a substituted or unsubstituted $C_6$-$C_{18}$ aryl, aralkyl or aryloxoalkyl group, or 4-fluorophenyl group, any two of $R^2$, $R^3$, and $R^4$ may bond together to form a ring with the sulfur atom, with the proviso that at least one of $R^2$, $R^3$, and $R^4$ is a 4-fluorophenyl group.

2. A method for preparing the sulfonium salt of formula (1) as set forth in claim 1, comprising effecting ion exchange between an ammonium salt having the general formula (1b) and a 4-fluorophenylsulfonium salt having the general formula (1c),

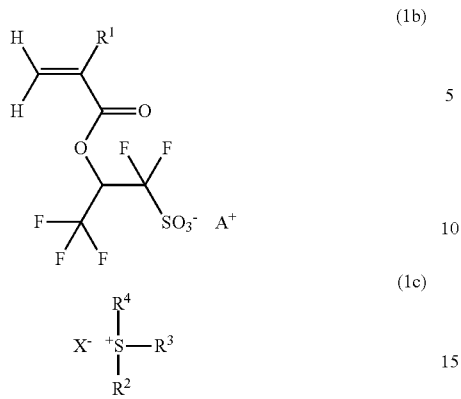

(1b)

(1c)

wherein $R^1$ is hydrogen, fluorine, methyl or trifluoromethyl, $R^2$, $R^3$, and $R^4$ are each independently a substituted or unsubstituted, straight or branched $C_1$-$C_{10}$ alkyl, alkenyl or oxoalkyl group, a substituted or unsubstituted $C_6$-$C_{18}$ aryl, aralkyl or aryloxoalkyl group, or 4-fluorophenyl group, any two of $R^2$, $R^3$, and $R^4$ may bond together to form a ring with the sulfur atom, with the proviso that at least one of $R^2$, $R^3$, and $R^4$ is a 4-fluorophenyl group, $A^+$ is an ammonium cation or a $C_1$-$C_{16}$ primary, secondary, tertiary or quaternary ammonium cation, and $X^-$ is a fluoride ion, chloride ion, bromide ion, iodide ion or methyl sulfate.

* * * * *